(12) United States Patent
Kamath et al.

(10) Patent No.: US 8,565,849 B2
(45) Date of Patent: Oct. 22, 2013

(54) TRANSCUTANEOUS ANALYTE SENSOR

(75) Inventors: Apurv Ullas Kamath, San Diego, CA (US); James Brauker, Addison, MI (US); J. Michael Dobbles, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 614 days.

(21) Appl. No.: 12/780,739

(22) Filed: May 14, 2010

(65) Prior Publication Data

US 2010/0228109 A1 Sep. 9, 2010

Related U.S. Application Data

(63) Continuation of application No. 11/077,765, filed on Mar. 10, 2005.

(60) Provisional application No. 60/587,787, filed on Jul. 13, 2004, provisional application No. 60/587,800, filed on Jul. 13, 2004, provisional application No. 60/614,683, filed on Sep. 30, 2004, provisional application No. 60/614,764, filed on Sep. 30, 2004.

(51) Int. Cl.
*A61B 5/05* (2006.01)

(52) U.S. Cl.
USPC .......................... 600/345; 600/347; 600/365

(58) Field of Classification Search
USPC ........ 600/309, 316, 345–347, 365; 435/4, 14; 436/68; 422/50, 420–429; 204/403.01–403.15; 702/23; 604/64–66
See application file for complete search history.

(56) References Cited

U.S. PATENT DOCUMENTS

| | | | |
|---|---|---|---|
| 2,057,029 A | 10/1936 | McC. Johnstone |
| 2,402,306 A | 6/1946 | Turkel |
| 3,210,578 A | 10/1965 | Sherer |
| 3,219,533 A | 11/1965 | Mullins |
| 3,728,678 A | 4/1973 | Tong |
| 3,826,244 A | 7/1974 | Salcman et al. |
| 3,898,984 A | 8/1975 | Mandel et al. |
| 3,926,760 A | 12/1975 | Allen et al. |
| 3,929,971 A | 12/1975 | Roy |
| 3,943,918 A | 3/1976 | Lewis |
| 3,957,613 A | 5/1976 | Macur |
| 3,964,974 A | 6/1976 | Banauch et al. |
| 3,966,580 A | 6/1976 | Janata et al. |
| 3,979,274 A | 9/1976 | Newman |

(Continued)

FOREIGN PATENT DOCUMENTS

| EP | 0 098 592 | 1/1984 |
|---|---|---|
| EP | 0 127 958 | 12/1984 |

(Continued)

OTHER PUBLICATIONS

US 7,530,950, 05/2009, Brister et al., (withdrawn).

(Continued)

*Primary Examiner* — Patricia Mallari
*Assistant Examiner* — Michael D'Angelo
(74) *Attorney, Agent, or Firm* — Knobbe, Martens, Olson & Bear, LLP

(57) ABSTRACT

The present invention relates generally to systems and methods for measuring an analyte in a host. More particularly, the present invention relates to systems and methods for transcutaneous measurement of glucose in a host.

18 Claims, 23 Drawing Sheets

(56) References Cited

U.S. PATENT DOCUMENTS

| | | |
|---|---|---|
| 3,982,530 A | 9/1976 | Storch |
| 4,003,621 A | 1/1977 | Lamp |
| 4,024,312 A | 5/1977 | Korpman |
| 4,036,749 A | 7/1977 | Anderson |
| 4,037,563 A | 7/1977 | Pflueger et al. |
| 4,040,908 A | 8/1977 | Clark, Jr. |
| 4,052,754 A | 10/1977 | Homsy |
| 4,067,322 A | 1/1978 | Johnson |
| 4,068,660 A | 1/1978 | Beck |
| 4,073,713 A | 2/1978 | Newman |
| 4,076,656 A | 2/1978 | White et al. |
| 4,116,920 A | 9/1978 | Honma et al. |
| 4,172,770 A | 10/1979 | Semersky et al. |
| 4,197,840 A | 4/1980 | Beck et al. |
| 4,215,703 A | 8/1980 | Willson |
| 4,240,889 A | 12/1980 | Yoda et al. |
| 4,253,469 A | 3/1981 | Aslan |
| 4,255,500 A | 3/1981 | Hooke |
| 4,259,540 A | 3/1981 | Sabia |
| 4,319,578 A | 3/1982 | Enger |
| 4,327,725 A | 5/1982 | Cortese et al. |
| 4,353,888 A | 10/1982 | Sefton |
| 4,374,013 A | 2/1983 | Enfors |
| 4,378,016 A | 3/1983 | Loeb |
| 4,388,166 A | 6/1983 | Suzuki et al. |
| 4,402,694 A | 9/1983 | Ash et al. |
| 4,403,847 A | 9/1983 | Chrestensen |
| 4,403,984 A | 9/1983 | Ash et al. |
| 4,415,666 A | 11/1983 | D'Orazio et al. |
| 4,431,004 A | 2/1984 | Bessman et al. |
| 4,436,094 A | 3/1984 | Cerami |
| 4,442,841 A | 4/1984 | Uehara et al. |
| 4,454,295 A | 6/1984 | Wittmann et al. |
| 4,486,290 A | 12/1984 | Cahalan et al. |
| 4,494,950 A | 1/1985 | Fischell |
| 4,506,680 A | 3/1985 | Stokes |
| RE31,916 E | 6/1985 | Oswin et al. |
| 4,538,616 A | 9/1985 | Rogoff |
| 4,554,927 A | 11/1985 | Fussell |
| 4,565,666 A | 1/1986 | Cahalan et al. |
| 4,577,642 A | 3/1986 | Stokes |
| 4,578,215 A | 3/1986 | Bradley |
| 4,579,120 A | 4/1986 | MacGregor |
| 4,583,976 A | 4/1986 | Ferguson |
| 4,619,793 A | 10/1986 | Lee |
| RE32,361 E | 2/1987 | Duggan |
| 4,655,880 A | 4/1987 | Liu |
| 4,663,824 A | 5/1987 | Kenmochi |
| 4,671,288 A | 6/1987 | Gough |
| 4,672,970 A | 6/1987 | Uchida et al. |
| 4,675,346 A | 6/1987 | Lin et al. |
| 4,680,268 A | 7/1987 | Clark, Jr. |
| 4,703,756 A | 11/1987 | Gough et al. |
| 4,711,251 A | 12/1987 | Stokes |
| 4,721,677 A | 1/1988 | Clark |
| 4,731,726 A | 3/1988 | Allen |
| 4,753,652 A | 6/1988 | Langer et al. |
| 4,757,022 A | 7/1988 | Shults et al. |
| 4,759,828 A | 7/1988 | Young et al. |
| 4,761,748 A | 8/1988 | Le Rat et al. |
| 4,781,798 A | 11/1988 | Gough |
| 4,795,435 A | 1/1989 | Steer |
| 4,803,243 A | 2/1989 | Fujimoto et al. |
| 4,805,625 A | 2/1989 | Wyler |
| 4,810,470 A | 3/1989 | Burkhardt et al. |
| 4,826,706 A | 5/1989 | Hilker et al. |
| 4,831,070 A | 5/1989 | McInally et al. |
| 4,849,458 A | 7/1989 | Reed et al. |
| 4,852,573 A | 8/1989 | Kennedy |
| 4,858,615 A | 8/1989 | Meinema |
| 4,871,440 A | 10/1989 | Nagata et al. |
| 4,889,744 A | 12/1989 | Quaid |
| 4,890,620 A | 1/1990 | Gough |
| 4,890,621 A | 1/1990 | Hakky |
| 4,919,141 A | 4/1990 | Zier et al. |
| 4,927,516 A | 5/1990 | Yamaguchi et al. |
| 4,944,299 A | 7/1990 | Silvian |
| 4,952,618 A | 8/1990 | Olsen |
| 4,953,552 A | 9/1990 | DeMarzo |
| 4,958,148 A | 9/1990 | Olson |
| 4,960,594 A | 10/1990 | Honeycutt |
| 4,963,595 A | 10/1990 | Ward et al. |
| 4,974,929 A | 12/1990 | Curry |
| 4,984,929 A | 1/1991 | Rock et al. |
| 4,986,271 A | 1/1991 | Wilkins |
| 4,986,671 A | 1/1991 | Sun et al. |
| 4,988,341 A | 1/1991 | Columbus et al. |
| 4,988,758 A | 1/1991 | Fukuda et al. |
| 4,994,167 A | 2/1991 | Shults et al. |
| 5,002,572 A | 3/1991 | Picha |
| 5,007,929 A | 4/1991 | Quaid |
| 5,030,333 A | 7/1991 | Clark, Jr. |
| 5,050,612 A | 9/1991 | Matsumura |
| 5,055,171 A | 10/1991 | Peck |
| 5,059,654 A | 10/1991 | Hou et al. |
| 5,068,536 A | 11/1991 | Rosenthal |
| 5,082,550 A | 1/1992 | Rishpon et al. |
| 5,097,834 A | 3/1992 | Skrabal |
| 5,101,814 A | 4/1992 | Palti |
| 5,108,819 A | 4/1992 | Heller et al. |
| 5,137,028 A | 8/1992 | Nishimura |
| 5,140,985 A | 8/1992 | Schroeder et al. |
| 5,160,418 A | 11/1992 | Mullen |
| 5,162,407 A | 11/1992 | Turner |
| 5,165,407 A | 11/1992 | Wilson et al. |
| 5,171,689 A | 12/1992 | Kawaguri et al. |
| 5,190,041 A | 3/1993 | Palti |
| 5,198,771 A | 3/1993 | Fidler et al. |
| 5,202,261 A | 4/1993 | Musho et al. |
| 5,208,147 A | 5/1993 | Kagenow et al. |
| 5,235,003 A | 8/1993 | Ward et al. |
| 5,243,983 A | 9/1993 | Tarr et al. |
| 5,249,576 A | 10/1993 | Goldberger et al. |
| 5,264,104 A | 11/1993 | Gregg et al. |
| 5,265,999 A | 11/1993 | Wenschhof et al. |
| 5,266,179 A | 11/1993 | Nankai et al. |
| 5,269,891 A | 12/1993 | Colin |
| 5,271,736 A | 12/1993 | Picha |
| 5,281,319 A | 1/1994 | Kaneko et al. |
| 5,282,848 A | 2/1994 | Schmitt |
| 5,284,570 A | 2/1994 | Savage et al. |
| 5,285,513 A | 2/1994 | Kaufman et al. |
| 5,287,753 A | 2/1994 | Routh et al. |
| 5,299,571 A | 4/1994 | Mastrototaro |
| 5,302,440 A | 4/1994 | Davis |
| 5,304,468 A | 4/1994 | Phillips et al. |
| 5,307,263 A | 4/1994 | Brown |
| 5,312,361 A | 5/1994 | Zadini et al. |
| 5,314,471 A | 5/1994 | Brauker et al. |
| 5,316,008 A | 5/1994 | Suga et al. |
| 5,322,063 A | 6/1994 | Allen et al. |
| 5,324,322 A | 6/1994 | Grill et al. |
| 5,326,356 A | 7/1994 | Della Valle et al. |
| 5,330,634 A | 7/1994 | Wong et al. |
| 5,331,555 A | 7/1994 | Hashimoto et al. |
| 5,336,102 A | 8/1994 | Cairns et al. |
| 5,337,747 A | 8/1994 | Neftel |
| 5,344,454 A | 9/1994 | Clarke et al. |
| 5,348,788 A | 9/1994 | White |
| 5,352,348 A | 10/1994 | Young et al. |
| 5,354,449 A | 10/1994 | Band et al. |
| 5,356,786 A | 10/1994 | Heller et al. |
| 5,358,409 A | 10/1994 | Obara |
| 5,362,761 A | 11/1994 | Uragami et al. |
| 5,368,224 A | 11/1994 | Richardson et al. |
| 5,372,133 A | 12/1994 | Hogen Esch |
| 5,372,719 A | 12/1994 | Afeyan et al. |
| 5,376,070 A | 12/1994 | Purvis et al. |
| 5,380,536 A | 1/1995 | Hubbell et al. |
| 5,384,028 A | 1/1995 | Ito |
| 5,390,671 A | 2/1995 | Lord et al. |
| 5,391,250 A | 2/1995 | Cheney, II et al. |
| 5,397,848 A | 3/1995 | Yang et al. |
| 5,411,647 A | 5/1995 | Johnson et al. |

(56) References Cited

U.S. PATENT DOCUMENTS

| | | |
|---|---|---|
| 5,411,866 A | 5/1995 | Luong et al. |
| 5,425,717 A | 6/1995 | Mohiuddin |
| 5,426,032 A | 6/1995 | Phillips et al. |
| 5,429,129 A | 7/1995 | Lovejoy et al. |
| 5,429,735 A | 7/1995 | Johnson et al. |
| 5,431,160 A | 7/1995 | Wilkins |
| 5,431,921 A | 7/1995 | Thombre |
| 5,451,260 A | 9/1995 | Versteeg et al. |
| 5,453,199 A | 9/1995 | Afeyan et al. |
| 5,453,278 A | 9/1995 | Chan et al. |
| 5,462,051 A | 10/1995 | Oka et al. |
| 5,462,064 A | 10/1995 | D'Angelo et al. |
| 5,474,552 A | 12/1995 | Palti |
| 5,482,473 A | 1/1996 | Lord et al. |
| 5,494,562 A | 2/1996 | Maley et al. |
| 5,497,772 A | 3/1996 | Schulman et al. |
| 5,502,396 A | 3/1996 | Desarzens et al. |
| 5,507,288 A | 4/1996 | Bocker et al. |
| 5,513,636 A | 5/1996 | Palti |
| 5,518,601 A | 5/1996 | Foos et al. |
| 5,531,878 A | 7/1996 | Vadgama et al. |
| 5,540,828 A | 7/1996 | Yacynych |
| 5,545,220 A | 8/1996 | Andrews et al. |
| 5,545,223 A | 8/1996 | Neuenfeldt et al. |
| 5,549,675 A | 8/1996 | Neuenfeldt et al. |
| 5,552,112 A | 9/1996 | Schiffmann et al. |
| 5,553,616 A | 9/1996 | Ham et al. |
| 5,564,439 A | 10/1996 | Picha |
| 5,568,806 A | 10/1996 | Cheney, II et al. |
| 5,569,186 A | 10/1996 | Lord et al. |
| 5,569,462 A | 10/1996 | Martinson et al. |
| 5,575,293 A | 11/1996 | Miller et al. |
| 5,575,930 A | 11/1996 | Tietje-Girault et al. |
| 5,582,184 A | 12/1996 | Erickson et al. |
| 5,584,813 A | 12/1996 | Livingston et al. |
| 5,584,876 A | 12/1996 | Bruchman et al. |
| 5,586,553 A | 12/1996 | Halili et al. |
| 5,587,273 A | 12/1996 | Yan et al. |
| 5,589,563 A | 12/1996 | Ward et al. |
| 5,590,651 A | 1/1997 | Shaffer et al. |
| 5,593,440 A | 1/1997 | Brauker et al. |
| 5,593,852 A | 1/1997 | Heller et al. |
| 5,611,900 A | 3/1997 | Worden et al. |
| 5,653,756 A | 8/1997 | Clarke et al. |
| 5,653,863 A | 8/1997 | Genshaw et al. |
| 5,658,330 A | 8/1997 | Carlisle et al. |
| 5,660,163 A | 8/1997 | Schulman et al. |
| 5,662,616 A | 9/1997 | Bousquet |
| 5,676,820 A | 10/1997 | Wang et al. |
| 5,686,829 A | 11/1997 | Girault |
| 5,695,623 A | 12/1997 | Michel et al. |
| 5,696,314 A | 12/1997 | McCaffrey et al. |
| 5,706,807 A | 1/1998 | Picha |
| 5,711,302 A | 1/1998 | Lampropoulos et al. |
| 5,711,861 A | 1/1998 | Ward et al. |
| 5,713,888 A | 2/1998 | Neuenfeldt et al. |
| 5,714,123 A | 2/1998 | Sohrab |
| 5,733,336 A | 3/1998 | Neuenfeldt et al. |
| 5,741,330 A | 4/1998 | Brauker et al. |
| 5,741,634 A | 4/1998 | Nozoe et al. |
| 5,743,262 A | 4/1998 | Lepper, Jr. et al. |
| 5,749,907 A | 5/1998 | Mann |
| 5,756,632 A | 5/1998 | Ward et al. |
| 5,766,151 A | 6/1998 | Valley et al. |
| 5,776,324 A | 7/1998 | Usala |
| 5,777,060 A | 7/1998 | Van Antwerp |
| 5,781,455 A | 7/1998 | Hyodo |
| 5,782,912 A | 7/1998 | Brauker et al. |
| 5,786,439 A | 7/1998 | Van Antwerp et al. |
| 5,787,900 A | 8/1998 | Butler et al. |
| 5,791,344 A | 8/1998 | Schulman et al. |
| 5,795,774 A | 8/1998 | Matsumoto et al. |
| 5,798,065 A | 8/1998 | Picha |
| 5,800,420 A | 9/1998 | Gross |
| 5,800,529 A | 9/1998 | Brauker et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,814,599 A | 9/1998 | Mitragotri et al. |
| 5,822,715 A | 10/1998 | Worthington et al. |
| 5,823,802 A | 10/1998 | Bartley |
| 5,836,887 A | 11/1998 | Oka et al. |
| 5,836,989 A | 11/1998 | Shelton |
| 5,837,728 A | 11/1998 | Purcell |
| 5,840,240 A | 11/1998 | Stenoien et al. |
| 5,851,197 A | 12/1998 | Marano et al. |
| 5,861,019 A | 1/1999 | Sun et al. |
| 5,871,499 A | 2/1999 | Hahn et al. |
| 5,871,514 A | 2/1999 | Wiklund et al. |
| 5,879,373 A | 3/1999 | Roper et al. |
| 5,882,494 A | 3/1999 | Van Antwerp |
| 5,897,578 A | 4/1999 | Wiklund et al. |
| 5,904,708 A | 5/1999 | Goedeke |
| 5,913,998 A | 6/1999 | Butler et al. |
| 5,914,026 A | 6/1999 | Blubaugh, Jr. et al. |
| 5,916,445 A | 6/1999 | Hjerten et al. |
| 5,919,215 A | 7/1999 | Wiklund et al. |
| 5,928,130 A | 7/1999 | Schmidt |
| 5,931,814 A | 8/1999 | Alex et al. |
| 5,933,136 A | 8/1999 | Brown |
| 5,935,785 A | 8/1999 | Reber et al. |
| 5,944,661 A | 8/1999 | Swette et al. |
| 5,954,643 A | 9/1999 | VanAntwerp et al. |
| 5,957,854 A | 9/1999 | Besson et al. |
| 5,959,050 A | 9/1999 | Mosbach et al. |
| 5,961,451 A | 10/1999 | Reber et al. |
| 5,964,804 A | 10/1999 | Brauker et al. |
| 5,964,993 A | 10/1999 | Blubaugh et al. |
| 5,965,380 A | 10/1999 | Heller et al. |
| 5,967,986 A | 10/1999 | Cimochowski et al. |
| 5,971,922 A | 10/1999 | Arita et al. |
| 5,972,199 A | 10/1999 | Heller et al. |
| 5,976,085 A | 11/1999 | Kimball et al. |
| 5,995,860 A | 11/1999 | Sun et al. |
| 6,001,067 A | 12/1999 | Shults et al. |
| 6,013,113 A | 1/2000 | Mika |
| 6,016,448 A | 1/2000 | Busacker et al. |
| 6,017,435 A | 1/2000 | Hassard et al. |
| 6,027,445 A | 2/2000 | Von Bahr |
| 6,048,691 A | 4/2000 | Maracas |
| 6,049,727 A | 4/2000 | Crothall |
| 6,051,372 A | 4/2000 | Bayerl et al. |
| 6,051,389 A | 4/2000 | Ahl et al. |
| 6,057,377 A | 5/2000 | Sasaki et al. |
| 6,059,946 A | 5/2000 | Yukawa et al. |
| 6,063,637 A | 5/2000 | Arnold et al. |
| 6,065,154 A | 5/2000 | Hulings et al. |
| 6,081,735 A | 6/2000 | Diab et al. |
| 6,081,736 A | 6/2000 | Colvin et al. |
| 6,083,523 A | 7/2000 | Dionne et al. |
| 6,088,608 A | 7/2000 | Schulman et al. |
| 6,091,975 A | 7/2000 | Daddona et al. |
| 6,093,156 A | 7/2000 | Cunningham et al. |
| 6,093,172 A | 7/2000 | Funderburk et al. |
| 6,101,404 A | 8/2000 | Yoon et al. |
| 6,103,033 A | 8/2000 | Say et al. |
| 6,103,533 A | 8/2000 | Say et al. |
| 6,107,083 A | 8/2000 | Collins et al. |
| 6,115,622 A | 9/2000 | Minoz |
| 6,117,290 A | 9/2000 | Say |
| 6,119,028 A | 9/2000 | Schulman et al. |
| 6,122,536 A | 9/2000 | Sun et al. |
| 6,123,827 A | 9/2000 | Wong et al. |
| 6,134,461 A | 10/2000 | Say et al. |
| 6,135,978 A | 10/2000 | Houben et al. |
| 6,144,869 A | 11/2000 | Berner et al. |
| 6,144,871 A | 11/2000 | Saito et al. |
| 6,162,611 A | 12/2000 | Heller et al. |
| 6,168,568 B1 | 1/2001 | Gavriely |
| 6,169,155 B1 | 1/2001 | Alvarez et al. |
| 6,175,752 B1 | 1/2001 | Say et al. |
| 6,180,416 B1 | 1/2001 | Kurnik et al. |
| 6,187,062 B1 | 2/2001 | Oweis et al. |
| 6,200,772 B1 | 3/2001 | Vadgama et al. |

(56) References Cited

U.S. PATENT DOCUMENTS

| | | |
|---|---|---|
| 6,201,980 B1 | 3/2001 | Darrow et al. |
| 6,201,993 B1 | 3/2001 | Kruse et al. |
| 6,208,894 B1 | 3/2001 | Schulman et al. |
| 6,212,416 B1 | 4/2001 | Ward et al. |
| 6,212,424 B1 | 4/2001 | Robinson |
| 6,219,574 B1 | 4/2001 | Cormier et al. |
| 6,223,083 B1 | 4/2001 | Rosar |
| 6,230,059 B1 | 5/2001 | Duffin |
| 6,231,879 B1 | 5/2001 | Li et al. |
| 6,232,783 B1 | 5/2001 | Merrill |
| 6,233,080 B1 | 5/2001 | Brenner et al. |
| 6,233,471 B1 | 5/2001 | Berner et al. |
| 6,248,067 B1 | 6/2001 | Causey, III et al. |
| 6,251,280 B1 | 6/2001 | Dai et al. |
| 6,255,592 B1 | 7/2001 | Pennington et al. |
| 6,256,522 B1 | 7/2001 | Schultz |
| 6,259,937 B1 | 7/2001 | Schulman et al. |
| 6,268,161 B1 | 7/2001 | Han et al. |
| 6,272,364 B1 | 8/2001 | Kurnik |
| 6,272,480 B1 | 8/2001 | Tresp et al. |
| 6,274,285 B1 | 8/2001 | Gries et al. |
| 6,274,686 B1 | 8/2001 | Mosbach et al. |
| 6,275,717 B1 | 8/2001 | Gross et al. |
| 6,284,478 B1 | 9/2001 | Heller et al. |
| 6,285,897 B1 | 9/2001 | Kilcoyne et al. |
| 6,293,925 B1 | 9/2001 | Safabash et al. |
| 6,296,615 B1 | 10/2001 | Brockway et al. |
| 6,299,578 B1 | 10/2001 | Kurnik et al. |
| 6,302,855 B1 | 10/2001 | Lav et al. |
| 6,309,351 B1 | 10/2001 | Kurnik et al. |
| 6,309,384 B1 | 10/2001 | Harrington et al. |
| 6,309,884 B1 | 10/2001 | Cooper et al. |
| 6,310,110 B1 | 10/2001 | Markowitz et al. |
| 6,315,738 B1 | 11/2001 | Nishikawa et al. |
| 6,319,566 B1 | 11/2001 | Polanyi et al. |
| 6,325,978 B1 | 12/2001 | Labuda et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,336,269 B1 | 1/2002 | Eldridge et al. |
| 6,343,225 B1 | 1/2002 | Clark, Jr. |
| 6,356,776 B1 | 3/2002 | Berner et al. |
| 6,360,888 B1 | 3/2002 | McIvor et al. |
| 6,365,670 B1 | 4/2002 | Fry |
| 6,366,794 B1 | 4/2002 | Moussy et al. |
| 6,368,141 B1 | 4/2002 | VanAntwerp et al. |
| 6,368,274 B1 | 4/2002 | Van Antwerp et al. |
| 6,370,941 B2 | 4/2002 | Nakamura |
| 6,371,963 B1 | 4/2002 | Nishtala et al. |
| 6,379,317 B1 | 4/2002 | Kintzig et al. |
| 6,413,393 B1 | 7/2002 | Van Antwerp et al. |
| 6,416,651 B1 | 7/2002 | Millar |
| 6,418,332 B1 | 7/2002 | Mastrototaro et al. |
| 6,424,847 B1 | 7/2002 | Mastrototaro et al. |
| 6,447,448 B1 | 9/2002 | Ishikawa et al. |
| 6,447,542 B1 | 9/2002 | Weadock |
| 6,461,496 B1 | 10/2002 | Feldman et al. |
| 6,466,810 B1 | 10/2002 | Ward et al. |
| 6,471,689 B1 | 10/2002 | Joseph et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,484,046 B1 | 11/2002 | Say et al. |
| 6,484,132 B1 | 11/2002 | Hively et al. |
| 6,487,429 B2 | 11/2002 | Hockersmith et al. |
| 6,494,830 B1 | 12/2002 | Wessel |
| 6,498,043 B1 | 12/2002 | Schulman et al. |
| 6,510,329 B2 | 1/2003 | Heckel |
| 6,512,939 B1 | 1/2003 | Colvin et al. |
| 6,514,718 B2 | 2/2003 | Heller et al. |
| 6,520,326 B2 | 2/2003 | McIvor et al. |
| 6,520,997 B1 | 2/2003 | Pekkarinen et al. |
| 6,526,298 B1 | 2/2003 | Khalil et al. |
| 6,527,729 B1 | 3/2003 | Turcott |
| 6,537,318 B1 | 3/2003 | Ita et al. |
| 6,541,107 B1 | 4/2003 | King et al. |
| 6,544,212 B2 | 4/2003 | Galley et al. |
| 6,545,085 B2 | 4/2003 | Kilgour et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,558,320 B1 * | 5/2003 | Causey et al. ................. 600/300 |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,572,545 B2 | 6/2003 | Knobbe et al. |
| 6,572,745 B2 | 6/2003 | Rappin et al. |
| 6,574,490 B2 | 6/2003 | Abbink et al. |
| 6,575,905 B2 | 6/2003 | Knobbe et al. |
| 6,579,498 B1 | 6/2003 | Eglise |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,589,229 B1 | 7/2003 | Connelly et al. |
| 6,595,919 B2 | 7/2003 | Berner et al. |
| 6,605,072 B2 | 8/2003 | Struys et al. |
| 6,612,984 B1 | 9/2003 | Kerr |
| 6,613,379 B2 | 9/2003 | Ward et al. |
| 6,618,934 B1 | 9/2003 | Feldman et al. |
| 6,633,772 B2 | 10/2003 | Ford et al. |
| 6,641,533 B2 | 11/2003 | Causey et al. |
| 6,645,181 B1 | 11/2003 | Lavi et al. |
| 6,654,625 B1 | 11/2003 | Say et al. |
| 6,673,596 B1 | 1/2004 | Sayler et al. |
| 6,695,860 B1 | 2/2004 | Ward et al. |
| 6,702,857 B2 | 3/2004 | Brauker et al. |
| 6,705,833 B2 | 3/2004 | Tam et al. |
| 6,721,587 B2 | 4/2004 | Gough |
| 6,736,777 B2 | 5/2004 | Kim et al. |
| 6,740,059 B2 | 5/2004 | Flaherty |
| 6,741,877 B1 | 5/2004 | Shults et al. |
| 6,743,635 B2 | 6/2004 | Neel et al. |
| 6,802,957 B2 | 10/2004 | Jung et al. |
| 6,809,653 B1 | 10/2004 | Mann et al. |
| 6,815,186 B2 | 11/2004 | Clark, Jr. |
| 6,830,551 B1 | 12/2004 | Uchigaki et al. |
| 6,869,413 B2 | 3/2005 | Langley et al. |
| 6,875,386 B1 | 4/2005 | Ward et al. |
| 6,885,883 B2 | 4/2005 | Parris et al. |
| 6,891,317 B2 | 5/2005 | Pei et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,931,327 B2 | 8/2005 | Goode, Jr. et al. |
| 6,936,006 B2 | 8/2005 | Sabra |
| 6,952,604 B2 | 10/2005 | DeNuzzio et al. |
| 6,965,791 B1 | 11/2005 | Hitchcock et al. |
| 6,998,247 B2 | 2/2006 | Monfre et al. |
| 7,003,336 B2 | 2/2006 | Holker et al. |
| 7,003,341 B2 | 2/2006 | Say et al. |
| 7,011,630 B2 | 3/2006 | Desai et al. |
| 7,025,743 B2 | 4/2006 | Mann et al. |
| 7,060,059 B2 | 6/2006 | Keith et al. |
| 7,070,580 B2 | 7/2006 | Nielsen |
| 7,074,307 B2 | 7/2006 | Simpson et al. |
| 7,078,582 B2 | 7/2006 | Stebbings et al. |
| 7,098,803 B2 | 8/2006 | Mann et al. |
| 7,134,999 B2 | 11/2006 | Brauker et al. |
| 7,153,265 B2 | 12/2006 | Vachon |
| 7,169,289 B2 | 1/2007 | Schulein et al. |
| 7,190,988 B2 | 3/2007 | Say et al. |
| 7,207,974 B2 | 4/2007 | Safabash et al. |
| 7,267,665 B2 | 9/2007 | Steil et al. |
| 7,276,029 B2 | 10/2007 | Goode et al. |
| 7,295,867 B2 | 11/2007 | Berner et al. |
| 7,299,082 B2 | 11/2007 | Feldman et al. |
| 7,324,012 B2 | 1/2008 | Mann et al. |
| 7,344,499 B1 | 3/2008 | Prausnitz et al. |

(56) References Cited

U.S. PATENT DOCUMENTS

| | | |
|---|---|---|
| 7,381,184 B2 | 6/2008 | Funderburk et al. |
| 7,399,277 B2 | 7/2008 | Saidara et al. |
| 7,426,408 B2 | 9/2008 | DeNuzzio et al. |
| 7,519,408 B2 | 4/2009 | Rasdal et al. |
| 7,582,059 B2 | 9/2009 | Funderburk et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,697,967 B2 | 4/2010 | Stafford |
| 7,713,574 B2 | 5/2010 | Brister et al. |
| 7,879,010 B2 | 2/2011 | Hunn et al. |
| 7,885,697 B2 | 2/2011 | Brister et al. |
| 7,946,984 B2 | 5/2011 | Brister et al. |
| 7,949,381 B2 | 5/2011 | Brister et al. |
| 8,229,534 B2 | 7/2012 | Brister et al. |
| 8,290,560 B2 | 10/2012 | Kamath et al. |
| 8,366,614 B2 | 2/2013 | Say et al. |
| 2001/0016682 A1 | 8/2001 | Berner et al. |
| 2001/0020546 A1 | 9/2001 | Eldridge et al. |
| 2001/0041830 A1 | 11/2001 | Varalli et al. |
| 2001/0051766 A1 | 12/2001 | Gazdzinski |
| 2001/0051768 A1 | 12/2001 | Schulman et al. |
| 2002/0019022 A1 | 2/2002 | Dunn et al. |
| 2002/0022883 A1 | 2/2002 | Burg |
| 2002/0023852 A1 | 2/2002 | McIvor et al. |
| 2002/0026111 A1 | 2/2002 | Ackerman |
| 2002/0032531 A1 | 3/2002 | Mansky et al. |
| 2002/0042090 A1 | 4/2002 | Heller et al. |
| 2002/0042561 A1 | 4/2002 | Schulman et al. |
| 2002/0045808 A1 | 4/2002 | Ford et al. |
| 2002/0055673 A1 | 5/2002 | Van Antwerp et al. |
| 2002/0065453 A1 | 5/2002 | Lesho et al. |
| 2002/0068860 A1 | 6/2002 | Clark, Jr. |
| 2002/0084196 A1 | 7/2002 | Liamos et al. |
| 2002/0099282 A1 | 7/2002 | Knobbe et al. |
| 2002/0099997 A1 | 7/2002 | Piret |
| 2002/0100725 A1 | 8/2002 | Lee et al. |
| 2002/0111547 A1 | 8/2002 | Knobbe et al. |
| 2002/0119711 A1 | 8/2002 | Van Antwerp et al. |
| 2002/0128546 A1 | 9/2002 | Silver |
| 2002/0137991 A1 | 9/2002 | Scarantino et al. |
| 2002/0151796 A1 | 10/2002 | Koulik |
| 2002/0151816 A1 | 10/2002 | Rich et al. |
| 2002/0155615 A1 | 10/2002 | Novikov et al. |
| 2002/0161288 A1* | 10/2002 | Shin et al. .................. 600/316 |
| 2002/0169369 A1 | 11/2002 | Ward et al. |
| 2002/0177763 A1 | 11/2002 | Burns et al. |
| 2002/0182241 A1 | 12/2002 | Borenstein et al. |
| 2002/0185384 A1 | 12/2002 | Leong et al. |
| 2002/0188185 A1 | 12/2002 | Sohrab |
| 2002/0188216 A1 | 12/2002 | Kayyali et al. |
| 2002/0193885 A1 | 12/2002 | Legeay et al. |
| 2002/0198513 A1 | 12/2002 | Lebel et al. |
| 2003/0004457 A1 | 1/2003 | Andersson |
| 2003/0006669 A1 | 1/2003 | Pei et al. |
| 2003/0023171 A1 | 1/2003 | Sato et al. |
| 2003/0023317 A1 | 1/2003 | Brauker et al. |
| 2003/0028089 A1 | 2/2003 | Galley et al. |
| 2003/0032874 A1 | 2/2003 | Rhodes et al. |
| 2003/0050546 A1 | 3/2003 | Desai et al. |
| 2003/0070548 A1 | 4/2003 | Clausen |
| 2003/0076082 A1 | 4/2003 | Morgan et al. |
| 2003/0078481 A1 | 4/2003 | McIvor et al. |
| 2003/0078560 A1 | 4/2003 | Miller et al. |
| 2003/0097082 A1 | 5/2003 | Purdy et al. |
| 2003/0100821 A1 | 5/2003 | Heller et al. |
| 2003/0125612 A1 | 7/2003 | Fox et al. |
| 2003/0125613 A1 | 7/2003 | Enegren et al. |
| 2003/0130616 A1 | 7/2003 | Steil et al. |
| 2003/0132227 A1 | 7/2003 | Geisler et al. |
| 2003/0134347 A1 | 7/2003 | Heller et al. |
| 2003/0181794 A1 | 9/2003 | Rini et al. |
| 2003/0186457 A1 | 10/2003 | Iwaki et al. |
| 2003/0187338 A1 | 10/2003 | Say et al. |
| 2003/0188427 A1 | 10/2003 | Say et al. |
| 2003/0199745 A1 | 10/2003 | Burson et al. |
| 2003/0199878 A1 | 10/2003 | Pohjonen et al. |
| 2003/0203498 A1 | 10/2003 | Neel et al. |
| 2003/0211625 A1 | 11/2003 | Cohan et al. |
| 2003/0212317 A1 | 11/2003 | Kovatchev et al. |
| 2003/0212346 A1 | 11/2003 | Yuzhakov et al. |
| 2003/0212347 A1 | 11/2003 | Sohrab |
| 2003/0225361 A1 | 12/2003 | Sabra |
| 2003/0225437 A1 | 12/2003 | Ferguson |
| 2003/0235817 A1 | 12/2003 | Bartkowiak et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0024327 A1 | 2/2004 | Brodnick |
| 2004/0030285 A1 | 2/2004 | Lavi et al. |
| 2004/0039298 A1 | 2/2004 | Abreu |
| 2004/0045879 A1 | 3/2004 | Shults et al. |
| 2004/0052689 A1 | 3/2004 | Yao |
| 2004/0064156 A1 | 4/2004 | Shah et al. |
| 2004/0068230 A1 | 4/2004 | Estes et al. |
| 2004/0074785 A1 | 4/2004 | Holker et al. |
| 2004/0078219 A1 | 4/2004 | Kaylor |
| 2004/0087671 A1 | 5/2004 | Tamada et al. |
| 2004/0106857 A1 | 6/2004 | Gough |
| 2004/0106859 A1 | 6/2004 | Say et al. |
| 2004/0120848 A1 | 6/2004 | Teodorczyk |
| 2004/0133164 A1 | 7/2004 | Funderburk et al. |
| 2004/0143173 A1 | 7/2004 | Reghabi et al. |
| 2004/0152187 A1 | 8/2004 | Haight et al. |
| 2004/0152622 A1 | 8/2004 | Keith et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0186362 A1 | 9/2004 | Brauker et al. |
| 2004/0199059 A1 | 10/2004 | Brauker et al. |
| 2004/0236200 A1 | 11/2004 | Say et al. |
| 2004/0236251 A1 | 11/2004 | Roe et al. |
| 2004/0242982 A1 | 12/2004 | Sakata et al. |
| 2004/0254433 A1 | 12/2004 | Bandis et al. |
| 2005/0006122 A1 | 1/2005 | Burnette |
| 2005/0010265 A1 | 1/2005 | Baru Fassio et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0096519 A1 | 5/2005 | DeNuzzio et al. |
| 2005/0112169 A1 | 5/2005 | Brauker et al. |
| 2005/0113653 A1 | 5/2005 | Fox et al. |
| 2005/0115832 A1 | 6/2005 | Simpson et al. |
| 2005/0121322 A1 | 6/2005 | Say et al. |
| 2005/0139489 A1 | 6/2005 | Davies et al. |
| 2005/0143635 A1 | 6/2005 | Kamath et al. |
| 2005/0143636 A1 | 6/2005 | Zhang et al. |
| 2005/0143675 A1 | 6/2005 | Neel et al. |
| 2005/0154271 A1 | 7/2005 | Rasdal et al. |
| 2005/0173245 A1 | 8/2005 | Feldman et al. |
| 2005/0187720 A1 | 8/2005 | Goode et al. |
| 2005/0192557 A1 | 9/2005 | Brauker et al. |
| 2005/0203360 A1 | 9/2005 | Brauker et al. |
| 2005/0211571 A1 | 9/2005 | Schulein et al. |
| 2005/0215871 A1 | 9/2005 | Feldman et al. |
| 2005/0215872 A1 | 9/2005 | Berner et al. |
| 2005/0239154 A1 | 10/2005 | Feldman et al. |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0261563 A1 | 11/2005 | Zhou et al. |
| 2006/0008370 A1 | 1/2006 | Massaro et al. |
| 2006/0015020 A1 | 1/2006 | Neale et al. |
| 2006/0015024 A1 | 1/2006 | Brister et al. |

(56) References Cited

U.S. PATENT DOCUMENTS

| | | |
|---|---|---|
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0047215 A1 | 3/2006 | Newman et al. |
| 2006/0100588 A1 | 5/2006 | Brunnberg et al. |
| 2006/0183984 A1 | 8/2006 | Dobbles et al. |
| 2006/0183985 A1 | 8/2006 | Brister et al. |
| 2006/0222566 A1 | 10/2006 | Brauker et al. |
| 2006/0258929 A1 | 11/2006 | Goode et al. |
| 2007/0016381 A1 | 1/2007 | Kamath et al. |
| 2007/0032706 A1 | 2/2007 | Kamath et al. |
| 2007/0049873 A1 | 3/2007 | Hansen et al. |
| 2007/0066873 A1 | 3/2007 | Kamath et al. |
| 2007/0073129 A1 | 3/2007 | Shah et al. |
| 2007/0203410 A1 | 8/2007 | Say et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213610 A1 | 9/2007 | Say et al. |
| 2008/0021666 A1 | 1/2008 | Goode et al. |
| 2008/0033254 A1 | 2/2008 | Kamath et al. |
| 2008/0033268 A1 | 2/2008 | Stafford |
| 2008/0183061 A1 | 7/2008 | Goode et al. |
| 2008/0183399 A1 | 7/2008 | Goode et al. |
| 2008/0189051 A1 | 8/2008 | Goode et al. |
| 2008/0193936 A1 | 8/2008 | Squirrell |
| 2008/0194936 A1 | 8/2008 | Goode et al. |
| 2008/0194937 A1 | 8/2008 | Goode et al. |
| 2008/0195967 A1 | 8/2008 | Goode et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0306368 A1 | 12/2008 | Goode et al. |
| 2008/0306433 A1 | 12/2008 | Dobbles et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode et al. |
| 2009/0036758 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0062645 A1 | 3/2009 | Brauker et al. |
| 2009/0076361 A1 | 3/2009 | Kamath et al. |
| 2009/0124877 A1 | 5/2009 | Goode, Jr. et al. |
| 2009/0124878 A1 | 5/2009 | Goode, Jr. et al. |
| 2009/0156924 A1 | 6/2009 | Shariati et al. |
| 2009/0182217 A1 | 7/2009 | Li et al. |
| 2009/0187090 A1 | 7/2009 | Say et al. |
| 2009/0187091 A1 | 7/2009 | Say et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2010/0069728 A1 | 3/2010 | Funderburk et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0212583 A1 | 8/2010 | Brister et al. |
| 2011/0178378 A1 | 7/2011 | Brister et al. |
| 2011/0190614 A1 | 8/2011 | Brister et al. |
| 2011/0290645 A1 | 12/2011 | Brister et al. |
| 2012/0277562 A1 | 11/2012 | Brister et al. |

FOREIGN PATENT DOCUMENTS

| | | |
|---|---|---|
| EP | 0 320 109 | 6/1989 |
| EP | 0 353 328 | 2/1990 |
| EP | 0 390 390 | 10/1990 |
| EP | 0 563 795 | 10/1993 |
| EP | 0 561 966 | 10/1994 |
| EP | 0 286 118 | 1/1995 |
| EP | 0 776 628 | 6/1997 |
| EP | 0 817 809 | 1/1998 |
| EP | 0 838 230 | 4/1998 |
| EP | 0 880 936 | 12/1998 |
| EP | 0 885 932 | 12/1998 |
| EP | 1 077 634 | 2/2001 |
| EP | 1 078 258 | 2/2001 |
| EP | 1 077 636 | 1/2004 |
| FR | 2656423 | 6/1991 |
| FR | 2760962 | 9/1998 |
| GB | 1 442 303 | 7/1976 |
| GB | 2149918 | 6/1985 |
| WO | WO 89/02720 | 4/1989 |
| WO | WO 90/10861 | 9/1990 |
| WO | WO 90/13021 | 11/1990 |
| WO | WO 92/07525 | 5/1992 |
| WO | WO 92/10584 | 6/1992 |
| WO | WO 92/13271 | 8/1992 |
| WO | WO 93/14693 | 8/1993 |
| WO | WO 93/19701 | 10/1993 |
| WO | WO 94/22367 | 10/1994 |
| WO | WO 95/02357 | 1/1995 |
| WO | WO 95/07109 | 3/1995 |
| WO | WO 96/01611 | 1/1996 |
| WO | WO 96/14026 | 5/1996 |
| WO | WO 96/25088 | 8/1996 |
| WO | WO 96/25089 | 8/1996 |
| WO | WO 96/32076 | 10/1996 |
| WO | WO 96/36296 | 11/1996 |
| WO | WO 97/01986 | 1/1997 |
| WO | WO 97/17884 | 5/1997 |
| WO | WO 97/28737 | 8/1997 |
| WO | WO 98/01071 | 1/1998 |
| WO | WO 98/24358 | 6/1998 |
| WO | WO 98/33549 | 8/1998 |
| WO | WO 98/42249 | 10/1998 |
| WO | WO 98/56293 | 12/1998 |
| WO | WO 99/56613 | 4/1999 |
| WO | WO 99/33504 | 7/1999 |
| WO | WO 99/48419 | 9/1999 |
| WO | WO 99/58051 | 11/1999 |
| WO | WO 99/58973 | 11/1999 |
| WO | WO 00/19887 | 4/2000 |
| WO | WO 00/32098 | 6/2000 |
| WO | WO 00/33065 | 6/2000 |
| WO | WO 00/49940 | 8/2000 |
| WO | WO 00/49941 | 8/2000 |
| WO | WO 00/49942 | 8/2000 |
| WO | WO 00/59373 | 10/2000 |
| WO | WO 00/74753 | 12/2000 |
| WO | WO 01/12158 | 2/2001 |
| WO | WO 01/20019 | 3/2001 |
| WO | WO 01/20334 | 3/2001 |
| WO | WO 01/34243 | 5/2001 |

(56) References Cited

FOREIGN PATENT DOCUMENTS

| | | |
|---|---|---|
| WO | WO 01/43660 | 6/2001 |
| WO | WO 01/52727 | 7/2001 |
| WO | WO 01/52935 | 7/2001 |
| WO | WO 01/58348 | 8/2001 |
| WO | WO 01/64105 | 9/2001 |
| WO | WO 01/68901 | 9/2001 |
| WO | WO 01/69222 | 9/2001 |
| WO | WO 01/73109 | 10/2001 |
| WO | WO 01/88524 | 11/2001 |
| WO | WO 01/88534 | 11/2001 |
| WO | WO 02/24065 | 3/2002 |
| WO | WO 02/058537 | 8/2002 |
| WO | WO 02/082989 | 10/2002 |
| WO | WO 02/100266 | 12/2002 |
| WO | WO 03/094714 | 11/2003 |
| WO | WO 03/097866 | 11/2003 |
| WO | WO 2004/030726 | 4/2004 |
| WO | WO 2004/052190 | 6/2004 |
| WO | WO 2004/060455 | 7/2004 |
| WO | WO 2004/098685 | 11/2004 |
| WO | WO 2005/012873 | 2/2005 |
| WO | WO 2005/018443 | 3/2005 |
| WO | WO 2005/057168 | 6/2005 |
| WO | WO 2005/057175 | 6/2005 |
| WO | WO 2005/026689 | 10/2005 |
| WO | WO 2006/105146 | 10/2006 |
| WO | WO 2008/028644 | 3/2008 |
| WO | WO 2008/069931 | 6/2008 |
| WO | WO 2008/079616 | 7/2008 |
| WO | WO 2008/101217 | 8/2008 |
| WO | WO 2008/138006 | 11/2008 |

OTHER PUBLICATIONS

Aalders et al. 1991. Development of a wearable glucose sensor; studies in healthy volunteers and in diabetic patients. The International Journal of Artificial Organs 14(2):102-108.

Abe et al. 1992. Characterization of glucose microsensors for intracellular measurements. Anal. Chem. 64(18):2160-2163.

Abel et al. 1984. Experience with an implantable glucose sensor as a prerequisite of an artificial beta cell, Biomed. Biochim. Acta 43(5):577-584.

Abel et al. 2002. Biosensors for in vivo glucose measurement: can we cross the experimental stage. Biosens Bioelectron 17:1059-1070.

Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers. com Nov. 7, 2006 http://www. Answers.com/topic/xenogenic.

Armour et al. Dec. 1990. Application of Chronic Intravascular Blood Glucose Sensor in Dogs. Diabetes 39:1519-1526.

Asberg et al. 2003. Hydrogels of a Conducting Conjugated Polymer as 3-D Enzyme Electrode. Biosensors Bioelectronics. pp. 199-207.

Atanasov et al. 1994. Biosensor for continuous glucose monitoring. Biotechnology and Bioengineering 43:262-266.

Atanasov et al. 1997. Implantation of a refillable glucose monitoring-telemetry device. Biosens Bioelectron 12:669-680.

Aussedat et al. 1997. A user-friendly method for calibrating a subcutaneous glucose sensor-based hypoglycaemic alarm. Biosensors & Bioelectronics 12(11):1061-1071.

Bailey et al. 2007. Reduction in hemoglobin A1c with real-time continuous glucose monitoring: results from a 12-week observational study. Diabetes Technology & Therapeutics 9(3):203-210.

Baker et al. 1993. Dynamic concentration challenges for biosensor characterization. Biosensors & Bioelectronics 8:433-441.

Baker et al. 1996. Dynamic delay and maximal dynamic error in continuous biosensors. Anal Chem 68(8):1292-1297.

Bani Amer, M. M. 2002. An accurate amperometric glucose sensor based glucometer with eliminated cross-sensitivity. J Med Eng Technol 26(5):208-213.

Beach et al. 1999. Subminiature implantable potentiostat and modified commercial telemetry device for remote glucose monitoring. IEEE Transactions on Instrumentation and Measurement 48(6):12391245.

Bellucci et al. Jan. 1986. Electrochemical behaviour of graphite-epoxy composite materials (GECM) in aqueous salt solutions, Journal of Applied Electrochemistry, 16(1):15-22.

Bessman et al., Progress toward a glucose sensor for the artificial pancreas, Proceedings of a Workshop on Ion-Selective Microelectrodes, Jun. 4-5, 1973, Boston, MA, 189-197.

Biermann et al. 2008. How would patients behave if they were continually informed of their blood glucose levels? A simulation study using a "virtual" patient. Diab. Thechnol. & Therapeut., 10:178-187.

Bindra et al. 1989. Pulsed amperometric detection of glucose in biological fluids at a surface-modified gold electrode. Anal Chem 61:2566-2570.

Bindra et al. 1991. Design and in Vitro Studies of a Needle-Type Glucose Senso for Subcutaneous Monitoring. Anal. Chem 63:1692-96.

Bisenberger et al. 1995. A triple-step potential waveform at enzyme multisensors with thick-film gold electrodes for detection of glucose and sucrose. Sensors and Actuators, B 28:181-189.

Bland et al. 1986. Statistical methods for assessing agreement between two methods of clinical measurement. Lancet 1:307-310.

Bland et al. 1990. a note on the use of the intraclass correlation coefficient in the evaluation of agreement between two methods of measurement. Comput. Biol. Med. 20(5):337-340.

Bobbioni-Harsch et al. 1993. Lifespan of subcutaneous glucose sensors and their performances during dynamic glycaemia changes in rats, J. Biomed. Eng. 15:457-463.

Bode et al. 1999. Continuous glucose monitoring used to adjust diabetes therapy improves glycosylated hemoglobin: a pilot study. Diabetes Research and Clinical Practice 46:183-190.

Bode et al. 2000. Using the continuous glucose monitoring system to improve the management of type 1 diabetes. Diabetes Technology & Therapeutics, 2(Suppl 1):S43-48.

Bode, B. W. 2000. Clinical utility of the continuous glucose monitoring system. Diabetes Technol Ther, 2(Suppl 1):S35-41.

Boedeker Plastics, Inc. 2009. Polyethylene Specifications Data Sheet, http://www.boedeker.com/polye_p.htm [Aug. 19, 2009 3:36:33 PM].

Boland et al. 2001. Limitations of conventional methods of self-monitoring of blood glucose. Diabetes Care 24(11):1858-1862.

Bolinder et al. 1992. Microdialysis measurement of the absolute glucose concentration in subcutaneous adipose tissue allowing glucose monitoring in diabetic patients. Diabetologia 35:1177-1180.

Bolinder et al. 1997. Self-monitoring of blood glucose in type 1 diabetic patients: Comparison with continuous microdialysis measurements of glucose in subcutaneous adipose tissue during ordinary life conditions. Diabetes Care 20(1):64-70.

Bott, A. W. 1997. A Comparison of Cyclic Voltammetry and Cyclic Staircase Voltammetry Current Separations 16:1, 23-26.

Bott, a. 1998. Electrochemical methods for the determination of glucose. Current Separations 17(1):25-31.

Bowman, L.; Meindl, J. D. 1986. The packaging of implantable integrated sensors. IEEE Trans Biomed Eng BME33(2):248-255.

Brauker et al. Jun. 27, 1996. Local Inflammatory Response Around Diffusion Chambers Containing Xenografts Transplantation 61(12):1671-1677.

Brauker et al. 1998. Sustained expression of high levels of human factor IX from human cells implanted within an immunoisolation device into athymic rodents. Hum Gene Ther 9:879-888.

Braunwald, 2008. Biomarkers in heart failure. *N. Engl. J. Med.*, 358:2148-2159.

Bremer et al. 1999. Is blood glucose predictable from previous values? a solicitation for data. Diabetes 48:445-451.

(56) References Cited

OTHER PUBLICATIONS

Bremer et al. 2001. Benchmark data from the literature for evaluation of new glucose sensing technologies. Diabetes Technology & Therapeutics 3(3):409-418.
Brooks et al. "Development of an on-line glucose sensor for fermentation monitoring," Biosensors, 3:45-56 (1987/88).
Bruckel et al. 1989. In vivo measurement of subcutaneous glucose concentrations with an enzymatic glucose sensor and a wick method. Klin Wochenschr 67:491-495.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Candas et al (1994). "An adaptive plasma glucose controller based on a nonlinear insulin/glucose model." *IEEE Transactions on Biomedical Engineering*, 41(2): 116-124.
Cass et al. "Ferrocene-mediated enzyme electrodes for amperometric determination of glucose," Anal. Chem., 36:667-71 (1984).
Cassidy et al., Apr. 1993. Novel electrochemical device for the detection of cholesterol or glucose, Analyst, 118:415-418.
Chase et al. 2001. Continuous subcutaneous glucose monitoring in children with type 1 diabetes. Pediatrics 107:222-226.
Chen et al. 2002. Defining the period of recovery of the glucose concentration after its local perturbation by the implantation of a miniature sensor. Clin. Chem. Lab. Med. 40:786-789.
Chia et al. 2004. Glucose sensors: toward closed loop insulin delivery. Endocrinol Metab Clin North Am 33:175-95.
Choleau et al. 2002. Calibration of a subcutaneous amperometric glucose sensor implanted for 7 days in diabetic patients. Part 1. Effect of measurement uncertainties on the determination of sensor sensitivity and background curent. Biosensors and Bioel.
Choleau et al. 2002. Calibration of a subcutaneous amperometric glucose sensor implanted for 7 days in diabetic patients. Part 2. Superiority of the one-point calibration method. Biosensors and Bioelectronics 17:647-654.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-impintable, ferrocene-mediated glucose sensor. J. Biomed. Eng. 8:272-274.
Clark et al., 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csöregi et al. 1994. Amperometric microbiosensors for detection of hydrogen peroxide and glucose based on peroxidase-modified carbon fibers. Electroanalysis 6:925-933.
Csoregi et al., 1994. Design, characterization, and one-point in vivo calibration of a subcutaneously implanted glucose electrode. Anal Chem. 66(19):3131-3138.
Dai et al. 1999. Hydrogel Membranes with Mesh Size Asymmetry Based on the Gradient Crosslink of Poly(vinyl alcohol). Journal of Membrane Science 156:67-79.

Danielsson et al. 1988. Enzyme thermistors, Methods in Enzymology, 137:181-197.
D'Arrigo et al. 2003. Porous-Si based bioreactors for glucose monitoring and drugs production. Proc. of SPIE 4982:178-184.
Dassau et al., In silico evaluation platform for artifical pancreatic β-cell development-a dynamic simulator for closed loop control with hardware-in-the-loop, Diabetes Technology & Therapeutics, 11(3):1-8, 2009.
Davies, et al. 1992. Polymer membranes in clinical sensor applications. I. An overview of membrane function, Biomaterials, 13(14):971-978.
Davis et al. 1983. Bioelectrochemical fuel cell and sensor based on a quinoprotein, alcohol dehydrogenase. *Enzyme Microb. Technol.*, vol. 5, Sep., 383-388.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont' Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8: 121-129.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
Ei-Sa'ad et al. 1990. Moisture Absorption by Epoxy Resins: the Reverse Thermal Effect. Journal of Materials Science 25:3577-3582.
Ernst et al. 2002. Reliable glucose monitoring through the use of microsystem technology. Anal. Bioanal. Chem. 373:758-761.
Fabietti et al. 2007. Clinical validation of a new control-oriented model of insulin and glucose dynamcs in subjects with type 1 diabetes, Diabetes Technology & Therapeutics, 9(4):327-338.
Fahy et al., an analysis: hyperglycemic intensive care patients need continuous glocuse monitoring--easier said than done, Journal of Diabetese Science and Technology, 2(2):201-204, Mar. 2008.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.
Fischer et al. 1995. Hypoglycaemia-warning by means of subcutaneous electrochemical glucose sensors: an animal study, Horm. Metab. Rese. 27:53.
Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Frost et al. 2002. Implantable chemical sensors for real-time clinical monitoring: Progress and challenges. Current Opinion in Chemical Biology 6:633-641.
Gabbay et al. 2008. Optical coherence tomography-based continuous noninvasive glucose monitoring in patients with diabetes. Diab. Thechnol. & Therapeut., 10:188-193.
Ganesan et al., Gold layer-based dual crosslinking procedure of glucose oxidase with ferrocene monocarboxylic acid provides a stable biosensor, Analytical Biochemistry 343:188-191, 2005.
Ganesh et al., Evaluation of the VIA@ blood chemistry monitor for glucose in healthy and diabetic volunteers, Journal of Diabetese Science and Technology, 2(2):182-193, Mar. 2008.

(56) References Cited

OTHER PUBLICATIONS

Garg et al. 1999. Correlation of fingerstick blood glucose measurements with GlucoWatch biographer glucose results in young subjects with type 1 diabetes. Diabetes Care 22(10):1708-1714.
Garg et al. 2004. Improved Glucose Excursions Using an Implantable Real-Time continuous Glucose Sensor in Adults with Type I Diabetes. Diabetes Care 27:734-738.
Geller et al. 1997. Use of an immunoisolation device for cell transplantation and tumor immunotherapy. Ann NY Acad Sci 831:438-451.
Gerritsen et al. 1999. Performance of subcutaneously implanted glucose sensors for continuous monitoring. The Netherlands Journal of Medicine 54:167-179.
Gerritsen et al. 2001. Influence of inflammatory cells and serum on the performance of implantable glucose sensors. J Biomed Mater Res 54:69-75.
Gerritsen, M. 2000. Problems associated with subcutaneously implanted glucose sensors. Diabetes Care 23(2):143-145.
Gilligan et al. 1994. Evaluation of a subcutaneous glucose sensor out to 3 months in a dog model. Diabetes Care 17(8):882-887.
Gilligan et al. 2004, Feasibility of continuous long-term glucose monitoring from a subcutaneous glucose sensor in humans. Diabetes Technol Ther 6:378-386.
Godsland et al. 2001. Maximizing the Success Rate of Minimal Model Insulin Sensitivity Measurement in Humans: the Importance of Basal Glucose Levels. The Biochemical Society and the Medical Research Society, 1-9.
Gouda et al., Jul. 4, 2003. Thermal inactivation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gregg et al. 1990. Cross-Linked Redox Gels Containing Glucose Oxidase for Amperometric Biosensor Applications. Anal. Chem. 62:258-263.
Gross et al. 2000. Efficacy and reliability of the continuous glucose monitoring system. Diabetes Technology & Therapeutics, 2(Suppl 1):519-26.
Gross et al. 2000. Performance evaluation of the MiniMed® continuous glucose monitoring system during patient home use. Diabetes Technology & Therapeutics 2(1):49-56.
Guerci et al., Clinical performance of CGMS in type 1 diabetic patents treated by continuous subcutaneous insulin infusion using insulin analogs, Diabetes Care, 26:582-589, 2003.
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hamilton Syringe Selection Guide. 2006. Syringe Selection. www.hamiltoncompany.com.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes C.*
Heise et al. 2003. Hypoglycemia warning signal and glucose sensors: Requirements and concepts. Diabetes Technology & Therapeutics 5:563-571.

Heller, "Electrical wiring of redox enzymes," *Acc. Chem. Res.*, 23:128-134 (1990).
Heller, A. 1992. Electrical Connection of Enzyme Redox Centers to Electrodes. J. Phys. Chem. 96:3579-3587.
Heller, A. 1999. Implanted electrochemical glucose sensors for the management of diabetes. Annu Rev Biomed Eng 1:153-175.
Heller, A. 2003. Plugging metal connectors into enzymes. Nat Biotechnol 21:631-2.
Hicks, 1985. In Situ Monitoring, Clinical Chemistry, 31(12):1931-1935.
Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.
Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Anal Chem 75:3308-3315.
http://www.merriam-webster.com/dictionary, definition for "aberrant," Aug. 19, 2008, p. 1.
Hu, et al. 1993. A needle-type enzyme-based lactate sensor for in vivo monitoring, Analytica Chimica Acta, 281:503-511.
Huang et al. A 0.5mV passive telemetry IC for biomedical applications. Swiss Federal Institute of Technology. 4 pp.
Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.
Hunter et al. 2000. Minimally Invasive Glucose Sensor and Insulin Delivery System. MIT Home Automation and Healthcare Consortium. Progress Report No. 25.
Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.
Jablecki et al. 2000. Simulations of the frequency response of implantable glucose sensors. Analytical Chemistry 72:1853-1859.
Jaremko et al. 1998. Advances toward the implantable artificial pancreas for treatment of diabetes. Diabetes Care 21(3):444-450.
Jensen et al. 1997. Fast wave forms for pulsed electrochemical detection of glucose by incorporation of reductive desorption of oxidation products. Analytical Chemistry 69(9):1776-1781.
Jeutter, D. C. 1982. A transcutaneous implanted battery recharging and biotelemeter power switching system. IEEE Trans Biomed Eng 29:314-321.
Johnson (1991). "Reproducible electrodeposition of biomolecules for the fabrication of miniature electroenzymatic biosensors," *Sensors and Actuators B*, 5:85-89.
Johnson et al. 1992. In vivo evaluation of an electroenzymatic glucose sensor implanted in subcutaneous tissue. Biosensors & Bioelectronics, 7:709-714.
Jovanovic, L. 2000. The role of continuous glucose monitoring in gestational diabetes mellitus. Diabetes Technology & Therapeutics, 2 Suppl 1, S67-71.
Kacaniklic May-Jun. 1994. Electroanalysis, 6(5-6):381-390.
Kamath et al. Calibration of a continuous glucose monitor: effect of glucose rate of change, Eighth Annual Diabetes Technology Meeting, Nov. 13-15 2008, p. A88.
Kang et al. 2003. In vitro and short-term in vivo characteristics of a Kel-F thin film modified glucose sensor. Anal Sci 19:1481-1486.
Kargol et al. 2001. Studies on the structural properties of porous membranes: measurement of linear dimensions of solutes. Biophys Chem 91:263-271.
Kaufman. 2000. Role of the continuous glucose monitoring system in pediatric patients. Diabetes Technology & Therapeutics 2(1):S-49—S-52.
Kaufman et al. 2001. A pilot study of the continuous glucose monitoring system. Diabetes Care 24(12):2030-2034.
Kawagoe et al. 1991. Enzyme-modified organic conducting salt microelectrode, Anal. Chem. 63:2961-2965.
Keedy et al. 1991. Determination of urate in undiluted whole blood by enzyme electrode. *Biosensors & Bioelectronics*, 6: 491-499.

(56) References Cited

OTHER PUBLICATIONS

Kerner et al. 1988. A potentially implantable enzyme electrode for amperometric measurement of glucose, Horm Metab Res Suppl. 20:8-13.

Kerner et al. "The function of a hydrogen peroxide-detecting electroenzymatic glucose electrode is markedly impaired in human sub-cutaneous tissue and plasma," Biosensors & Bioelectronics, 8:473-482 (1993).

Kerner, W. 2001. Implantable glucose sensors: Present status and future developments. Exp. Clin. Endocrinol. Diabetes 109(Suppl 2):5341-346.

Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.

Ko, Wen H. 1985. Implantable Sensors for Closed-Loop Prosthetic Systems, Futura Pub. Co., Inc., Mt. Kisco, NY, Chapter 15:197-210.

Kondo et al. 1982. A miniature glucose sensor, implantable in the blood stream. Diabetes Care. 5(3):218-221.

Koschinsky et al. 1988. New approach to technical and clinical evaluation of devices for self- monitoring of blood glucose. Diabetes Care 11(8): 619-619.

Koschinsky et al. 2001. Sensors for glucose monitoring: Technical and clinical aspects. Diabetes Metab. Res. Rev. 17:113-123.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kraver et al. 2001. A mixed-signal sensor interface microinstrument. Sensors and Actuators A 91:266-277.

Krouwer, J. S. 2002. Setting performance goals and evaluating total analytical error for diagnostic assays. Clinical Chemistry 48(6):919-927.

Kruger et al. 2000. Psychological motivation and patient education: A role for continuous glucose monitoring. Diabetes Technology & Therapeutics, 2(Suppl 1):593-97.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kurnik et al. 1999. Application of the mixtures of experts algorithm for signal processing in a noninvasive glucose monitoring system. Sensors and Actuators B, 60:19-26.

Kurtz et al. 2005. Recommendations for blood pressure measurement in humans and experimental animals, Part 2: Blood pressure measurement in experimental animals, A statement for professionals from the subcommittee of professional and public education of.

LaCourse et al. 1993. Optimization of waveforms for pulsed amperometric detection of carbohydrates based on pulsed voltammetry. Analytical Chemistry 65:50-52.

Ladd et al., Structure Determination by X-ray Crystallography, 3rd ed. Plenum, 1996, Ch. 1, pp. xxi-xxiv and 1-58.

Lee et al. 1999. Effects of pore size, void volume, and pore connectivity on tissue responses. Society for Biomaterials 25th Annual Meeting, 171.

Lehmann et al. May 1994. Retrospective valication of a physiological model of glucose-iunsulin interaaction in tyhpe 1 diabetes mellitus, Med. Eng. Phys. 16:193-202.

Lerner et al. 1984. An implantable electrochemical glucose sensor. Ann. N.Y. Acad. Sci. 428:263-278.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Lohn et al., A knowledge-based system for real-time validation of calibrations and measurements, Chemometrics and Intelligent Laboratory Systems, 1999 46, 57-66.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lyandres et al. (2008). Progress toward an in vivo surface-enhanced raman spectroscopy glucose sensor. *Diabetes Technology & Therapeutics*, 10(4): 257-265.

Lynch et al. 2001. Estimation-based model predictive control of blood glucose in type I diabetics: A simulation study. Proceedings of the IEEE 27th Annual Northeast Bioengineering Conference, pp. 79-80.

Lynn, P. A. 1971. Recursive digital filters for biological signals. Med. & Biol. Engng. 9:37-43.

Maidan et al. 1992. Elimination of Electrooxidizable Interferent-Produced Currents in Amperometric Biosensors, Analytical Chemistry, 64:2889-2896.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Mancy et al. 1962. A galvanic cell oxygen analyzer. Journal of Electroanalytical Chemistry 4:65-92.

Maran et al. 2002. Continuous subcutaneous glucose monitoring in diabetic patients: A multicenter analysis. Diabetes Care 25(2):347-352.

Mar., W. F. 2002. Dealing with the delay. Diabetes Technol Ther 4(1):49-50.

Marena et al. 1993. The artifical endocrine pancreas in clinical practice and research. Panminerva Medica 35(2):67-74.

Martin, R. F. 2000. General Deming regression for estimating systematic bias and its confidence interval in method-comparison studies. *Clinical Chemistry*, 46(1):100-104.

Mascini et al. 1989. Glucose electrochemical probe with extended linearity for whole blood. *J Pharm Biomed Anal* 7(12): 1507-1512.

Mastrototaro et al. "An electroenzymatic glucose sensor fabricated on a flexible substrate," Sensors and Actuators B, 5:139-44 (1991).

Mastrototaro, J. J. 2000. The MiniMed continuous glucose monitoring system. Diabetes Technol Ther 2(Suppl 1):513-8.

Mastrototaro et al. 2003. Reproducibility of the continuous glucose monitoring system matches previous reports and the intended use of the product. Diabetes Care 26:256; author reply p. 257.

Matsumoto et al. 1998. A micro-planar amperometeric glucose sensor unsusceptible to interference species. Sensors and Actuators B 49:68-72.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profile analysis. Diab. Thechnol. & Therapeut., 10:149-159.

McCartney et al. 2001. Near-infrared fluorescence lifetime assay for serum glucose based on allophycocyanin-labeled concanavalin A. Anal Biochem 292:216-221.

McGrath et al. 1995. The use of differential measurements with a glucose biosensor for interference compensation during glucose determinations by flow injection analysis. Biosens Bioelectron 10:937-943.

McKean, et al. 7 Jul. 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

(56) References Cited

OTHER PUBLICATIONS

Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.
Merriam-Webster Online Dictionary. The term "nominal." http://www.m-w.com/dictionary/nominal.
Metzger et al. Jul. 2002. Reproducibility of glucose measurements using the glucose sensor. Diabetes Care 25(6):1185-1191.
Meyerhoff et al. 1992. On line continuous monitoring of subcutaneous tissue glucose in men by combining portable glucosensor with microdialysis. Diabetologia 35:1087-1092.
Miller et al. 1989. In vitro stimulation of fibroblast activity by factors generated from human monocytes activated by biomedical polymers. Journal of J Biomed Mater Res 23:911-930.
Miller et al. 1989. Generation of IL1-like activity in response to biomedical polymer implants: a comparison of in vitro and in vivo models. J Biomed Mater Res 23:1007-1026.
Miller, A. 1988. Human monocyte/macrophage activation and interleukin 1 generation by biomedical polymers. J Biomed Mater Res 23:713-731.
Moatti-Sirat et al. 1992. Evaluating in vitro and in vivo the interference of ascorbate and acetaminophen on glucose detection by a needle-type glucose sensor, Biosensors & Bioelectronics 7:345-352.
Moatti-Sirat et al. 1992. Towards continuous glucose monitoring: in vivo evaluation of a miniaturized glucose sensor implanted for several days in rat subcutaneous tissue. Diabetologia 35:224-230.
Moatti-Sirat et al., Reduction of acetaminophen interference in glucose sensors by a composite Nafion membrane: demonstration in rats and man, Diabetologia 37(6):610-616, Jun. 1994.
Monsod et al. 2002. Do sensor glucose levels accurately predict plasma glucose concentrations during hypoglycemia and hyperinsulinemia? Diabetes Care 25(5):889-893.
Morff et al. 1990. Microfabrication of reproducible, economical, electroenzymatic glucose sensors, Annual International Conference of the IEEE Engineering in Medicine and Biology Society, 12(2):0483-0484.
Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.
Moussy et al. 1994. A miniaturized Nafion-based glucose sensor: in vitro and in vivo evaluation in dogs. Int. J. Artif. Organs 17(2):88-94.
Mowery et al. 2000. Preparation and characterization of hydrophobic polymeric films that are thromboresistant via nitric oxide release. Biomaterials 21:9-21.
Murphy, et al. 1992. Polymer membranes in clinical sensor applications. Ii. The design and fabrication of permselective hydrogels for electrochemical devices, Biomaterials, 13(14):979-990.
Muslu. 1991. Trickling filter performance. Apllied Biochemistry and Biotechnology 37:211-224.
Nafion® 117 Solution Product Description, Product No. 70160, Sigma-Aldrich Corp., St. Louis, MO.
Nam et al. 2000. A novel fabrication method of macroporous biodegradable polymer scaffolds using gas foaming salt as a porogen additive. J Biomed Mater Res 53:1-7.
Neuburger et al. 1987. Pulsed amperometric detection of carbohydrates at gold electrodes with a two-step potential waveform. Anal. Chem. 59:150-154.
Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.
Ohara et al. 1994. "Wired" enzyme electrodes for amperometric determination of glucose or lactate in the presence of interfering substances. Anal Chem 66:2451-2457.

Okuda et al. 1971. Mutarotase effect on micro determinations of D-glucose and its anomers with β-D-glucose oxidase. Anal Biochem 43:312-315.
Oxford English Dictionary Online. Definition of "impending". http://www.askoxford.com/results/?view=dev dict&field-12668446 Impending&branch= Jan. 11, 2010.
Palmisano et al. 2000. Simultaneous monitoring of glucose and lactate by an interference and cross- talk free dual electrode amperometric biosensor based on electropolymerized thin films. Biosensors & Bioelectronics 15:531-539.
Panteleon et al. 2003. The role of the independent variable to glucose sensor calibration. Diabetes Technology & Therapeutics 5(3):401-410.
Parker et al. 1999. A model-based algorithm for blood glucose control in type I diabetic patients. IEEE Trans. Biomed. Eng. 46(2):148-157.
Patel et al. 2003. Amperometric glucose sensors based on ferrocene containing polymeric electron transfer systems-a preliminary report. Biosens Bioelectron 18:1073-6.
Peacock et al. 2008. Cardiac troponin and outcome in acute heart failure. N. Engl. J. Med., 358: 2117-2126.
Pfeiffer, E.F. 1990. The glucose sensor: the missing link in diabetes therapy, Horm Metab Res Suppl. 24:154-164.
Pfeiffer et al. 1992. On line continuous monitoring of subcutaneous tissue glucose is feasible by combining portable glucosensor with microdialysis. Horm. Metab. Res. 25:121-124.
Pichert et al. 2000. Issues for the coming age of continuous glucose monitoring Diabetes Educ 26(6):969-980.
Pickup et al. "Implantable glucose sensors: choosing the appropriate sensing strategy," Biosensors, 3:335-346 (1987/88).
Pickup et al. "In vivo molecular sensing in diabetes mellitus: an implantable glucose sensor with direct electron transfer," Diabetologia, 32:213-217 (1989).
Pickup et al. 1989. Potentially-implantable, amperometric glucose sensors with mediated electron transfer: improving the operating stability. Biosensors 4:109-119.
Pickup et al. 1993. Responses and Calibration of Amperometric Glucose Sensors Implanted in the Subcutaneous Tissue of Man. ACTA Diabetol, pp. 143-148.
Pickup et al. 1993. Developing glucose sensors for *in vivo* use. Elsevier Science Publishers Ltd (UK), TIBTECH vol. 11: 285-291.
Pinner et al., Cross-linking of cellulose acetate by ionizing radiation, Nature, vol. 184, 1303-1304, Oct. 24, 1959.
Pishko et al. "Amperometric glucose microelectrodes prepared through immobilization of glucose oxidase in redox hydrogels," Anal. Chem., 63:2268-72 (1991).
Pitzer et al. 2001. Detection of hypoglycemia with the GlucoWatch biographer. Diabetes Care 24(5):881-885.
Poirier et al. 1998. Clinical and statistical evaluation of self-monitoring blood glucose meters. Diabetes Care 21(11):1919-1924.
Poitout, et al. 1991. In Vitro and in Vivo Evaluation in Dogs of a Miniaturized Glucose Sensor, ASAIO Transactions, 37:M298-M300.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode, Electrochimica Acta 26(6):725-729.
Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Ratner, B.D. 2002. Reducing capsular thickness and enhancing angiogenesis around implant drug release systems. J Control Release 78:211-218.

(56) References Cited

OTHER PUBLICATIONS

Reach et al. 1992. Can continuous glucose monitoring be used for the treatment of diabetes? Analytical Chemistry 64(5):381-386.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Rebrin et al. "Automated feedback control of subcutaneous glucose concentration in diabetic dogs," Diabetologia, 32:573-76 (1989).
Rebrin et al. 1992. Subcutaenous glucose monitoring by means of electrochemical sensors: fiction or reality? J. Biomed. Eng. 14:33-40.
Rebrin et al. 1999. Subcutaneous glucose predicts plasma glucose independent of insulin: Implications for continuous monitoring. Am. J. Physiol. 277:E561-71.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rhodes et al. 1994. Prediction of pocket-portable and implantable glucose enzyme electrode performance from combined species permeability and digital simulation analysis. Analytical Chemistry 66(9):1520-1529.
Rigla et al. 2008. Real-time continuous glucose monitoring together with telemedical assitance improves glycemic control and glucose stability in pump-treated patients. Diab. Thechnol. & Therapeut., 10:194-199.
Rinken et al. 1998. Calibration of glucose biosensors by using presteady state kinetic data. Biosensors & Bioelectronics, 13:801-807.
Rivers et al., Central venous oxygen saturation monitoring in the critically ill patient, Current Opinion in Critical Care, 7:204-211, 2001.
Sakakida et al. 1992. Development of Ferrocene-Mediated Needle-Type Glucose Sensor as a Measure of True Subcutaneous Tissue Glucose Concentrations. Artif. Organs Today 2(2):145-158.
Sakakida et al. 1993. Ferrocene-Mediated Needle Type Glucose Sensor Covered with Newly Designed Biocompatible Membran, Sensors and Actuators B 13-14:319-322.
Salardi et al. 2002. the glucose area under the profiles obtained with continuous glucose monitoring system relationships with HbA1c in pediatric type 1 diabetic patients. Diabetes Care 25(10):1840-1844.
San Diego Plastics, Inc. 2009. Polyethylene Data Sheet, http://www.sdplastics.com/polyeth.html.
Sansen et al. 1985. "Glucose sensor with telemetry system." in Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidt et al. 1993. Glucose concentration in subcutaneous extracellular space. Diabetes Care 16(5):695-700.
Schmidtke et al. 1998. Accuracy of the one-point in vivo calibration of "wired" glucose oxidase electrodes implanted in jugular veins of rats in periods of rapid rise and decline of the glucose concentration. Anal Chem 70:2149-2155.
Schmidtke et al., Measurement and modeling of the transient difference between blood and subcutaneous glucose concentrations in the rat after injection of insulin. *Proc Natl Aced Sci U S A* 1998, 95,294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Service et al. 1970. Mean amplitude of glycemic excursions, a measure of diabetic instability. Diabetes, 19: 644-655.
Service et al. 1987. Measurements of glucose control. Diabetes Care, 10: 225-237.

Service, R. F. 2002. Can sensors make a home in the body? Science 297:962-3.
Sharkawy et al. 1996. Engineering the tissue which encapsulates subcutaneous implants. I. Diffusion properties, J Biomed Mater Res, 37:401-412.
Shaw et al. "In vitro testing of a simply constructed, highly stable glucose sensor suitable for implantation in diabetic patients," Biosensors & Bioelectronics, 6:401-406 (1991).
Shichiri et al. 1982. Wearable artificial endocrine pancrease with needle-type glucose sensor. Lancet 2:1129-1131.
Shichiri et al. 1983. Glycaemic Control in Pancreatectomized Dogs with a Wearable Artificial Endocrine Pancreas. Diabetologia 24:179-184.
Shichiri et al. 1985. Needle-type Glucose Sensor for Wearable Artificial Endocrine Pancreas in Implantable Sensors 197-210.
Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.
Shichiri et al. 1989. Membrane Design for Extending the Long-Life of an Implantable Glucose Sensor. Diab. Nutr. Metab. 2:309-313.
Shults et al. 1994. A telemetry-instrumentation system for monitoring multiple subcutaneously implanted glucose sensors. IEEE Transactions on Biomedical Engineering 41(10):937-942.
Sieminski et al. 2000. Biomaterial-microvasculature interactions. Biomaterials 21:2233-2241.
Skyler, J. S. 2000. The economic burden of diabetes and the benefits of improved glycemic control: the potential role of a continuous glucose monitoring system. Diabetes Technology & Therapeutics 2 Suppl 1:S7-12.
Slater-Maclean et al. 2008. Accuracy of glycemic measurements in the critically ill. Diab. Thechnol. & Therapeut., 10:169-177.
Sokol et al. 1980, Immobilized-enzyme rate-determination method for glucose analysis, Clin. Chem. 26(1):89-92.
Sokolov et al. 1995. Metrological opportunities of the dynamic mode of operating an enzyme amperometric biosensor. Med. Eng. Phys. 17(6):471-476.
Sproule et al. 2002. Fuzzy pharmacology: Theory and applications. Trends in Pharmacological Sciences, 23(9):412-417.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sternberg et al. 1988. Study and Development of Multilayer Needle-type Enzyme-based Glucose Microsensors. Biosensors 4:27-40.
Sternberg et al. 1996. Does fall in tissue glucose precede fall in blood glucose? Diabetologia 39:609- 612.
Street et al. 1988. A note on computing robust regression estimates via iteratively reweighted least squares. The American Statistician 42(2):152-154.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrane Science, 75(93-105).
Tanenberg et al. 2000. Continuous glucose monitoring system: a new approach to the diagnosis of diabetic gastroparesis. Diabetes Technology & Therapeutics, 2 Suppl 1:S73-80.
Tang et al. 1993. Fibrin(ogen) mediates acute inflammatory responses to biomaterials. J Exp Med 178:2147-2156.
Tang et al. 1995. Inflammatory responses to biomaterials. Am J Clin Pathol 103:466-471.
Tang et al. 1996. Molecular determinants of acute inflammatory responses to biomaterials. J Clin Invest 97:1329-1334.
Tang et al. 1998. Mast cells mediate acute inflammatory responses to implanted biomaterials. Proc Natl Acad Sci U S a 95:8841-8846.

(56) References Cited

OTHER PUBLICATIONS

Tatsuma et al. 1991. Oxidase/peroxidase bilayer-modified electrodes as sensors for lactate, pyruvate, cholesteral and uric acid, Analytica Chimica Acta, 242:85-89.
Thome et al. 1995. -Abstract—Can the decrease in subcutaneous glucose concentration precede the decrease in blod glucose level? Proposition for a push-pull kinetics hypothesis, Horm. Metab. Res. 27:53.
Thomé -Duret et al. 1996. Modification of the sensitivity of glucose sensor implanted into subcutaneous tissue. Diabetes Metabolism, 22:174-178.
Thome-Duret et al. 1996. Use of a subcutaneous glucose sensor to detect decreases in glucose concentration prior to observation in blood, Anal. Chem. 68:3822-3826.
Thomé -Duret et al. 1998. Continuous glucose monitoring in the free-moving rat. Metabolism, 47:799-803.
Thompson et al., In Vivo Probes: Problems and Perspectives, Department of Chemistry, University of Toronto, Canada, pp. 255-261, 1986.
Tibell et al. 2001. Survival of macroencapsulated allogeneic parathyroid tissue one year after transplantation in nonimmunosuppressed humans. Cell Transplant 10:591-9.
Tierney et al. 2000. Effect of acetaminophen on the accuracy of glucose measurements obtained with the GlucoWatch biographer. Diabetes Technol Ther 2:199-207.
Tierney et al. 2000. The GlucoWatch® biographer: a frequent, automatic and noninvasive glucose monitor. Ann. Med. 32:632-641.
Tilbury et al. 2000. Receiver operating characteristic analysis for intelligent medical systems—A new approach for finding confidence intervals. IEEE Transactions on Biomedical Engineering 47(7):952-963.
Torjman et al., Glucose monitoring in acute care: technologies on the horizon, Journal of Deabetes Science and Technology, 2(2):178-181, Mar. 2008.
Trajanoski et al. 1998. Neural predictive controller for insulin delivery using the subcutaneous route. IEEE Transactions on Biomedical Engineering 45(9):1122-1134.
Trecroci, D. 2002. A Glimpse into the Future- Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.
Turner and Pickup, "Diabetes mellitus: biosensors for research and management," *Biosensors*, 1:85-115 (1985).
Unger et al. 2004. Glucose control in the hospitalized patient. Emerg Med 36(9):12-18.
Updike et al. 1967. The enzyme electrode. Nature, 214:986-988.
Updike et al. 1979. Continuous glucose monitor based on an immobilized enzyme electrode detector. J Lab Clin Med, 93(4):518-527.
Updike et al. 1982. Implanting the glucose enzyme electrode: Problems, progress, and alternative solutions. Diabetes Care, 5(3):207-212.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons,.
Updike et al. 2000. A subcutaneous glucose sensor with improved longevity, dynamic range, and stability of calibration. Diabetes Care 23(2):208-214.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.
Vadgama. 1988. Diffusion limited enzyme electrodes. NATO ASI Series: Series C, Math and Phys. Sci. 226:359-377.
Van den Berghe 2004. Tight blood glucose control with insulin in "real-life" intensive care. Mayo Clin Proc 79(8):977-978.
Velho et al. 1989. in vitro and in vivo stability of electrode potentials in needle-type glucose sensors. Influence of needle material. Diabetes 38:164-171.
Velho et al. 1989. Strategies for calibrating a subcutaneous glucose sensor. Biomed Biochim Acta 48(11/12):957-964.
von Woedtke et al. 1989. In situ calibration of implanted electrochemical glucose sensors. Biomed Biochim. Acta 48(11/12):943-952.
Wade Jr., L.G. Organic Chemistry, Chapter 17, Reactions of Aromatic Compounds pp. 762-763, 1987.
Wagner et al. 1998. Continuous amperometric monitoring of glucose in a brittle diabetic chimpanzee with a miniature subcutaneous electrode. Proc. Natl. Acad. Sci. A, 95:6379-6382.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 1999. Assessment of chronically implanted subcutaneous glucose sensors in dogs: The effect of surrounding fluid masses. ASAIO Journal, 45:555-561.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2000. Rise in background current over time in a subcutaneous glucose sensor in the rabbit: Relevance to calibration and accuracy. Biosensors & Bioelectronics, 15:53-61.
Ward et al. 2002. A new amperometric glucose microsensor: in vitro and short-term in vivo evaluation. Biosensors & Bioelectronics, 17:181-189.
Wientjes, K. J. C. 2000. Development of a glucose sensor for diabetic patients (Ph.D. Thesis).
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilkins et al. 1995. Glucose monitoring: state of the art and future possibilities. Med Eng Phys 18:273-288.
Wilkins et al. 1995. Integrated implantable device for long-term glucose monitoring. Biosens. Bioelectron 10:485-494.
Wilson et al. 1992. Progress toward the development of an implantable sensor for glucose. Clin. Chem. 38(9):1613-1617.
Wilson et al. 2000. Enzyme-based biosensors for in vivo measurements. Chem. Rev., 100:2693-2704.
Wood, W. et al. Mar. 1990. Hermetic Sealing with Epoxy. Mechanical Engineering 1-3.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.
Wu et al. 1999. In situ electrochemical oxygen generation with an immunoisolation device. Annals New York Academy of Sciences, pp. 105-125.
Yamasaki, Yoshimitsu. Sep. 1984. The development of a needle-type glucose sensor for wearable artificial endocrine pancreas. Medical Journal of Osaka University 35(1-2):25-34.
Yamasaki et al. 1989. Direct measurement of whole blood glucose by a needle-type sensor. Clinica Chimica Acta. 93:93-98.
Yang et al (1996). "A glucose biosensor based on an oxygen electrode: In-vitro performances in a model buffer solution and in blood plasma," Biomedical Instrumentation & Technology, 30:55-61.

(56) References Cited

OTHER PUBLICATIONS

Yang et al. 1998. Development of needle-type glucose sensor with high selectivity. Science and Actuators B 46:249-256.
Yang, et al. 2004. A Comparison of Physical Properties and Fuel Cell Performance of Nafion and Zirconium Phosphate/Nafion Composite Membranes. Journal of Membrane Science 237:145-161.
Ye et al. 1993. High Current Density 'Wired' Quinoprotein Glucose Dehydrogenase Electrode. Anal. Chem. 65:238-241.
Zamzow et al. 1990. Development and evaluation of a wearable blood glucose monitor, ASAIO Transactions; 36(3): pp. M588-M591.
Zavalkoff et al. 2002. Evaluation of conventional blood glucose monitoring as an indicator of integrated glucose values using a continuous subcutaneous sensor. Diabetes Care 25(9):1603-1606.
Zethelius et al. 2008. Use of multiple biomarkers to improve the prediction of death from cardiovascular causes. N. Engl. J. Med., 358: 2107-2116.
Zhang et al (1993). Electrochemical oxidation of $H_2 O_2$ on Pt and Pt + Ir electrodes in physiological buffer and its applicability to $H_2 O_2$-based biosensors. *J. Electroanal. Chem.*, 345:253-271.
Zhang et al. 1994. Elimination of the acetaminophen interference in an implantable glucose sensor. Analytical Chemistry 66(7):1183-1188.
Zhu et al. (1994). "Fabrication and characterization of glucose sensors based on a microarray $H_2 O_2$ electrode." Biosensors & Bioelectronics, 9: 295-300.
Zhu et al. 2002. Planar amperometric glucose sensor based on glucose oxidase immobilized by chitosan film on prussian blue layer. Sensors, 2:127-136.
IPRP for PCT/US05/024993 filed Jul. 13, 2005.
ISR and WO for PCT/US05/024993 filed Jul. 13, 2005.
Office Action dated Sep. 30, 2002 in U.S. App. No. 09/636,369.
Office Action dated Jul. 15, 2008 in U.S. App. No. 10/633,367.
Office Action dated Jun. 11, 2009 in U.S. Appl. No. 10/633,367.
Office Action dated Jul. 30, 2009 in U.S. Appl. No. 12/102,654.
Office Action dated Dec. 23, 2008 in U.S. Appl. No. 12/102,745.
Office Action dated Oct. 20, 2004 in U.S. Appl. No. 10/632,537.
Office Action dated Dec. 21, 2004 in U.S. Appl. No. 10/632,537.
Office Action dated May 29, 2008 in U.S. Appl. No. 95/001,039.
Office Action dated May 19, 2009 in U.S. App. No. 11/038,340.
Office Action dated Nov. 9, 2009 in U.S. Appl. No. 11/038,340.
Office Action dated Jun. 17, 2008 in U.S. Appl. No. 11/038,340.
Office Action dated Jan. 5, 2009 in U.S. Appl. No. 11/038,340.
Office Action dated Feb. 12, 2007 in U.S. Appl. No. 10/633,404.
Office Action dated Jun. 17, 2008 in U.S. Appl. No. 95/001,038.
Office Action dated Oct. 5, 2006 in U.S. Appl. No. 10/633,329.
Office Action dated Mar. 26, 2007 in U.S. Appl. No. 10/633,329.
Office Action dated Jul. 30, 2007 in U.S. Appl. No. 10/633,329.
Office Action dated Feb. 4, 2008 in U.S. Appl. No. 10/633,329.
Office Action dated Jun. 12, 2008 in U.S. Appl. No. 10/633,329.
Office Action dated Dec. 18, 2008 in U.S. Appl. No. 10/633,329.
Office Action dated Jun. 11, 2009 in U.S. Appl. No. 10/633,329.
Office Action dated Jun. 23, 2009 in U.S. Appl. No. 10/648,849.
Office Action dated Jun. 24, 2008 n. U.S. Appl. No. 11/007,920.
Office Action dated Nov. 28, 2007 in U.S. Appl. No. 10/991,966.
Office Action dated Jul. 22, 2008 in U.S. Appl. No. 10/991,966.
Office Action dated Nov. 27, 2006 in U.S. Appl. No. 10/789,359.
Office Action dated Mar. 20, 2008 in U.S. Appl. No. 10/789,359.
Office Action dated Oct. 3, 2008 in U.S. Appl. No. 10/789,359.
Office Action mailed Jun. 5, 2008 in U.S. Appl. No. 10/838,909.
Office Action mailed Mar. 16, 2009 in U.S. Appl. No. 10/838,909.
Office Action dated Mar. 31, 2008 in U.S. Appl. No. 11/077,759.
Office Action dated Jul. 10, 2008 in U.S. Appl. No. 11/077,759.
Office Action dated May 26, 2009 in U.S. Appl. No. 11/077,759.
Office Action dated Jul. 21, 2009 in U.S. Appl. No. 11/077,739.
Office Action dated Jun. 1, 2007 in U.S. Appl. No. 11/077,740.
Office Action dated Nov. 1, 2007 in U.S. Appl. No. 11/077,740.
Office Action dated Feb. 7, 2008 in U.S. Appl. No. 11/077,740.
Office Action dated Jul. 25, 2008 in U.S. Appl. No. 11/077,740.
Office Action dated Apr. 28, 2009 in U.S. Appl. No. 11/077,740.
Office Action dated Jan. 23, 2009 in U.S. Appl. No. 11/077,765.
Office Action dated Jan. 10, 2008 in U.S. Appl. No. 11/077,714.
Office Action dated Jun. 26, 2008 in U.S. Appl. No. 11/157,365.
Office Action dated Jan. 7, 2009 in U.S. Appl. No. 11/157,365.
Office Action dated Jul. 21, 2009 in U.S. Appl. No. 11/157,365.
Office Action dated Oct. 4, 2006 in U.S. Appl. No. 11/334,876.
Office Action dated Sep. 25, 2007 in U.S. Appl. No. 11/334,876.
Office Action dated May 2, 2008 in U.S. Appl. No. 11/334,876.
Office Action dated Aug. 26, 2008 in U.S. Appl. No. 11/334,876.
Office Action dated Aug. 25, 2009 in U.S. Appl. No. 11/334,876.
Office Action dated Jun. 30, 2008 in U.S. Appl. No. 11/360,252.
Office Action dated Jan. 29, 2009, in U.S. Appl. No. 11/360,252.
Office Action dated Jul. 23, 2009, in U.S. Appl. No. 11/360,252.
Office Action dated Aug. 11, 2008 in U.S. Appl. No. 11/360,819.
Office Action dated Dec. 26, 2008 in U.S. Appl. No. 11/360,819.
Office Action dated Oct. 29, 2009 in U.S. Appl. No. 11/360,819.
Ciba® Irgacure® 2959 Photoinitiator, Product Description. Apr. 2, 1998. Ciba Specialty Chemicals Inc., Basel, Switzerland. 3 pages. [corrected cite].
Choleau et al. 2002. Calibration of a subcutaneous amperometric glucose sensor implanted for 7 days in diabetic patients. Part 1. Effect of measurement uncertainties on the determination of sensor sensitivity and background current. Biosensors and Bioelectronics 17:641-646.. [corrected cite].
Direct 30/30® Blood Glucose Sensor, (Markwell Medical) Catalog, ©1990, ELCO Diagnostics Company. 1 page. [corrected cite].
DuPont Dimension AR. 1998. The chemistry analyzer that makes the most of your time, money and effort. Catalog. Dade International, Chemistry Systems. Newark, DE. 18 pages.. [corrected cite].
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes Care*, 17(5): 387-396. . [corrected cite].
Huang et al. Aug. 1975. Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode. U.S. Department of Commerce/NTIS, pp. 1-116.. [corrected cite].
Huang et al., Sep. 1997, a 0.5mW Passive Telemetry IC for Biomedical Applications, Proceedings of the 23rd European Solid-State Circuits Conference (ESSCIRC '97), pp. 172-175, Southampton, UK. [corrected cite].
Hunter et al. Mar. 31, 2000. Minimally Invasive Glucose Sensor and Insulin Delivery System. MIT Home Automation and Healthcare Consortium. Progress Report No. 2-5. 17 pages. . [corrected cite].
Merriam-Webster Online Dictionary. Apr. 23, 2007. Definition of "nominal". http://www.merriam-websterconn/dictionary/nominal [corrected cite].
Nafion® 117 Solution Product Description, Product No. 70160, Sigma-Aldrich Corp., St. Louis, MO. Downloaded from https://www.signaaldrich.com/cgi-bin/hsrun/Suite7/Suite/HAHTpage/Suite.HsExternal Prod . . . on Apr. 7, 2005. [corrected cite].
Bergveld et al., "Fabrication-and Mass Production," Advances in Biosensors, Supplement 1 (1993) Chapter 6; 165-186.
Reach et al., "Clinical Needs for in Vivo Monitoring," Advances in Biosensors, Supplement 1 (1993) Chapter 1; 7-28.
Shichiri et al., "In Vivo Characteristics of Needle-Type Glucose Sensor—Measurements of Subcutaneous Glucose Concentrations in Human Volunteers," Implantable Glucose Sensors—The State of the Art, Hormone and Metabolic Research Supplement Series vol. No. 20 (1988) 17-20.
European Extended Search Report dated Aug. 3, 2011 for Application No. EP 10195520.1, filed Jul. 13, 2005; 6 pages.
European Office Action dated Jul. 19, 2012 for Application No. EP 10195520.1, filed Jul. 13, 2005; 4 pages.
European Response/Claims to Office Action filed Jan. 16, 2013 for Application No. EP 10195520.1, filed Jul. 13, 2005; 7 pages.
Request for Ex Parte Reexamination filed Apr. 29, 2011 for U.S. Appl. No. 11/077,693, filed Mar. 10, 2005 (USP 7,713,574), 4 pgs.

(56) References Cited

OTHER PUBLICATIONS

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.

Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310.

Kusano, H. Glucose enzyme electrode with percutaneous interface which operates independently of dissolved oxygen. Clin Phys Physiol Meas. 1989. 10(1): 1-9.

European Office Action dated Dec. 15, 2011 in EP 10195496.4, filed Jul. 13, 2005.

European Response filed Jun. 22, 2012 in EP 10195496.4, filed Jul. 13, 2005.

Japanese Office Action dated May 22, 2012 for Application No. 2011-121598, filed Jul. 13, 2005.

Notice of Opposition dated Jul. 25, 2012 in European Patent No. 1986543, granted Dec. 14, 2011.

Office Action dated Jan. 20, 2012 for U.S. Appl. No. 12/359,207, filed Jan. 23, 2009.

Request for Ex Parte Reexamination dated Sep. 13, 2012 for U.S. Appl. No. 11/077,763, filed Mar. 10, 2005 (U.S. Appl. No. 7,310,544), 3 pgs.

Request for Inter Partes Reexamination dated Sep. 14, 2012 for U.S. Appl. No. 11/077,693, filed Mar. 10, 2005 (U.S. Appl. No. 7,713,574), 4 pgs.

Request for Inter Partes Reexamination dated Sep. 14, 2012 for U.S. Appl. No. 7,713,574, issued Jun. 5, 2012; TOC. pp. 3.

\* cited by examiner

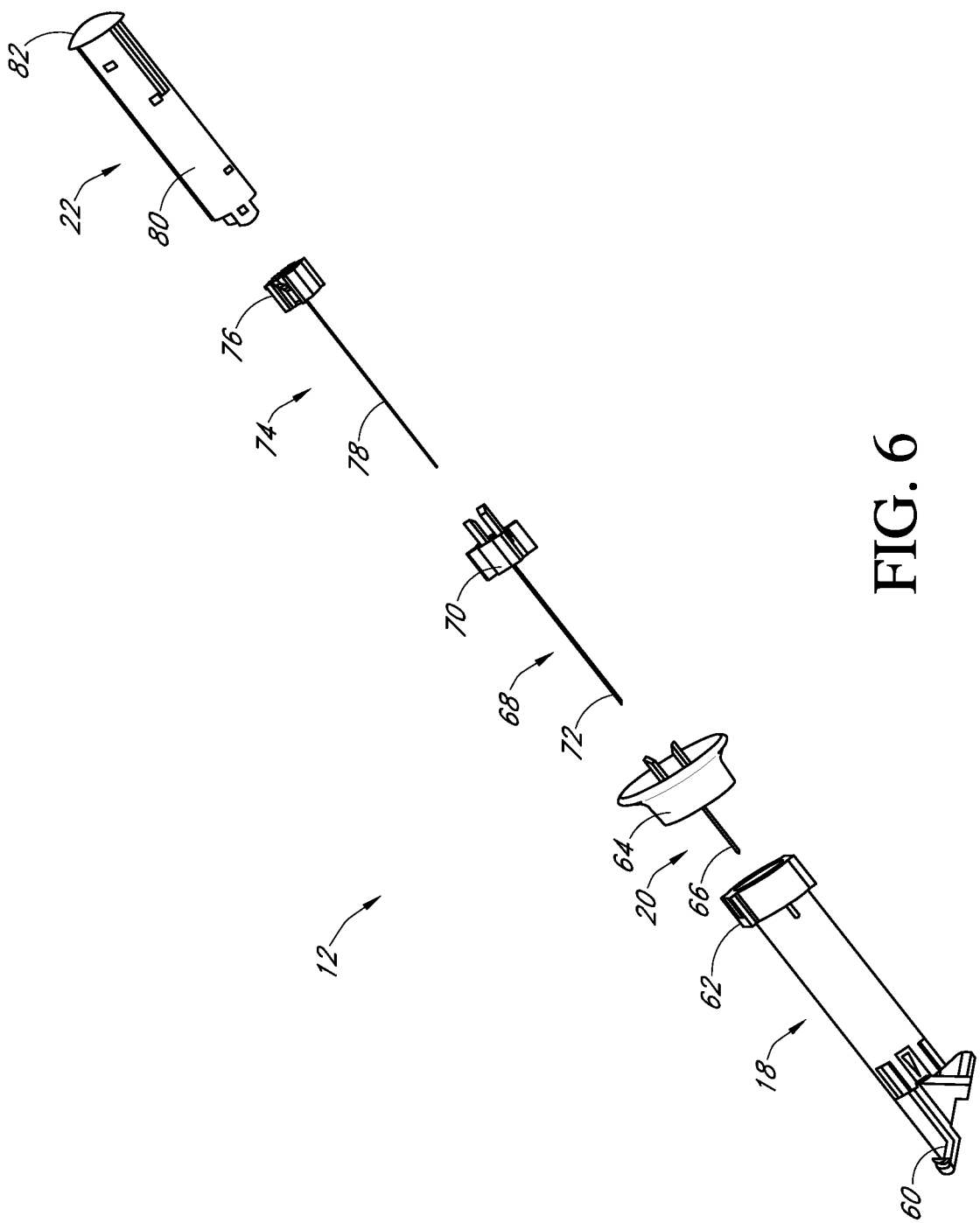

TRANSCUTANEOUS ANALYTE SENSOR

CROSS-REFERENCE TO RELATED APPLICATIONS

This application is a continuation of U.S. application Ser. No. 11/077,765 filed Mar. 10, 2005, which claims the benefit of U.S. Provisional Application No. 60/587,787 filed Jul. 13, 2004; U.S. Provisional Application No. 60/587,800 filed Jul. 13, 2004; U.S. Provisional Application No. 60/614,683 filed Sep. 30, 2004; and U.S. Provisional Application No. 60/614,764 filed Sep. 30, 2004. The contents of each of the aforementioned applications are incorporated by reference herein in its entirety, and are hereby made a part of this specification.

FIELD OF THE INVENTION

The present invention relates generally to systems and methods for measuring an analyte in a host. More particularly, the present invention relates to systems and methods for transcutaneous measurement of glucose in a host.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional method. This inhibits the ability to make educated insulin therapy decisions.

SUMMARY OF THE INVENTION

In a first aspect, a method for self-diagnosis of a continuous analyte sensor is provided, the method comprising: receiving a stream of sensor data from a continuous analyte sensor, the stream comprising at least one sensor data point; converting the sensor data into calibrated data using a conversion function; performing a self-diagnostic test on the sensor data or the calibrated data; and setting a mode of operation of the continuous analyte sensor.

In an embodiment of the first aspect, the step of performing a self-diagnostic test comprises evaluating a rate of change of the calibrated data or a rate of change of the sensor data.

In an embodiment of the first aspect, the step of performing a self-diagnostic test comprises evaluating a rate of acceleration of the calibrated data or a rate of acceleration of the sensor data.

In an embodiment of the first aspect, the step of performing a self-diagnostic test comprises predicting future sensor data or future calibrated data, and comparing the predicted data with time-corresponding measured data.

In an embodiment of the first aspect, the step of performing a self-diagnostic test comprises detecting a shift in a baseline of the sensor data or a shift in a baseline of the calibrated data.

In an embodiment of the first aspect, the step of performing a self-diagnostic test comprises detecting a shift in a sensitivity of the continuous analyte sensor.

In an embodiment of the first aspect, the step of setting a mode of operation comprises setting a mode selected from the group consisting of a start-up mode, a normal mode, and a suspended mode.

In an embodiment of the first aspect, the start-up mode is set in response to a sensor initialization.

In an embodiment of the first aspect, the start-up mode is set in response to a result of the self-diagnostic test.

In an embodiment of the first aspect, the step of setting the mode of operation comprises setting the sensor to a start-up mode, wherein the start-up mode comprises determining a conversion function.

In an embodiment of the first aspect, the step of setting the mode of operation comprises setting a normal mode after a start-up mode determines a conversion function.

In an embodiment of the first aspect, the step of setting the mode of operation comprises setting a normal mode in response to a result of the self-diagnostic test.

In an embodiment of the first aspect, the step of setting the mode of operation comprises setting a normal mode, wherein the normal mode comprises continuously converting and displaying sensor data.

In an embodiment of the first aspect, the step of setting the mode of operation comprises setting a suspended mode after a reference analyte value has not been received for a predetermined time period.

In an embodiment of the first aspect, the step of setting the mode of operation comprises setting a suspended mode in response to a result of the self-diagnostic test.

In an embodiment of the first aspect, the step of setting the mode of operation comprises setting the sensor to suspended mode, wherein the suspended mode comprises suspending a continuous conversion or a display of sensor data.

In a second aspect, a method for processing continuous analyte sensor data from an analyte sensor is provided, the method comprising: continuously displaying calibrated analyte sensor data from an analyte sensor; receiving additional sensor data from the continuous analyte sensor, the sensor data comprising at least one sensor data point; and performing a self-diagnostic test on the sensor data point to diagnose an inaccuracy within the sensor or an inaccuracy within the sensor data.

In an embodiment of the second aspect, the method further comprises altering a continuous display of the calibrated analyte sensor data in response to a diagnosis of the self-diagnostic test.

In an embodiment of the second aspect, the step of altering a continuous display comprises suspending a display of calibrated data in response to a diagnosis of inaccuracy.

In an embodiment of the second aspect, altering a continuous display comprises requesting reference analyte data from a host.

In a third aspect, a system for initializing a continuous analyte sensor is provided, the system comprising: a sensor data module operatively linked to a continuous analyte sensor and configured to receive at least one sensor data point from the sensor; a processor module operatively linked with the sensor data module and programmed to calibrate sensor data; and a fail-safe module operatively linked with the processor module and programmed to diagnose an inaccuracy within the sensor or an inaccuracy within the sensor data.

In an embodiment of the third aspect, the system further comprises an interface control module configured to output information reflective of the sensor data, wherein the fail-safe module is configured to alter an output of information in response to a diagnosis of an inaccuracy.

BRIEF DESCRIPTION OF THE DRAWINGS

FIG. 6 is an exploded side view of an applicator, showing the components that facilitate sensor insertion and subsequent needle retraction.

DETAILED DESCRIPTION OF THE PREFERRED EMBODIMENT

Figure 1:
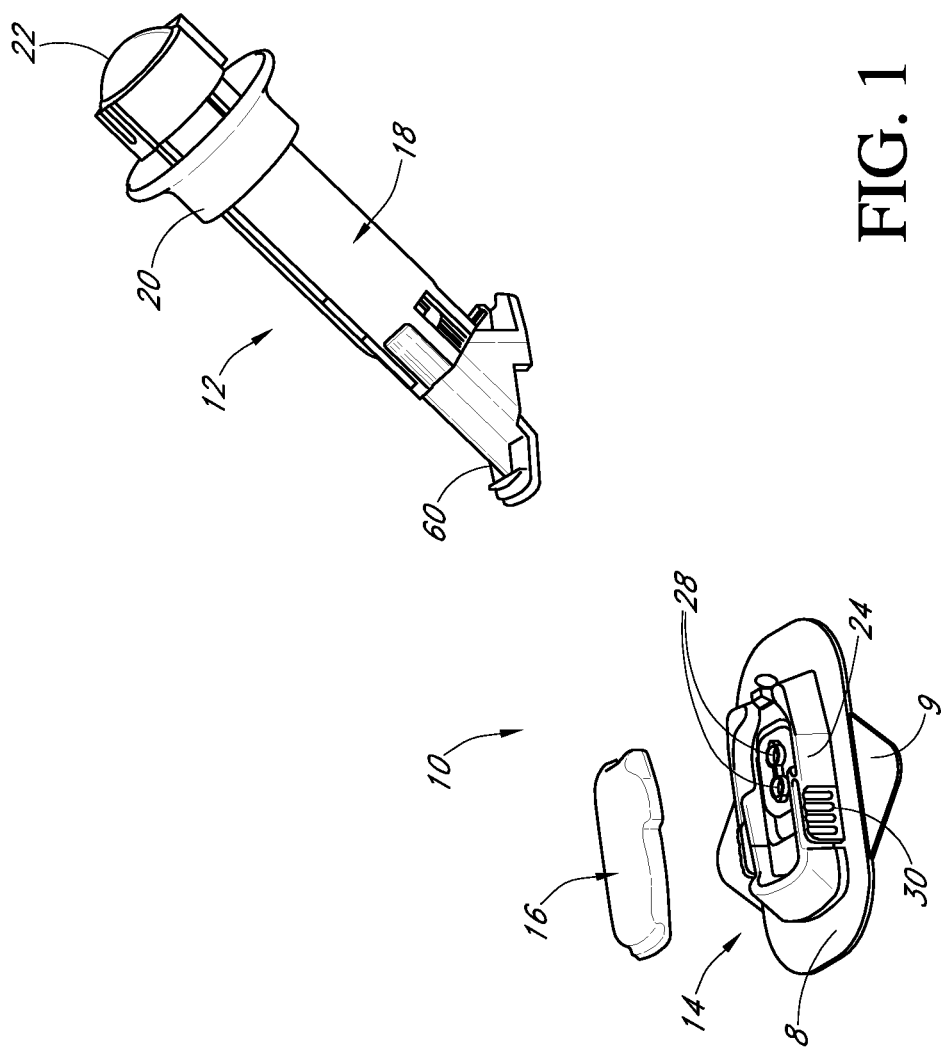
FIG. 1 is a perspective view of a transcutaneous analyte sensor system, including an applicator, a mounting unit, and an electronics unit.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

DEFINITIONS

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S. hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenyloin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidum, Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The term "host" as used herein is a broad term and is used in its ordinary sense, including, without limitation, to refer to mammals, particularly humans.

The term "exit-site" as used herein is a broad term and is used in its ordinary sense, including, without limitation, to refer to the area where a medical device (for example, a sensor and/or needle) exits from the host's body.

The phrase "continuous (or continual) analyte sensing" as used herein is a broad term and is used in its ordinary sense, including, without limitation, to refer to the period in which monitoring of analyte concentration is continuously, continually, and or intermittently (regularly or irregularly) performed, for example, about every 5 to 10 minutes.

The term "electrochemically reactive surface" as used herein is a broad term and is used in its ordinary sense, including, without limitation, to refer to the surface of an electrode where an electrochemical reaction takes place. For example, a working electrode measures hydrogen peroxide produced by the enzyme-catalyzed reaction of the analyte detected, which reacts to create an electric current. Glucose analyte can be detected utilizing glucose oxidase, which produces $H_2O_2$ as a byproduct. $H_2O_2$ reacts with the surface of the working electrode, producing two protons ($2H^+$), two electrons ($2e^-$) and one molecule of oxygen ($O_2$), which produces the electronic current being detected.

The term "electronic connection" as used herein is a broad term and is used in its ordinary sense, including, without limitation, to refer to any electronic connection known to those in the art that can be utilized to interface the sensing region electrodes with the electronic circuitry of a device, such as mechanical (for example, pin and socket) or soldered electronic connections.

The term "interferant" and "interferants," as used herein, are broad terms and are used in their ordinary sense, including, without limitation, to refer to species that interfere with the measurement of an analyte of interest in a sensor to produce a signal that does not accurately represent the analyte measurement. In one example of an electrochemical sensor, interferants are compounds with oxidation potentials that overlap with the analyte to be measured.

The term "sensing region" as used herein is a broad term and is used in its ordinary sense, including, without limitation, to refer to the region of a monitoring device responsible for the detection of a particular analyte. The sensing region generally comprises a non-conductive body, a working electrode (anode), a reference electrode (optional), and/or a counter electrode (cathode) passing through and secured within the body forming electrochemically reactive surfaces on the body and an electronic connective means at another location on the body, and a multi-domain membrane affixed to the body and covering the electrochemically reactive surface.

The term "high oxygen solubility domain" as used herein is a broad term and is used in its ordinary sense, including, without limitation, to refer to a domain composed of a material that has higher oxygen solubility than aqueous media such that it concentrates oxygen from the biological fluid surrounding the membrane system. The domain can act as an oxygen reservoir during times of minimal oxygen need and has the capacity to provide, on demand, a higher oxygen gradient to facilitate oxygen transport across the membrane. Thus, the ability of the high oxygen solubility domain to supply a higher flux of oxygen to critical domains when needed can improve overall sensor function.

The term "domain" as used herein is a broad term and is used in its ordinary sense, including, without limitation, to refer to a region of the membrane system that can be a layer, a uniform or non-uniform gradient (for example, an anisotropic region of a membrane), or a portion of a membrane.

The phrase "distal to" as used herein is a broad term and is used in its ordinary sense, including, without limitation, the spatial relationship between various elements in comparison to a particular point of reference. In general, the term indicates an element is located relatively far from the reference point than another element.

The term "proximal to" as used herein is a broad term and is used in its ordinary sense, including, without limitation, the spatial relationship between various elements in comparison to a particular point of reference. In general, the term indicates an element is located relatively near to the reference point than another element.

The terms "in vivo portion" and "distal portion" as used herein are broad terms and are used in their ordinary sense, including, without limitation, to refer to the portion of the device (for example, a sensor) adapted for insertion into and/or existence within a living body of a host.

The terms "ex vivo portion" and "proximal portion" as used herein are broad terms and are used in their ordinary sense, including, without limitation, to refer to the portion of the device (for example, a sensor) adapted to remain and/or exist outside of a living body of a host.

The terms "raw data stream" and "data stream," as used herein, are broad terms and are used in their ordinary sense, including, without limitation, to refer to an analog or digital signal from the analyte sensor directly related to the measured analyte. For example, the raw data stream is digital data in "counts" converted by an A/D converter from an analog signal (for example, voltage or amps) representative of an analyte concentration. The terms broadly encompass a plurality of time spaced data points from a substantially continuous analyte sensor, each of which comprises individual measurements taken at time intervals ranging from fractions of a second up to, for example, 1, 2, or 5 minutes or longer.

The term "count," as used herein, is a broad term and is used in its ordinary sense, including, without limitation, to refer to a unit of measurement of a digital signal. For example, a raw data stream measured in counts is directly related to a voltage (for example, converted by an A/D converter), which is directly related to current from the working electrode.

The term "physiologically feasible," as used herein, is a broad term and is used in its ordinary sense, including, without limitation, to refer to one or more physiological parameters obtained from continuous studies of glucose data in humans and/or animals. For example, a maximal sustained rate of change of glucose in humans of about 4 to 6 mg/dL/min and a maximum acceleration of the rate of change of about 0.1 to 0.2 mg/dL/min/min are deemed physiologically feasible limits. Values outside of these limits are considered non-physiological and are likely a result of, e.g., signal error.

The term "ischemia," as used herein, is a broad term and is used in its ordinary sense, including, without limitation, to refer to local and temporary deficiency of blood supply due to obstruction of circulation to a part (for example, a sensor). Ischemia can be caused, for example, by mechanical obstruction (for example, arterial narrowing or disruption) of the blood supply.

The term "matched data pairs", as used herein, is a broad term and is used in its ordinary sense, including, without limitation, to refer to reference data (for example, one or more reference analyte data points) matched with substantially time corresponding sensor data (for example, one or more sensor data points).

The term "Clarke Error Grid", as used herein, is a broad term and is used in its ordinary sense, including, without limitation, to refer to an error grid analysis, for example, an error grid analysis used to evaluate the clinical significance of the difference between a reference glucose value and a sensor generated glucose value, taking into account 1) the value of the reference glucose measurement, 2) the value of the sensor glucose measurement, 3) the relative difference between the two values, and 4) the clinical significance of this difference. See Clarke et al., "Evaluating Clinical Accuracy of Systems for Self-Monitoring of Blood Glucose", Diabetes Care, Volume 10, Number 5, September-October 1987, the contents of which are hereby incorporated by reference herein in their entirety and are hereby made a part of this specification.

The term "Consensus Error Grid," as used herein, is a broad term and is used in its ordinary sense, including, without limitation, to refer to an error grid analysis that assigns a specific level of clinical risk to any possible error between two time corresponding measurements, e.g., glucose measurements. The Consensus Error Grid is divided into zones signifying the degree of risk posed by the deviation. See Parkes et al., "A New Consensus Error Grid to Evaluate the Clinical Significance of Inaccuracies in the Measurement of Blood Glucose", Diabetes Care, Volume 23, Number 8, August 2000, the contents of which are hereby incorporated by reference herein in their entirety and are hereby made a part of this specification.

The term "clinical acceptability", as used herein, is a broad term and is used in its ordinary sense, including, without limitation, to refer to determination of the risk of an inaccuracy to a patient. Clinical acceptability considers a deviation between time corresponding analyte measurements (for example, data from a glucose sensor and data from a reference glucose monitor) and the risk (for example, to the decision making of a person with diabetes) associated with that deviation based on the analyte value indicated by the sensor and/or reference data. An example of clinical acceptability can be 85% of a given set of measured analyte values within the "A" and "B" region of a standard Clarke Error Grid when the sensor measurements are compared to a standard reference measurement.

The term "sensor" as used herein is a broad term and is used in its ordinary sense, including, without limitation, to refer to the component or region of a device by which an analyte can be quantified.

The term "needle," as used herein is a broad term and is used in its ordinary sense, including, without limitation, to refer to a slender hollow instrument for introducing material into or removing material from the body.

The terms "operably connected" and "operably linked" as used herein are broad terms and are used in their ordinary sense, including, without limitation, to refer to one or more components linked to one or more other components. The terms can refer to a mechanical connection, an electrical connection, or a connection that allows transmission of signals between the components. For example, one or more electrodes can be used to detect the amount of analyte in a sample and to convert that information into a signal; the signal can then be transmitted to a circuit. In such an example, the electrode is "operably linked" to the electronic circuitry.

The term "baseline" as used herein is a broad term and is used in its ordinary sense, including, without limitation, is the component of an analyte sensor signal that is not related to the analyte concentration. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). In some embodiments wherein a calibration is defined by solving for the equation $y=mx+b$, the value of b represents the baseline of the signal.

The terms "sensitivity" and "slope," as used herein are broad terms and are used in their ordinary sense, including, without limitation, to refer to an amount of electrical current produced by a predetermined amount (unit) of the measured analyte. For example, in one preferred embodiment, a sensor has a sensitivity (or slope) of about 3.5 to about 7.5 picoAmps of current for every 1 mg/dL of glucose analyte.

The term "membrane system," as used herein, is a broad term and is used in its ordinary sense, including, without limitation, to refer to a permeable or semi-permeable membrane that can be comprised of two or more domains and is typically constructed of materials of a few microns thickness or more, which is permeable to oxygen and is optionally permeable to, e.g., glucose or another analyte. In one example, the membrane system comprises an immobilized glucose oxidase enzyme, which enables a reaction to occur between glucose and oxygen whereby a concentration of glucose can be measured.

The terms "processor module" and "microprocessor," as used herein, are broad terms and are used in their ordinary sense, without limitation, to refer to a computer system, state machine, processor, or the like designed to perform arithmetic or logic operations using logic circuitry that responds to and processes the basic instructions that drive a computer.

The terms "smoothing" and "filtering," as used herein, are broad terms and are used in their ordinary sense, without limitation, to refer to modification of a set of data to make it smoother and more continuous or to remove or diminish outlying points, for example, by performing a moving average of the raw data stream.

The term "algorithm," as used herein, is a broad term and is used in its ordinary sense, without limitation, to refer to a computational process (for example, programs) involved in transforming information from one state to another, for example, by using computer processing.

The term "regression," as used herein, is a broad term and is used in its ordinary sense, including, without limitation, to refer to finding a line for which a set of data has a minimal measurement (for example, deviation) from that line. Regression can be linear, non-linear, first order, second order, or the like. One example of regression is least squares regression.

The term "calibration," as used herein, is a broad term and is used in its ordinary sense, including, without limitation, to refer to the process of determining the relationship between the sensor data and the corresponding reference data, which can be used to convert sensor data into meaningful values substantially equivalent to the reference data. In some embodiments, namely, in continuous analyte sensors, calibration can be updated or recalibrated over time as changes in the relationship between the sensor data and reference data occur, for example, due to changes in sensitivity, baseline, transport, metabolism, or the like.

The terms "interferants" and "interfering species," as used herein, are broad terms and are used in their ordinary sense, including, without limitation, to refer to effects and/or species that interfere with the measurement of an analyte of interest in a sensor to produce a signal that does not accurately represent the analyte concentration. In one example of an electrochemical sensor, interfering species are compounds with an oxidation potential that overlap that of the analyte to be measured, thereby producing a false positive signal.

Sensor System

A transcutaneous analyte sensor system is provided that includes an applicator for inserting the transdermal analyte sensor under a host's skin. The sensor system includes a sensor for sensing the analyte, wherein the sensor is associated with a mounting unit adapted for mounting on the skin of the host. The mounting unit houses the electronics unit associated with the sensor and is adapted for fastening to the host's skin. In certain embodiments, the system further includes a receiver for receiving and/or processing sensor data.

FIG. 1 is a perspective view of a transcutaneous analyte sensor system 10. In the preferred embodiment of a system as depicted in FIG. 1, the sensor includes an applicator 12, a mounting unit 14, and an electronics unit 16. The system can further include a receiver 158, such as is described in more detail with reference to FIG. 14.

The mounting unit 14 includes a base 24 adapted for mounting on the skin of a host, a sensor adapted for transdermal insertion through the skin of a host (see FIG. 4), and one or more contacts 28 configured to provide secure electrical contact between the sensor and the electronics unit 16. The mounting unit 14 is designed to maintain the integrity of the sensor in the host so as to reduce or eliminate translation of motion between the mounting unit, the host, and/or the sensor.

In one embodiment, an applicator 12 is provided for inserting the sensor 32 through the host's skin at the appropriate insertion angle with the aid of a needle (see FIGS. 6 through 8), and for subsequent removal of the needle using a continuous push-pull action. Preferably, the applicator comprises an applicator body 18 that guides the applicator components (see FIGS. 6 through 8) and includes an applicator body base 60 configured to mate with the mounting unit 14 during insertion of the sensor into the host. The mate between the applicator body base 60 and the mounting unit 14 can use any known mating configuration, for example, a snap-fit, a press-fit, an interference-fit, or the like, to discourage separation during use. One or more release latches 30 enable release of the applicator body base 60, for example, when the applicator body base 60 is snap fit into the mounting unit 14.

The electronics unit 16 includes hardware, firmware, and/or software that enable measurement of levels of the analyte via the sensor. For example, the electronics unit 16 can comprise a potentiostat, a power source for providing power to the sensor, other components useful for signal processing, and preferably an RF module for transmitting data from the electronics unit 16 to a receiver (see FIGS. 13 to 15). Electronics can be affixed to a printed circuit board (PCB), or the like, and can take a variety of forms. For example, the electronics can take the form of an integrated circuit (IC), such as an Application-Specific Integrated Circuit (ASIC), a microcontroller, or a processor. Preferably, electronics unit 16 houses the sensor electronics, which comprise systems and methods for processing sensor analyte data. Examples of systems and methods for processing sensor analyte data are described in more detail below and in co-pending U.S. application Ser. No. 10/633,367 filed Aug. 1, 2003, and entitled, "SYSTEM AND METHODS FOR PROCESSING ANALYTE SENSOR DATA."

After insertion of the sensor using the applicator 12, and subsequent release of the applicator 12 from the mounting unit 14 (see FIGS. 8A to 8C), the electronics unit 16 is configured to releasably mate with the mounting unit 14 in a manner similar to that described above with reference to the applicator body base 60. The electronics unit 16 includes contacts on its backside (not shown) configured to electrically connect with the contacts 28, such as are described in more detail with reference to FIGS. 2 through 4. In one embodiment, the electronics unit 16 is configured with programming, for example initialization, calibration reset, failure testing, or the like, each time it is initially inserted into the mounting unit 14 and/or each time it initially communicates with the sensor 32.

Mounting Unit

Figure 2:
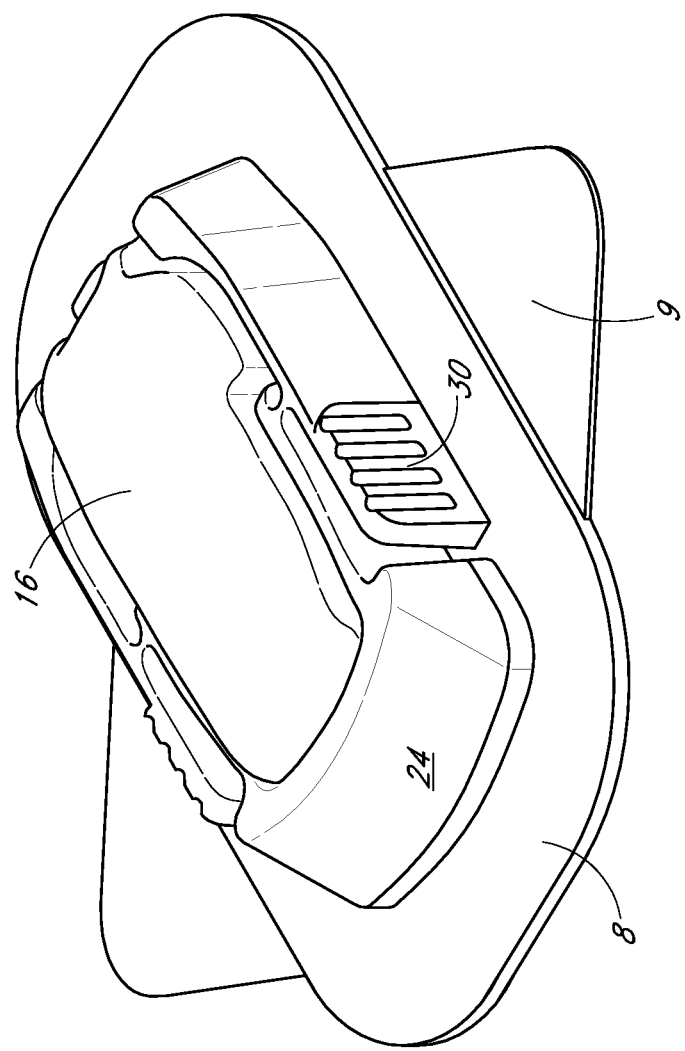
FIG. 2 is a perspective view of a mounting unit, including the electronics unit in its functional position.

FIG. 2 is a perspective view of a sensor system of a preferred embodiment, shown in its functional position, including a mounting unit and an electronics unit matingly engaged therein. FIGS. 8 to 10 illustrate the sensor is its functional position for measurement of an analyte concentration in a host.

In preferred embodiments, the mounting unit 14, also referred to as a housing, comprises a base 24 adapted for fastening to a host's skin. The base can be formed from a variety of hard or soft materials, and preferably comprises a low profile for minimizing protrusion of the device from the host during use. In some embodiments, the base 24 is formed at least partially from a flexible material, which is believed to provide numerous advantages over conventional transcutaneous sensors, which, unfortunately, can suffer from motion-related artifacts associated with the host's movement when the host is using the device. For example, when a transcutaneous analyte sensor is inserted into the host, various movements of the sensor (for example, relative movement between the in vivo portion and the ex vivo portion, movement of the skin, and/or movement within the host (dermis or subcutaneous)) create stresses on the device and can produce noise in the sensor signal. It is believed that even small movements of the skin can translate to discomfort and/or motion-related artifact, which can be reduced or obviated by a flexible or articulated base. Thus, by providing flexibility and/or articulation of the device against the host's skin, better conformity of the sensor system 10 to the regular use and movements of the host can be achieved. Flexibility or articulation is believed to increase adhesion (with the use of an adhesive pad) of the mounting unit 14 onto the skin, thereby decreasing motion-related artifact that can otherwise translate from the host's movements and reduced sensor performance.

Figure 3:
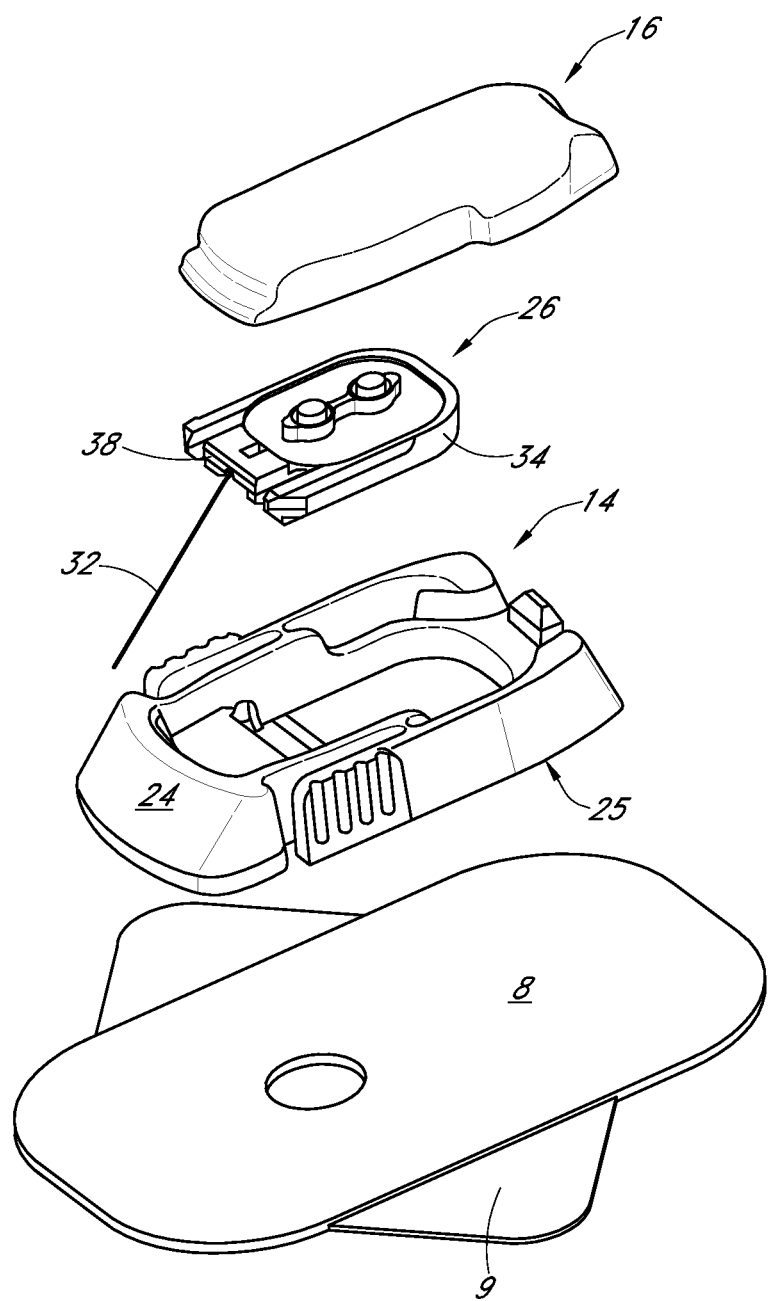
FIG. 3 is an exploded perspective view of a mounting unit, showing its individual components.

FIG. 3 is an exploded perspective view of a sensor system of a preferred embodiment, showing a mounting unit, an associated contact subassembly, and an electronics unit. In some embodiments, the contacts 28 are mounted on or in a subassembly hereinafter referred to as a contact subassembly 26 (see FIG. 4), which includes a contact holder 34 configured to fit within the base 24 of the mounting unit 14 and a hinge 38 that allows the contact subassembly 26 to pivot between a first position (for insertion) and a second position (for use) relative to the mounting unit 14, which is described in more detail with reference to FIGS. 10 and 11. The term "hinge" as used herein is a broad term and is used in its ordinary sense, including, without limitation, to refer to any of a variety of pivoting, articulating, and/or hinging mechanisms, such as an adhesive hinge, a sliding joint, and the like; the term hinge does not necessarily imply a fulcrum or fixed point about which the articulation occurs.

In certain embodiments, the mounting unit 14 is provided with an adhesive pad 8, preferably disposed on the mounting unit's back surface and preferably including a releasable backing layer 9. Thus, removing the backing layer 9 and pressing the base portion 24 of the mounting unit onto the host's skin adheres the mounting unit 14 to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site) (not shown). Appropriate adhesive pads can be chosen and designed to stretch, elongate, conform to, and/or aerate the region (e.g., host's skin).

In preferred embodiments, the adhesive pad 8 is formed from spun-laced, open- or closed-cell foam, and/or non-woven fibers, and includes an adhesive disposed thereon, however a variety of adhesive pads appropriate for adhesion to the host's skin can be used, as is appreciated by one skilled in the art of medical adhesive pads. In some embodiments, a double-sided adhesive pad is used to adhere the mounting unit to the host's skin. In other embodiments, the adhesive pad includes a foam layer, for example, a layer wherein the foam is disposed between the adhesive pad's side edges and acts as a shock absorber.

In some embodiments, the surface area of the adhesive pad 8 is greater than the surface area of the mounting unit's back surface. Alternatively, the adhesive pad can be sized with substantially the same surface area as the back surface of the base portion. Preferably, the adhesive pad has a surface area on the side to be mounted on the host's skin that is greater than about 1, 1.25, 1.5, 1.75, 2, 2.25, or 2.5, times the surface area of the back surface 25 of the mounting unit base 24. Such a greater surface area can increase adhesion between the mounting unit and the host's skin, minimize movement between the mounting unit and the host's skin, and/or protect the wound exit-site (sensor insertion site) from environmental and/or biological contamination. In some alternative embodiments, however, the adhesive pad can be smaller in surface area than the back surface assuming a sufficient adhesion can be accomplished.

In some embodiments, the adhesive pad 8 is substantially the same shape as the back surface 25 of the base 24, although other shapes can also be advantageously employed, for example, butterfly-shaped, round, square, or rectangular. The adhesive pad backing can be designed for two-step release, for example, a primary release wherein only a portion of the adhesive pad is initially exposed to allow adjustable positioning of the device, and a secondary release wherein the remaining adhesive pad is later exposed to firmly and securely adhere the device to the host's skin once appropriately positioned. The adhesive pad is preferably waterproof Preferably, a stretch-release adhesive pad is provided on the back surface of the base portion to enable easy release from the host's skin at the end of the useable life of the sensor, as is described in more detail with reference to FIGS. 9A to 9C.

In some circumstances, it has been found that a conventional bond between the adhesive pad and the mounting unit may not be sufficient, for example, due to humidity that can cause release of the adhesive pad from the mounting unit. Accordingly, in some embodiments, the adhesive pad can be bonded using a bonding agent activated by or accelerated by an ultraviolet, acoustic, radio frequency, or humidity cure. In some embodiments, a eutectic bond of first and second composite materials can form a strong adhesion. In some embodiments, the surface of the mounting unit can be pretreated utilizing ozone, plasma, chemicals, or the like, in order to enhance the bondability of the surface.

Figure 4:
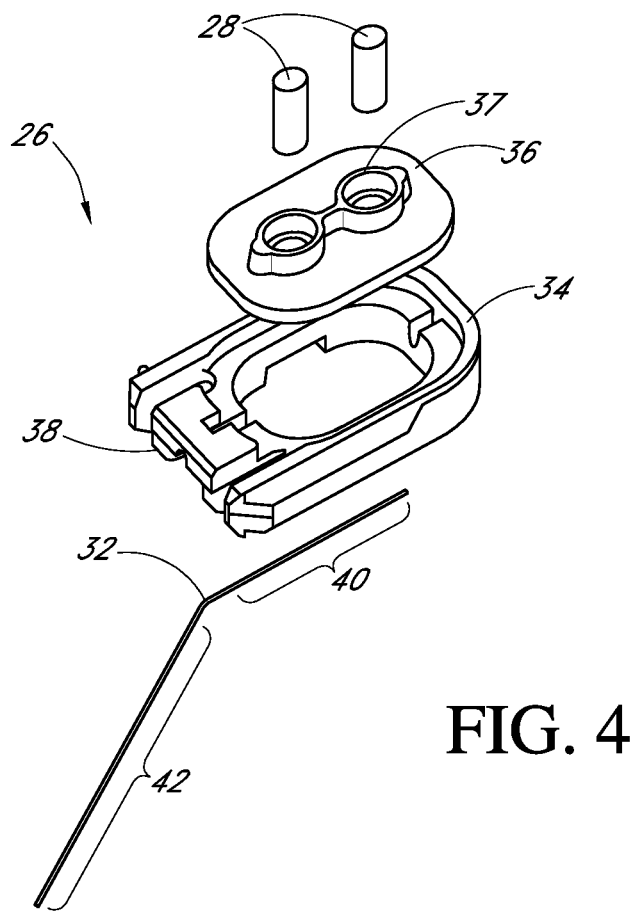
FIG. 4 is an exploded perspective view of a contact subassembly, showing its individual components.

A bioactive agent is preferably applied locally at the insertion site prior to or during sensor insertion. Suitable bioactive agents include those which are known to discourage or prevent bacterial growth and infection, for example, anti-inflammatory agents, antimicrobials, antibiotics, or the like. It is believed that the diffusion or presence of a bioactive agent can aid in prevention or elimination of bacteria adjacent to the exit-site. Additionally or alternatively, the bioactive agent can be integral with or coated on the adhesive pad, or no bioactive agent at all is employed FIG. 4 is an exploded perspective view of the contact subassembly 26 in one embodiment, showing its individual components. Preferably, a watertight (waterproof or water-resistant) sealing member 36, also referred to as a sealing material, fits within a contact holder 34 and provides a watertight seal configured to surround the electrical connection at the electrode terminals within the mounting unit in order to protect the electrodes (and the respective operable connection with the contacts of the electronics unit 16) from damage due to moisture, humidity, dirt, and other external environmental factors. In one embodiment, the sealing member 36 is formed from an elastomeric material, such as silicone; however, a variety of other elastomeric or sealing materials can also be used. In alternative embodiments, the seal is designed to form an interference fit with the electronics unit and can be formed from a variety of materials, for example, flexible plastics or noble metals. One of ordinary skill in the art appreciates that a variety of designs can be employed to provide a seal surrounding the electrical contacts described herein. For example, the contact holder 34 can be integrally designed as a part of the mounting unit, rather than as a separate piece thereof. Additionally or alternatively, a sealant can be provided in or around the sensor (e.g., within or on the contact subassembly or sealing member), such as is described in more detail with reference to FIGS. 11A and 11B.

In the illustrated embodiment, the sealing member 36 is formed with a raised portion 37 surrounding the contacts 28. The raised portion 37 enhances the interference fit surrounding the contacts 28 when the electronics unit 16 is mated to the mounting unit 14. Namely, the raised portion surrounds each contact and presses against the electronics unit 16 to form a tight seal around the electronics unit.

Contacts 28 fit within the seal 36 and provide for electrical connection between the sensor 32 and the electronics unit 16. In general, the contacts are designed to ensure a stable mechanical and electrical connection of the electrodes that form the sensor 32 (see FIG. 5A to 5C) to mutually engaging contacts 28 thereon. A stable connection can be provided using a variety of known methods, for example, domed metallic contacts, cantilevered fingers, pogo pins, or the like, as is appreciated by one skilled in the art.

Figure 10A:
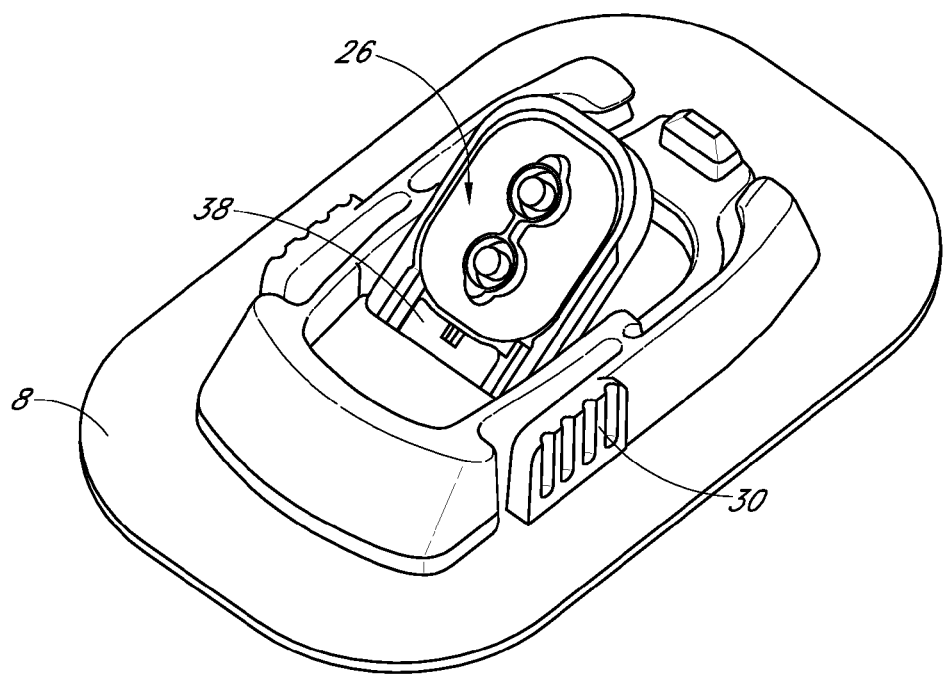
FIGS. 10A and 10B are perspective and side cross-sectional views, respectively, of a sensor system showing the mounting unit immediately following sensor insertion and release of the applicator from the mounting unit.
Figure 10B:
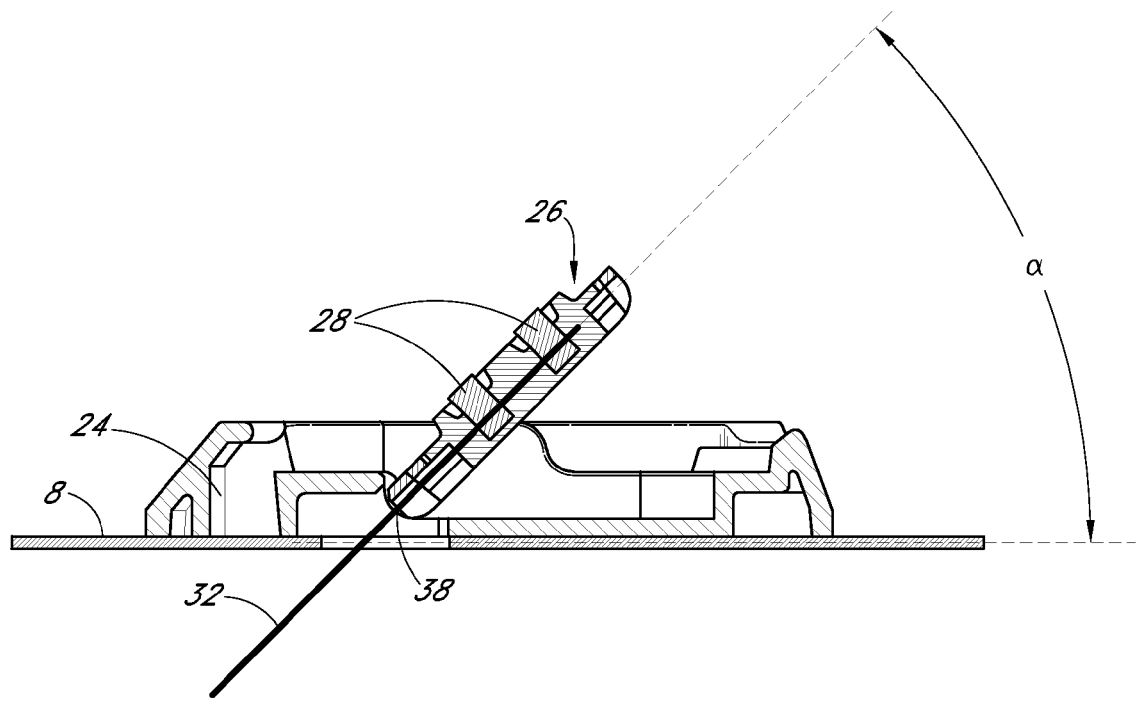
Figure 11A:
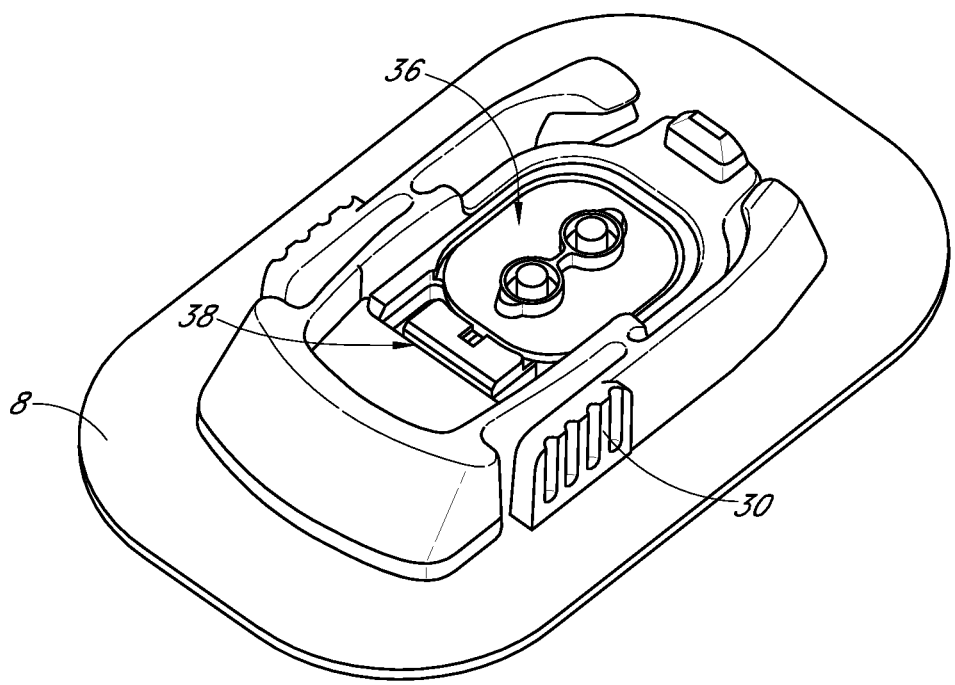
FIGS. 11A and 11B are perspective and side cross-sectional views, respectively, of a sensor system showing the mounting unit after pivoting the contact subassembly to its functional position.
Figure 11B:
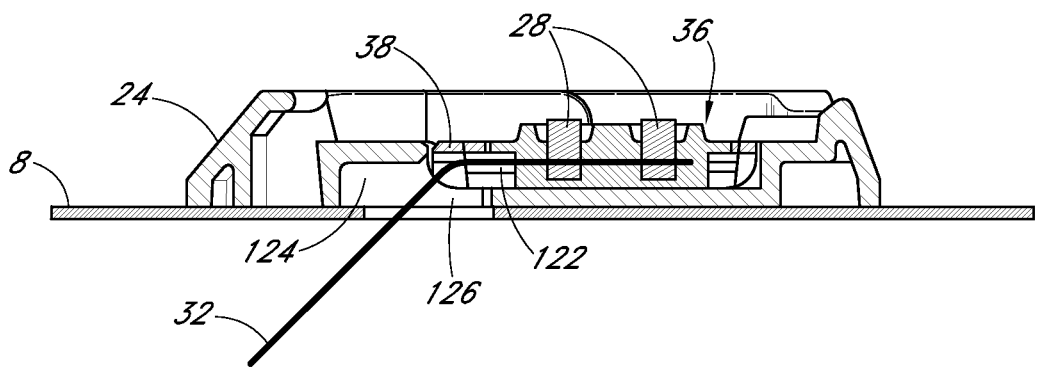

In preferred embodiments, the contacts 28 are formed from a conductive elastomeric material, such as a carbon black elastomer, through which the sensor 32 extends (see FIGS. 10B and 11B). Conductive elastomers are advantageously employed because their resilient properties create a natural compression against mutually engaging contacts, forming a secure press fit therewith. In some embodiments, conductive elastomers can be molded in such a way that pressing the elastomer against the adjacent contact performs a wiping action on the surface of the contact, thereby creating a cleaning action during initial connection. Additionally, in preferred embodiments, the sensor 32 extends through the contacts 28 wherein the sensor is electrically and mechanically secure by the relaxation of elastomer around the sensor (see FIGS. 7A to 7D).

In an alternative embodiment, a conductive, stiff plastic forms the contacts, which are shaped to comply upon application of pressure (for example, a leaf-spring shape). Contacts of such a configuration can be used instead of a metallic spring, for example, and advantageously avoid the need for crimping or soldering through compliant materials; additionally, a wiping action can be incorporated into the design to remove contaminants from the surfaces during connection. Non-metallic contacts can be advantageous because of their seamless manufacturability, robustness to thermal compression, non-corrosive surfaces, and native resistance to electrostatic discharge (ESD) damage due to their higher-than-metal resistance.

Sensor

Preferably, the sensor 32 includes a distal portion 42, also referred to as the in vivo portion, adapted to extend out of the mounting unit for insertion under the host's skin, and a proximal portion 40, also referred to as an ex vivo portion, adapted to remain above the host's skin after sensor insertion and to operably connect to the electronics unit 16 via contacts 28. Preferably, the sensor 32 includes two or more electrodes: a working electrode 44 and at least one additional electrode, which can function as a counter electrode and/or reference electrode, hereinafter referred to as the reference electrode 46. A membrane system is preferably deposited over the electrodes, such as described in more detail with reference to FIGS. 5A to 5C, below.

Figure 5A:
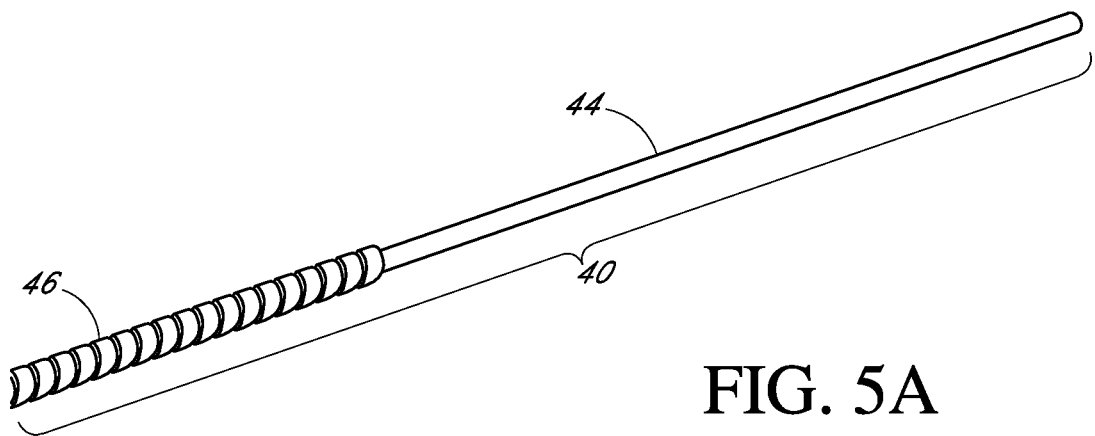
FIG. 5A is an expanded cutaway view of a proximal portion of a sensor.

FIG. 5A is an expanded cutaway view of a proximal portion 40 of the sensor in one embodiment, showing working and reference electrodes. In the illustrated embodiments, the working and reference electrodes 44, 46 extend through the contacts 28 to form electrical connection therewith (see FIGS. 10B and 11B). Namely, the working electrode 44 is in electrical contact with one of the contacts 28 and the reference electrode 46 is in electrical contact with the other contact 28, which in turn provides for electrical connection with the electronics unit 16 when it is mated with the mounting unit 14. Mutually engaging electrical contacts permit operable connection of the sensor 32 to the electronics unit 16 when connected to the mounting unit 14, however other methods of electrically connecting the electronics unit 16 to the sensor 32 are also possible. In some alternative embodiments, for example, the reference electrode can be configured to extend from the sensor and connect to a contact at another location on the mounting unit (e.g., non-coaxially). Detachable connection between the mounting unit 14 and electronics unit 16 provides improved manufacturability, namely, the relatively inexpensive mounting unit 14 can be disposed of when replacing the sensor system after its usable life, while the relatively more expensive electronics unit 16 can be reused with multiple sensor systems.

In alternative embodiments, the contacts 28 are formed into a variety of alternative shapes and/or sizes. For example, the contacts 28 can be discs, spheres, cuboids, and the like. Furthermore, the contacts 28 can be designed to extend from the mounting unit in a manner that causes an interference fit within a mating cavity or groove of the electronics unit, forming a stable mechanical and electrical connection therewith.

Figure 5B:
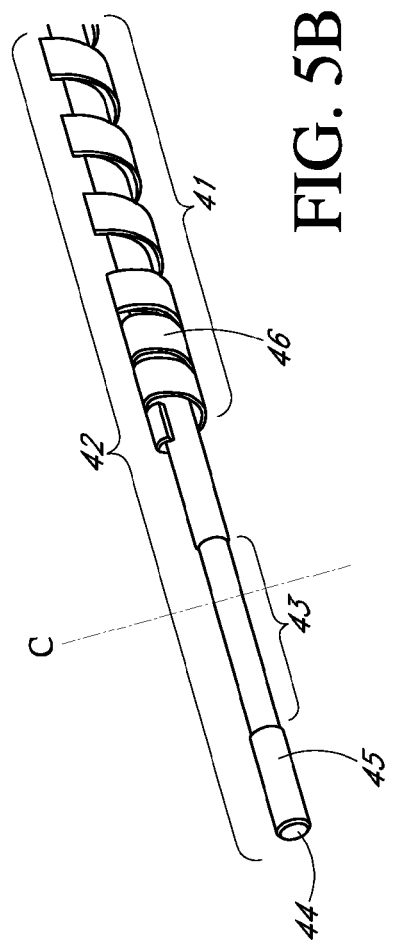
FIG. 5B is an expanded cutaway view of a distal portion of a sensor.

FIG. 5B is an expanded cutaway view of a distal portion of the sensor in one embodiment, showing working and reference electrodes. In preferred embodiments, the sensor is formed from a working electrode 44 and a reference electrode 46 helically wound around the working electrode 44. An insulator 45 is disposed between the working and reference electrodes to provide necessary electrical insulation there between. Certain portions of the electrodes are exposed to enable electrochemical reaction thereon, for example, a window 43 can be formed in the insulator to expose a portion of the working electrode 44 for electrochemical reaction.

In preferred embodiments, each electrode is formed from a fine wire with a diameter of from about 0.001 or less to about 0.010 inches or more, for example, and is formed from, e.g., a plated insulator, a plated wire, or bulk electrically conductive material. Although the illustrated electrode configuration and associated text describe one preferred method of forming a transcutaneous sensor, a variety of known transcutaneous sensor configurations can be employed with the transcutaneous analyte sensor system of the preferred embodiments, such as are described in U.S. Pat. No. 6,695,860 to Ward et al., U.S. Pat. No. 6,565,509 to Say et al., U.S. Pat. No. 6,248,067 to Causey III, et al., and U.S. Pat. No. 6,514,718 to Heller et al.

In preferred embodiments, the working electrode comprises a wire formed from a conductive material, such as platinum, platinum-iridium, palladium, graphite, gold, carbon, conductive polymer, alloys, or the like. Although the electrodes can by formed by a variety of manufacturing techniques (bulk metal processing, deposition of metal onto a substrate, or the like), it can be advantageous to form the electrodes from plated wire (e.g. platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

The working electrode 44 is configured to measure the concentration of an analyte. In an enzymatic electrochemical sensor for detecting glucose, for example, the working electrode measures the hydrogen peroxide produced by an enzyme catalyzed reaction of the analyte being detected and creates a measurable electronic current For example, in the detection of glucose wherein glucose oxidase produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected.

In preferred embodiments, the working electrode 44 is covered with an insulating material 45, for example, a nonconductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). However, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode may not require a coating of insulator.

The reference electrode 46, which can function as a reference electrode alone, or as a dual reference and counter electrode, is formed from silver, silver/silver chloride, or the like. Preferably, the reference electrode 46 is juxtapositioned and/or twisted with or around the working electrode 44; however other configurations are also possible. In the illustrated embodiments, the reference electrode 46 is helically wound around the working electrode 44. The assembly of wires is then optionally coated or adhered together with an insulating material, similar to that described above, so as to provide an insulating attachment.

In embodiments wherein an outer insulator is disposed, a portion of the coated assembly structure can be stripped or otherwise removed, for example, by hand, excimer lasing, chemical etching, laser ablation, grit-blasting (e.g., with sodium bicarbonate or other suitable grit), or the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, e.g., a parylene coating without damaging, e.g., an underlying platinum conductor. One additional advantage of sodium bicarbonate blasting includes its polishing action on the metal as it strips the polymer layer, thereby eliminating a cleaning step that might otherwise be necessary.

In the embodiment illustrated in FIG. 5B, a radial window 43 is formed through the insulating material 45 to expose a circumferential electroactive surface of the working electrode. Additionally, sections 41 of electroactive surface of the reference electrode are exposed. For example, the 41 sections of electroactive surface can be masked during deposition of an outer insulating layer or etched after deposition of an outer insulating layer.

In some applications, cellular attack or migration of cells to the sensor can cause reduced sensitivity and/or function of the device, particularly after the first day of implantation. However, when the exposed electroactive surface is distributed circumferentially about the sensor (e.g., as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

In some embodiments, the working electrode has a diameter of from about 0.001 inches or less to about 0.010 inches or more, preferably from about 0.002 inches to about 0.008 inches, and more preferably from about 0.004 inches to about 0.005 inches. The length of the window can be from about 0.1 mm (about 0.004 inches) or less to about 2 mm (about 0.078 inches) or more, and preferably from about 0.5 mm (about 0.02 inches) to about 0.75 mm (0.03 inches). In such embodiments, the exposed surface area of the working electrode is preferably from about 0.000013 $in^2$ (0.0000839 $cm^2$) or less to about 0.0025 $in^2$ (0.016129 $cm^2$) or more (assuming a diameter of from about 0.001 inches to about 0.010 inches and a length of from about 0.004 inches to about 0.078 inches). The preferred exposed surface area of the working electrode is selected to produce an analyte signal with a current in the picoAmp range, such as is described in more detail elsewhere herein. However, a current in the picoAmp range can be dependent upon a variety of factors, for example the electronic circuitry design (e.g., sample rate, current draw, A/D converter bit resolution, etc.), the membrane system (e.g., permeability of the analyte through the membrane system), and the exposed surface area of the working electrode. Accordingly, the exposed electroactive working electrode surface area can be selected to have a value greater than or less than the above-described ranges taking into consideration alterations in the membrane system and/or electronic circuitry. In preferred embodiments of a glucose sensor, it can be advantageous to minimize the surface area of the working electrode while maximizing the diffusivity of glucose in order to optimize the signal-to-noise ratio while maintaining sensor performance in both high and low glucose concentration ranges.

In some alternative embodiments, the exposed surface area of the working (and/or other) electrode can be increased by altering the cross-section of the electrode itself. For example, in some embodiments the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example.

In some alternative embodiments, additional electrodes can be included within the assembly, for example, a three-electrode system (working, reference, and counter electrodes) and/or an additional working electrode (e.g., an electrode which can be used to generate oxygen, which is configured as a baseline subtracting electrode, or which is configured for measuring additional analytes). Co-pending U.S. patent application Ser. No. 11/007,635, filed Dec. 7, 2004 and entitled "SYSTEMS AND METHODS FOR IMPROVING ELECTROCHEMICAL ANALYTE SENSORS" and U.S. patent application Ser. No. 11/004,561, filed Dec. 3, 2004 and entitled "CALIBRATION TECHNIQUES FOR A CONTINUOUS ANALYTE SENSOR" describe some systems and methods for implementing and using additional working, counter, and/or reference electrodes. In one implementation wherein the sensor comprises two working electrodes, the two working electrodes are juxtapositioned (e.g., extend parallel to each other), around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure.) The resulting electrode system can be configured with an appropriate membrane system, wherein the first working electrode is configured to measure a first signal comprising glucose and baseline and the additional working electrode is configured to measure a baseline signal consisting of baseline only (e.g., configured to be substantially similar to the first working electrode without an enzyme disposed thereon.) In this way, the baseline signal can be subtracted from the first signal to produce a glucose-only signal that is substantially not subject to fluctuations in the baseline and/or interfering species on the signal.

Although the preferred embodiments illustrate one electrode configuration including one bulk metal wire helically wound around another bulk metal wire, other electrode configurations are also contemplated. In an alternative embodiment, the working electrode comprises a tube with a reference electrode disposed or coiled inside, including an insulator there between. Alternatively, the reference electrode comprises a tube with a working electrode disposed or coiled inside, including an insulator there between. In another alternative embodiment, a polymer (e.g., insulating) rod is provided, wherein the electrodes are deposited (e.g., electroplated) thereon. In yet another alternative embodiment, a metallic (e.g., steel) rod is provided, coated with an insulating material, onto which the working and reference electrodes are deposited. In yet another alternative embodiment, one or more working electrodes are helically wound around a reference electrode.

Preferably, the electrodes and membrane systems of the preferred embodiments are coaxially formed, namely, the electrodes and/or membrane system all share the same central axis. While not wishing to be bound by theory, it is believed that a coaxial design of the sensor enables a symmetrical design without a preferred bend radius. Namely, in contrast to prior art sensors comprising a substantially planar configuration that can suffer from regular bending about the plane of the sensor, the coaxial design of the preferred embodiments do not have a preferred bend radius and therefore are not subject to regular bending about a particular plane (which can cause fatigue failures and the like). However, non-coaxial sensors can be implemented with the sensor system of the preferred embodiments.

In addition to the above-described advantages, the coaxial sensor design of the preferred embodiments enables the diameter of the connecting end of the sensor (proximal portion) to be substantially the same as that of the sensing end (distal portion) such that the needle is able to insert the sensor into the host and subsequently slide back over the sensor and release the sensor from the needle, without slots or other complex multi-component designs.

In one such alternative embodiment, the two wires of the sensor are held apart and configured for insertion into the host in proximal but separate locations. The separation of the working and reference electrodes in such an embodiment can provide additional electrochemical stability with simplified manufacture and electrical connectivity. It is appreciated by one skilled in the art that a variety of electrode configurations can be implemented with the preferred embodiments.

Anchoring Mechanism

It is preferred that the sensor remains substantially stationary within the tissue of the host, such that migration or motion of the sensor with respect to the surrounding tissue is minimized. Migration or motion is believed to cause inflammation at the sensor implant site due to irritation, and can also cause noise on the sensor signal due to motion-related artifact, for example. Therefore, it can be advantageous to provide an anchoring mechanism that provides support for the sensor's in vivo portion to avoid the above-mentioned problems. Combining advantageous sensor geometry with an advantageous anchoring minimizes additional parts and allows for an optimally small or low profile design of the sensor. In one embodiment the sensor includes a surface topography, such as the helical surface topography provided by the reference electrode surrounding the working electrode. In alternative embodiments, a surface topography could be provided by a roughened surface, porous surface (e.g. porous parylene), ridged surface, or the like. Additionally (or alternatively), the anchoring can be provided by prongs, spines, barbs, wings, hooks, a bulbous portion (for example, at the distal end), an S-bend along the sensor, a rough surface topography, a gradually changing diameter, combinations thereof, or the like, which can be used alone or in combination with the helical surface topography to stabilize the sensor within the subcutaneous tissue.

Variable Stiffness

As described above, conventional transcutaneous devices are believed to suffer from motion artifact associated with host movement when the host is using the device. For example, when a transcutaneous analyte sensor is inserted into the host, various movements on the sensor (for example, relative movement within and between the subcutaneous space, dermis, skin, and external portions of the sensor) create stresses on the device, which is known to produce artifacts on the sensor signal. Accordingly, there are different design considerations (for example, stress considerations) on various sections of the sensor. For example, the distal portion 42 of the sensor can benefit in general from greater flexibility as it encounters greater mechanical stresses caused by movement of the tissue within the patient and relative movement between the in vivo and ex vivo portions of the sensor. On the other hand, the proximal portion 40 of the sensor can benefit in general from a stiffer, more robust design to ensure structural integrity and/or reliable electrical connections. Additionally, in some embodiments wherein a needle is retracted over the proximal portion 40 of the device (see FIGS. 6 to 8), a stiffer design can minimize crimping of the sensor and/or ease in retraction of the needle from the sensor. Thus, by designing greater flexibility into the in vivo (distal) portion 42, the flexibility is believed to compensate for patient movement, and noise associated therewith. By designing greater stiffness into the ex vivo (proximal) portion 40, column strength (for retraction of the needle over the sensor), electrical connections, and integrity can be enhanced. In some alternative embodiments, a stiffer distal end and/or a more flexible proximal end can be advantageous as described in co-pending U.S. patent application Ser. No. 11/077,759, filed on even date herewith and entitled "TRANSCUTANEOUS MEDICAL DEVICE WITH VARIABLE STIFFNESS."

The preferred embodiments provide a distal portion 42 of the sensor 32 designed to be more flexible than a proximal portion 40 of the sensor. The variable stiffness of the preferred embodiments can be provided by variable pitch of any one or more helically wound wires of the device, variable cross-section of any one or more wires of the device, and/or variable hardening and/or softening of any one or more wires of the device, such as is described in more detail with reference to co-pending U.S. patent application Ser. No. 11/077,759 described above and entitled "TRANSCUTANEOUS MEDICAL DEVICE WITH VARIABLE STIFFNESS."

Membrane System

Figure 5C:
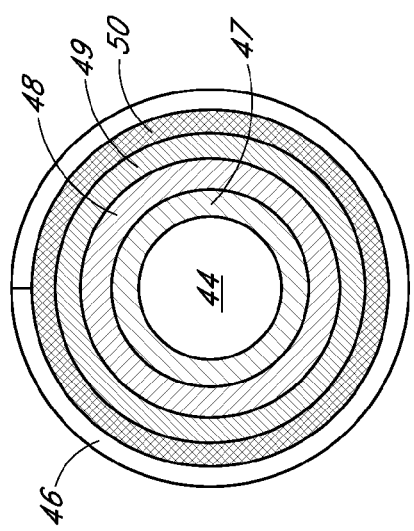
FIG. 5C is a cross-sectional view through the sensor of FIG. 5B on line C-C, showing an exposed electroactive surface of a working electrode surrounded by a membrane system.

FIG. 5C is a cross-sectional view through the sensor on line C-C of FIG. 5B showing the exposed electroactive surface of the working electrode surrounded by the membrane system in one embodiment. Preferably, a membrane system is deposited over at least a portion of the electroactive surfaces of the sensor 32 (working electrode and optionally reference electrode) and provides protection of the exposed electrode surface from the biological environment, diffusion resistance (limitation) of the analyte if needed, a catalyst for enabling an enzymatic reaction, limitation or blocking of interferants, and/or hydrophilicity at the electrochemically reactive surfaces of the sensor interface. Some examples of suitable membrane systems are described in co-pending U.S. patent application Ser. No. 10/838,912, filed May 3, 2004 and entitled "IMPLANTABLE ANALYTE SENSOR."

In general, the membrane system includes a plurality of domains, for example, an electrode domain 47, an interference domain 48, an enzyme domain 49 (for example, including glucose oxidase), and a resistance domain 50, and can include a high oxygen solubility domain, and/or a bioprotective domain (not shown), such as is described in more detail in U.S. patent application Ser. No. 10/838,912, and such as is described in more detail below. The membrane system can be deposited on the exposed electroactive surfaces using known thin film techniques (for example, spraying, electro-depositing, dipping, or the like). In one embodiment, one or more domains are deposited by dipping the sensor into a solution and drawing out the sensor at a speed that provides the appropriate domain thickness. However, the membrane system can be disposed over (or deposited on) the electroactive surfaces using any known method as will be appreciated by one skilled in the art.

Electrode Domain

In some embodiments, the membrane system comprises an optional electrode domain 47. The electrode domain 47 is provided to ensure that an electrochemical reaction occurs between the electroactive surfaces of the working electrode and the reference electrode, and thus the electrode domain 47 is preferably situated more proximal to the electroactive surfaces than the enzyme domain. Preferably, the electrode domain 47 includes a semipermeable coating that maintains a layer of water at the electrochemically reactive surfaces of the sensor, for example, a humectant in a binder material can be employed as an electrode domain; this allows for the full transport of ions in the aqueous environment. The electrode domain can also assist in stabilizing the operation of the sensor by overcoming electrode start-up and drifting problems caused by inadequate electrolyte. The material that forms the electrode domain can also protect against pH-mediated damage that can result from the formation of a large pH gradient due to the electrochemical activity of the electrodes.

In one embodiment, the electrode domain 47 includes a flexible, water-swellable, hydrogel film having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain 47 is formed of a curable mixture of a urethane polymer and a hydrophilic polymer. Particularly preferred coatings are formed of a polyurethane polymer having carboxylate functional groups and non-ionic hydrophilic polyether segments, wherein the polyurethane polymer is crosslinked with a water soluble carbodiimide (e.g., 1-ethyl-3-(3-dimethylaminopropyl)carbodiimide (EDC))) in the presence of polyvinylpyrrolidone and cured at a moderate temperature of about 50° C.

Preferably, the electrode domain 47 is deposited by spray or dip-coating the electroactive surfaces of the sensor 32. More preferably, the electrode domain is formed by dip-coating the electroactive surfaces in an electrode solution and curing the domain for a time of from about 15 to about 30 minutes at a temperature of from about 40 to about 55° C. (and can be accomplished under vacuum (e.g., 20 to 30 mmHg)). In embodiments wherein dip-coating is used to deposit the electrode domain, a preferred insertion rate of from about 1 to about 3 inches per minute, with a preferred dwell time of from about 0.5 to about 2 minutes, and a preferred withdrawal rate of from about 0.25 to about 2 inches per minute provide a functional coating. However, values outside of those set forth above can be acceptable or even desirable in certain embodiments, for example, dependent upon viscosity and surface tension as is appreciated by one skilled in the art. In one embodiment, the electroactive surfaces of the electrode system are dip-coated one time (one layer) and cured at 50° C. under vacuum for 20 minutes.

Although an independent electrode domain is described herein, in some embodiments, sufficient hydrophilicity can be provided in the interference domain and/or enzyme domain (the domain adjacent to the electroactive surfaces) so as to provide for the full transport of ions in the aqueous environment (e.g. without a distinct electrode domain).

Interference Domain

In some embodiments, an optional interference domain 48 is provided, which generally includes a polymer domain that restricts the flow of one or more interferants. In some embodiments, the interference domain 48 functions as a molecular sieve that allows analytes and other substances that are to be measured by the electrodes to pass through, while preventing passage of other substances, including interferants such as ascorbate and urea (see U.S. Pat. No. 6,001,067 to Shults). Some known interferants for a glucose-oxidase based electrochemical sensor include acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid.

Several polymer types that can be utilized as a base material for the interference domain 48 include polyurethanes, polymers having pendant ionic groups, and polymers having controlled pore size, for example. In one embodiment, the interference domain includes a thin, hydrophobic membrane that is non-swellable and restricts diffusion of low molecular weight species. The interference domain 48 is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in co-pending U.S. patent application Ser. No. 10/896,312 filed Jul. 21, 2004 and entitled "ELECTRODE SYSTEMS FOR ELECTROCHEMICAL SENSORS," Ser. No. 10/991,353, filed Nov. 16, 2004 and entitled, "AFFINITY DOMAIN FOR AN ANALYTE SENSOR," Ser. No. 11/007,635, filed Dec. 7, 2004 and entitled "SYSTEMS AND METHODS FOR IMPROVING ELECTROCHEMICAL ANALYTE SENSORS" and Ser. No. 11/004,561, filed Dec. 3, 2004 and entitled, "CALIBRATION TECHNIQUES FOR A CONTINUOUS ANALYTE SENSOR." In some alternative embodiments, a distinct interference domain is not included.

In preferred embodiments, the interference domain 48 is deposited onto the electrode domain (or directly onto the electroactive surfaces when a distinct electrode domain is not included) for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. Thicker membranes can also be useful, but thinner membranes are generally preferred because they have a lower impact on the rate of diffusion of hydrogen peroxide from the enzyme membrane to the electrodes. Unfortunately, the thin thickness of the interference domains conventionally used can introduce variability in the membrane system processing. For example, if too much or too little interference domain is incorporated within a membrane system, the performance of the membrane can be adversely affected.

Enzyme Domain

In preferred embodiments, the membrane system further includes an enzyme domain 49 disposed more distally situated from the electroactive surfaces than the interference domain 48 (or electrode domain 47 when a distinct interference is not included). In some embodiments, the enzyme domain is directly deposited onto the electroactive surfaces (when neither an electrode or interference domain is included). In the preferred embodiments, the enzyme domain 49 provides an enzyme to catalyze the reaction of the analyte and its co-reactant, as described in more detail below. Preferably, the enzyme domain includes glucose oxidase, however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase, are subject to deactivation as a function of time even in ambient conditions, this behavior is compensated for in forming the enzyme domain. Preferably, the enzyme domain 49 is constructed of aqueous dispersions of colloidal polyurethane polymers including the enzyme. However, in alternative embodiments the enzyme domain is constructed from an oxygen enhancing material, for example, silicone or fluorocarbon, in order to provide a supply of excess oxygen during transient ischemia. Preferably, the enzyme is immobilized within the domain. See U.S. patent application Ser. No. 10/896,639 filed on Jul. 21, 2004 and entitled "Oxygen Enhancing Membrane Systems for Implantable Device."

In preferred embodiments, the enzyme domain 49 is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. However in some embodiments, the enzyme domain is deposited onto the electrode domain or directly onto the electroactive surfaces. Preferably, the enzyme domain 49 is deposited by spray or dip coating. More preferably, the enzyme domain is formed by dip-coating the electrode domain into an enzyme domain solution and curing the domain for from about 15 to about 30 minutes at a temperature of from about 40 to about 55° C. (and can be accomplished under vacuum (e.g., 20 to 30 mmHg)). In embodiments wherein dip-coating is used to deposit the enzyme domain at room temperature, a preferred insertion rate of from about 1 inch per minute to about 3 inches per minute, with a preferred dwell time of from about 0.5 minutes to about 2 minutes, and a preferred withdrawal rate of from about 0.25 inch per minute to about 2 inches per minute provide a functional coating. However, values outside of those set forth above can be acceptable or even desirable in certain embodiments, for example, dependent upon viscosity and surface tension as is appreciated by one skilled in the art. In one embodiment, the enzyme domain 49 is formed by dip coating two times (namely, forming two layers) in a coating solution and curing at 50° C. under vacuum for 20 minutes. However, in some embodiments, the enzyme domain can be formed by dip-coating and/or spray-coating one or more layers at a predetermined concentration of the coating solution, insertion rate, dwell time, withdrawal rate, and/or desired thickness.

Resistance Domain

In preferred embodiments, the membrane system includes a resistance domain 50 disposed more distal from the electroactive surfaces than the enzyme domain 49. Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21 (1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain 50 includes a semi permeable membrane that controls the flux of oxygen and glucose to the underlying enzyme domain 49, preferably rendering oxygen in a non-rate-limiting excess. As a result, the upper limit of linearity of glucose measurement is extended to a much higher value than that which is achieved without the resistance domain. In one embodiment, the resistance domain 50 exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain 49. If more oxygen is supplied to the enzyme, then more glucose can also be supplied to the enzyme without creating an oxygen rate-limiting excess. In alternative embodiments, the resistance domain is formed from a silicone composition, such as is described in co-pending U.S. application Ser. No. 10/695,636 filed Oct. 28, 2003 and entitled, "SILICONE COMPOSITION FOR BIOCOMPATIBLE MEMBRANE."

In a preferred embodiment, the resistance domain 50 includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In preferred embodiments, the resistance domain 50 is deposited onto the enzyme domain 49 to yield a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. Preferably, the resistance domain is deposited onto the enzyme domain by spray coating or dip coating. In certain embodiments, spray coating is the preferred deposition technique. The spraying process atomizes and mists the solution, and therefore most or all of the solvent is evaporated prior to the coating material settling on the underlying domain, thereby minimizing contact of the solvent with the enzyme. One additional advantage of spray-coating the resistance domain as described in the preferred embodiments includes formation of a membrane system that substantially blocks or resists ascorbate (a known electrochemical interferant in hydrogen peroxide-measuring glucose sensors). While not wishing to be bound by theory, it is believed that during the process of depositing the resistance domain as described in the preferred embodiments, a structural morphology is formed, characterized in that ascorbate does not substantially permeate there through.

In preferred embodiments, the resistance domain 50 is deposited on the enzyme domain 49 by spray-coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain 49. Tetrahydrofuran (THF) is one solvent that minimally or negligibly affects the enzyme of the enzyme domain upon spraying. Other solvents can also be suitable for use, as is appreciated by one skilled in the art.

Although a variety of spraying or deposition techniques can be used, spraying the resistance domain material and rotating the sensor at least one time by 180° can provide adequate coverage by the resistance domain. Spraying the resistance domain material and rotating the sensor at least two times by 120 degrees provides even greater coverage (one layer of 360° coverage), thereby ensuring resistivity to glucose, such as is described in more detail above.

In preferred embodiments, the resistance domain 50 is spray-coated and subsequently cured for a time of from about 15 to about 90 minutes at a temperature of from about 40 to about 60° C. (and can be accomplished under vacuum (e.g., 20 to 30 mmHg)). A cure time of up to about 90 minutes or more can be advantageous to ensure complete drying of the resistance domain. While not wishing to be bound by theory, it is believed that complete drying of the resistance domain aids in stabilizing the sensitivity of the glucose sensor signal. It reduces drifting of the signal sensitivity over time, and complete drying is believed to stabilize performance of the glucose sensor signal in lower oxygen environments.

In one embodiment, the resistance domain 50 is formed by spray-coating at least six layers (namely, rotating the sensor seventeen times by 120° for at least six layers of 360° coverage) and curing at 50° C. under vacuum for 60 minutes. However, the resistance domain can be formed by dip-coating or spray-coating any layer or plurality of layers, depending upon the concentration of the solution, insertion rate, dwell time, withdrawal rate, and/or the desired thickness of the resulting film.

Advantageously, sensors with the membrane system of the preferred embodiments, including an electrode domain 47 and/or interference domain 48, an enzyme domain 49, and a resistance domain 50, provide stable signal response to increasing glucose levels of from about 40 to about 400 mg/dL, and sustained function (at least 90% signal strength)

even at low oxygen levels (for example, at about 0.6 mg/L $O_2$). While not wishing to be bound by theory, it is believed that the resistance domain provides sufficient resistivity, or the enzyme domain provides sufficient enzyme, such that oxygen limitations are seen at a much lower concentration of oxygen as compared to prior art sensors.

In preferred embodiments, a sensor signal with a current in the picoAmp range is preferred, which is described in more detail elsewhere herein. However, the ability to produce a signal with a current in the picoAmp range can be dependent upon a combination of factors, including the electronic circuitry design (e.g., A/D converter, bit resolution, and the like), the membrane system (e.g., permeability of the analyte through the resistance domain, enzyme concentration, and/or electrolyte availability to the electrochemical reaction at the electrodes), and the exposed surface area of the working electrode. For example, the resistance domain can be designed to be more or less restrictive to the analyte depending upon to the design of the electronic circuitry, membrane system, and/or exposed electroactive surface area of the working electrode.

Accordingly, in preferred embodiments, the membrane system is designed with a sensitivity of from about 1 pA/mg/dL to about 100 pA/mg/dL, preferably from about 5 pA/mg/dL to 25 pA/mg/dL, and more preferably from about 4 to about 7 pA/mg/dL. While not wishing to be bound by any particular theory, it is believed that membrane systems designed with a sensitivity in the preferred ranges permit measurement of the analyte signal in low analyte and/or low oxygen situations. Namely, conventional analyte sensors have shown reduced measurement accuracy in low analyte ranges due to lower availability of the analyte to the sensor and/or have shown increased signal noise in high analyte ranges due to insufficient oxygen necessary to react with the amount of analyte being measured. While not wishing to be bound by theory, it is believed that the membrane systems of the preferred embodiments, in combination with the electronic circuitry design and exposed electrochemical reactive surface area design, support measurement of the analyte in the picoAmp range, which enables an improved level of resolution and accuracy in both low and high analyte ranges not seen in the prior art.

Mutarotase Enzyme

In some embodiments, mutarotase, an enzyme that converts α D-glucose to β D-glucose, is incorporated into the membrane system. Mutarotase can be incorporated into the enzyme domain and/or can be incorporated into another domain of the membrane system. In general, glucose exists in two distinct isomers, α and β, which are in equilibrium with one another in solution and in the blood or interstitial fluid. At equilibrium, α is present at a relative concentration of about 35.5% and β is present in the relative concentration of about 64.5% (see Okuda et. al., *Anal Biochem.* 1971 September; 43(1):312-5). Glucose oxidase, which is a conventional enzyme used to react with glucose in glucose sensors, reacts with β D-glucose and not with α D-glucose. Since only the β D-glucose isomer reacts with the glucose oxidase, errant readings may occur in a glucose sensor responsive to a shift of the equilibrium between the α D-glucose and the β D-glucose. Many compounds, such as calcium, can affect equilibrium shifts of α D-glucose and β D-glucose. For example, as disclosed in U.S. Pat. No. 3,964,974 to Banaugh et al., compounds that exert a mutarotation accelerating effect on α D-glucose include histidine, aspartic acid, imidazole, glutamic acid, α hydroxyl pyridine, and phosphate.

Accordingly, a shift in α D-glucose and β D-glucose equilibrium can cause a glucose sensor based on glucose oxidase to err high or low. To overcome the risks associated with errantly high or low sensor readings due to equilibrium shifts, the sensor of the preferred embodiments can be configured to measure total glucose in the host, including α D-glucose and β D-glucose by the incorporation of the mutarotase enzyme, which converts α D-glucose to β D-glucose.

Although sensors of some embodiments described herein include an optional interference domain in order to block or reduce one or more interferants, sensors with the membrane system of the preferred embodiments, including an electrode domain 47, an enzyme domain 48, and a resistance domain 49, have been shown to inhibit ascorbate without an additional interference domain. Namely, the membrane system of the preferred embodiments, including an electrode domain 47, an enzyme domain 48, and a resistance domain 49, has been shown to be substantially non-responsive to ascorbate in physiologically acceptable ranges. While not wishing to be bound by theory, it is believed that the processing process of spraying the depositing the resistance domain by spray coating, as described herein, forms results in a structural morphology that is substantially resistance resistant to ascorbate.

Interference-Free Membrane Systems

In general, it is believed that appropriate solvents and/or deposition methods can be chosen for one or more of the domains of the membrane system that form one or more transitional domains such that interferants do not substantially permeate there through. Thus, sensors can be built without distinct or deposited interference domains, which are non-responsive to interferants. While not wishing to be bound by theory, it is believed that a simplified multilayer membrane system, more robust multilayer manufacturing process, and reduced variability caused by the thickness and associated oxygen and glucose sensitivity of the deposited micron-thin interference domain can be provided. Additionally, the optional polymer-based interference domain, which usually inhibits hydrogen peroxide diffusion, is eliminated, thereby enhancing the amount of hydrogen peroxide that passes through the membrane system.

Oxygen Conduit

As described above, certain sensors depend upon an enzyme within the membrane system through which the host's bodily fluid passes and in which the analyte (for example, glucose) within the bodily fluid reacts in the presence of a co-reactant (for example, oxygen) to generate a product. The product is then measured using electrochemical methods, and thus the output of an electrode system functions as a measure of the analyte. For example, when the sensor is a glucose oxidase based glucose sensor, the species measured at the working electrode is $H_2O_2$. An enzyme, glucose oxidase, catalyzes the conversion of oxygen and glucose to hydrogen peroxide and gluconate according to the following reaction:

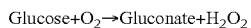
$$\text{Glucose} + O_2 \rightarrow \text{Gluconate} + H_2O_2$$

Because for each glucose molecule reacted there is a proportional change in the product, $H_2O_2$, one can monitor the change in $H_2O_2$ to determine glucose concentration. Oxidation of $H_2O_2$ by the working electrode is balanced by reduction of ambient oxygen, enzyme generated $H_2O_2$ and other reducible species at a counter electrode, for example. See Fraser, D. M., "An Introduction to In Vivo Biosensing: Progress and Problems." In "Biosensors and the Body," D. M. Fraser, ed., 1997, pp. 1-56 John Wiley and Sons, New York))

In vivo, glucose concentration is generally about one hundred times or more that of the oxygen concentration. Consequently, oxygen is a limiting reactant in the electrochemical reaction, and when insufficient oxygen is provided to the sensor, the sensor is unable to accurately measure glucose concentration. Thus, depressed sensor function or inaccuracy is believed to be a result of problems in availability of oxygen to the enzyme and/or electroactive surface(s).

Accordingly, in an alternative embodiment, an oxygen conduit (for example, a high oxygen solubility domain formed from silicone or fluorochemicals) is provided that extends from the ex vivo portion of the sensor to the in vivo portion of the sensor to increase oxygen availability to the enzyme. The oxygen conduit can be formed as a part of the coating (insulating) material or can be a separate conduit associated with the assembly of wires that forms the sensor.

Porous Biointerface Materials

In alternative embodiments, the distal portion 42 includes a porous material disposed over some portion thereof, which modifies the host's tissue response to the sensor. In some embodiments, the porous material surrounding the sensor advantageously enhances and extends sensor performance and lifetime in the short term by slowing or reducing cellular migration to the sensor and associated degradation that would otherwise be caused by cellular invasion if the sensor were directly exposed to the in vivo environment. Alternatively, the porous material can provide stabilization of the sensor via tissue ingrowth into the porous material in the long term. Suitable porous materials include silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, polysulfones and block copolymers thereof including, for example, di-block, tri-block, alternating, random and graft copolymers, as well as metals, ceramics, cellulose, hydrogel polymers, poly (2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(1-lysine), poly (L-lactic acid), hydroxyethylmetharcrylate, hydroxyapeptite, alumina, zirconia, carbon fiber, aluminum, calcium phosphate, titanium, titanium alloy, nintinol, stainless steel, and CoCr alloy, or the like, such as are described in co-pending U.S. patent application Ser. No. 10/842,716, filed May 10, 2004 and entitled, "BIOINTERFACE MEMBRANES INCORPORATING BIOACTIVE AGENTS" and U.S. patent application Ser. No. 10/647,065 filed Aug. 22, 2003 and entitled "POROUS MEMBRANES FOR USE WITH IMPLANTABLE DEVICES."

In some embodiments, the porous material surrounding the sensor provides unique advantages in the short term (e.g., one to 14 days) that can be used to enhance and extend sensor performance and lifetime. However, such materials can also provide advantages in the long term too (e.g., greater than 14 days). Particularly, the in vivo portion of the sensor (the portion of the sensor that is implanted into the host's tissue) is encased (partially or fully) in a porous material. The porous material can be wrapped around the sensor (for example, by wrapping the porous material around the sensor or by inserting the sensor into a section of porous material sized to receive the sensor). Alternately, the porous material can be deposited on the sensor (for example, by electrospinning of a polymer directly thereon). In yet other alternative embodiments, the sensor is inserted into a selected section of porous biomaterial. Other methods for surrounding the in vivo portion of the sensor with a porous material can also be used as is appreciated by one skilled in the art.

The porous material surrounding the sensor advantageously slows or reduces cellular migration to the sensor and associated degradation that would otherwise be caused by cellular invasion if the sensor were directly exposed to the in vivo environment. Namely, the porous material provides a barrier that makes the migration of cells towards the sensor more tortuous and therefore slower (providing short term advantages). It is believed that this reduces or slows the sensitivity loss normally observed in a short-term sensor over time.

In an embodiment wherein the porous material is a high oxygen solubility material, such as porous silicone, the high oxygen solubility porous material surrounds some of or the entire in vivo portion 42 of the sensor. High oxygen solubility materials are materials that dynamically retain a high availability of oxygen that can be used to compensate for the local oxygen deficit during times of transient ischemia (e.g., silicone and fluorocarbons). It is believed that some signal noise normally seen by a conventional sensor can be attributed to an oxygen deficit. In one exemplary embodiment, porous silicone surrounds the sensor and thereby effectively increases the concentration of oxygen local (proximal) to the sensor. Thus, an increase in oxygen availability proximal to the sensor as achieved by this embodiment ensures that an excess of oxygen over glucose is provided to the sensor; thereby reducing the likelihood of oxygen limited reactions therein. Accordingly, by providing a high oxygen solubility material (e.g., porous silicone) surrounding the in vivo portion of the sensor, it is believed that increased oxygen availability, reduced signal noise, longevity, and ultimately enhanced sensor performance can be achieved.

Bioactive Agents

In some alternative embodiments, a bioactive agent is incorporated into the above described porous material and/or membrane system, such as is described in co-pending U.S. patent application Ser. No. 10/842,716, which diffuses out into the environment adjacent to the sensing region. Additionally or alternately, a bioactive agent can be administered locally at the exit-site or implantation-site. Suitable bioactive agents are those that modify the host's tissue response to the sensor, for example anti-inflammatory agents, anti-infective agents, anesthetics, inflammatory agents, growth factors, immunosuppressive agents, antiplatelet agents, anti-coagulants, anti-proliferates, ACE inhibitors, cytotoxic agents, anti-barrier cell compounds, vascularization-inducing compounds, anti-sense molecules, or mixtures thereof, such as are described in more detail in co-pending U.S. patent application Ser. No. 10/842,716.

In embodiments wherein the porous material is designed to enhance short-term (e.g., between about 1 and 14 days) lifetime or performance of the sensor, a suitable bioactive agent can be chosen to ensure that tissue ingrowth does not substantially occur within the pores of the porous material. Namely, by providing a tissue modifying bioactive agent, such as an anti-inflammatory agent (for example, Dexamethasone), substantially tissue ingrowth can be inhibited, at least in the short term, in order to maintain sufficient glucose transport through the pores of the porous material to maintain a stable sensitivity.

In embodiments wherein the porous material is designed to enhance long-term (e.g., between about a day to a year or more) lifetime or performance of the sensor, a suitable bioactive agent, such as a vascularization-inducing compound or anti-barrier cell compound, can be chosen to encourage tissue ingrowth without barrier cell formation.

In some alternative embodiments, the in vivo portion of the sensor is designed with porosity there through, for example, a design wherein the sensor wires are configured in a mesh, loose helix configuration (namely, with spaces between the wires), or with micro-fabricated holes there through. Porosity within the sensor modifies the host's tissue response to the sensor, because tissue ingrowth into and/or through the in vivo portion of the sensor increases stability of the sensor and/or improves host acceptance of the sensor, thereby extending the lifetime of the sensor in vivo.

In some alternative embodiments, the sensor is manufactured partially or wholly using a continuous reel-to-reel process, wherein one or more manufacturing steps are automated. In such embodiments, a manufacturing process can be provided substantially without the need for manual mounting and fixturing steps and substantially without the need human interaction. A process can be utilized wherein a plurality of sensors of the preferred embodiments, including the electrodes, insulator, and membrane system, are continuously manufactured in a semi-automated or automated process.

In one embodiment, a plurality of twisted pairs are continuously formed into a coil, wherein a working electrode is coated with an insulator material around which a plurality of reference electrodes are wound. The plurality of twisted pairs are preferably indexed and subsequently moved from one station to the next whereby the membrane system is serially deposited according to the preferred embodiments. Preferably, the coil is continuous and remains as such during the entire sensor fabrication process, including winding of the electrodes, insulator application, and membrane coating processes. After drying of the membrane system, each individual sensor is cut from the continuous coil.

A continuous reel-to-reel process for manufacturing the sensor eliminates possible sensor damage due to handling by eliminating handling steps, and provides faster manufacturing due to faster trouble shooting by isolation when a product fails. Additionally, a process run can be facilitated because of elimination of steps that would otherwise be required (e.g., steps in a manual manufacturing process.) Finally, increased or improved product consistency due to consistent processes within a controlled environment can be achieved in a machine or robot driven operation.

In one alternative embodiment, a continuous manufacturing process is contemplated that utilizes physical vapor deposition in a vacuum to form the sensor. Physical vapor deposition can be used to coat one or more insulating layers onto the electrodes, and further can be used to deposit the membrane system thereon. While not wishing to be bound by theory, it is believed that by implementing physical vapor deposition to form some portions or the entire sensor of the preferred embodiments, simplified manufacturing, consistent deposition, and overall increased reproducibility can be achieved.

Applicator

FIG. 6 is an exploded side view of an applicator, showing the components that enable sensor and needle insertion. In this embodiment, the applicator 12 includes an applicator body 18 that aides in aligning and guiding the applicator components. Preferably, the applicator body 18 includes an applicator body base 60 that matingly engages the mounting unit 14 and an applicator body cap 62 that enables appropriate relationships (for example, stops) between the applicator components.

The guide tube subassembly 20 includes a guide tube carrier 64 and a guide tube 66. In some embodiments, the guide tube is a cannula. The guide tube carrier 64 slides along the applicator body 18 and maintains the appropriate relative position of the guide tube 66 during insertion and subsequent retraction. For example, prior to and during insertion of the sensor, the guide tube 66 extends through the contact subassembly 26 to maintain an opening that enables easy insertion of the needle there through (see FIGS. 7A to 7D). During retraction of the sensor, the guide tube subassembly 20 is pulled back, engaging with and causing the needle and associated moving components to retract back into the applicator 12 (See FIGS. 7C and 7D).

A needle subassembly 68 is provided that includes a needle carrier 70 and needle 72. The needle carrier 70 cooperates with the other applicator components and carries the needle 72 between its extended and retracted positions. The needle can be of any appropriate size that can encompass the sensor 32 and aid in its insertion into the host. Preferred sizes include from about 32 gauge or less to about 18 gauge or more, more preferably from about 28 gauge to about 25 gauge, to provide a comfortable insertion for the host. Referring to the inner diameter of the needle, approximately 0.006 inches to approximately 0.023 inches is preferable, and 0.013 inches is most preferable. The needle carrier 70 is configured to engage with the guide tube carrier 64, while the needle 72 is configured to slidably nest within the guide tube 66, which allows for easy guided insertion (and retraction) of the needle through the contact subassembly 26.

A push rod subassembly 74 is provided that includes a push rod carrier 76 and a push rod 78. The push rod carrier 76 cooperates with other applicator components to ensure that the sensor is properly inserted into the host's skin, namely the push rod carrier 76 carries the push rod 78 between its extended and retracted positions. In this embodiment, the push rod 78 is configured to slidably nest within the needle 72, which allows for the sensor 32 to be pushed (released) from the needle 72 upon retraction of the needle, which is described in more detail with reference to FIGS. 7A through 7D. In some embodiments, a slight bend or serpentine shape is designed into or allowed in the sensor in order to maintain the sensor within the needle by interference. While not wishing to be bound by theory, it is believed that a slight friction fit of the sensor within the needle minimizes motion of the sensor during withdrawal of the needle and maintains the sensor within the needle prior to withdrawal of the needle.

A plunger subassembly 22 is provided that includes a plunger 80 and plunger cap 82. The plunger subassembly 22 cooperates with other applicators components to ensure proper insertion and subsequent retraction of the applicator components. In this embodiment, the plunger 80 is configured to engage with the push rod to ensure the sensor remains extended (namely, in the host) during retraction, such as is described in more detail with reference to FIG. 7C.

Sensor Insertion

Figure 7A:
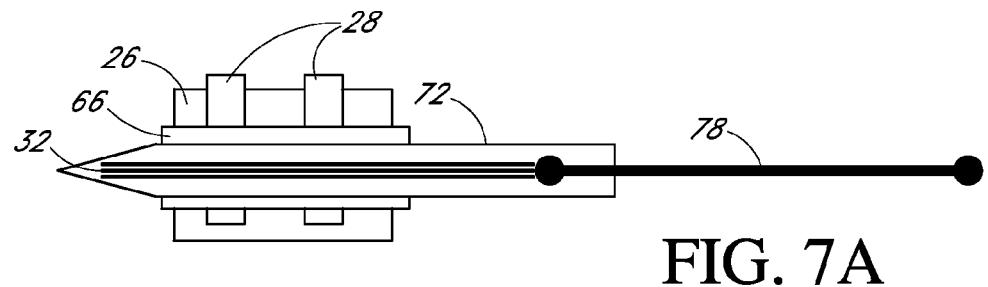
FIGS. 7A to 7D are schematic side cross-sectional views that illustrate applicator components and their cooperating relationships.
Figure 7B:
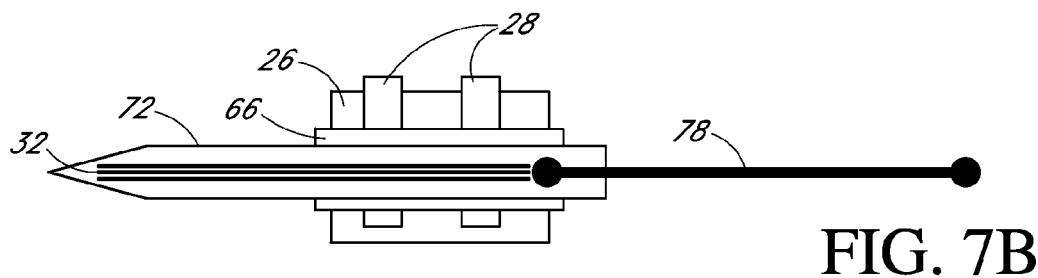
Figure 7C:
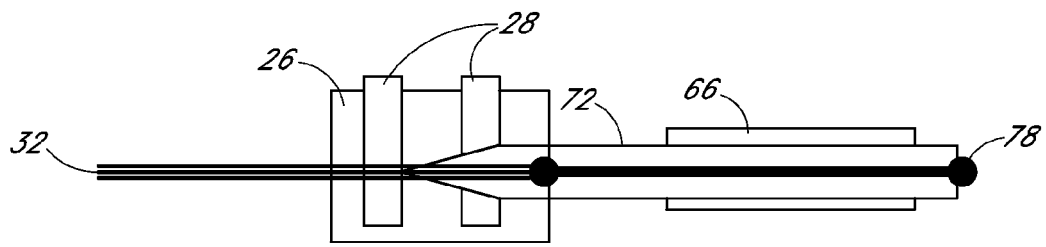
Figure 7D:
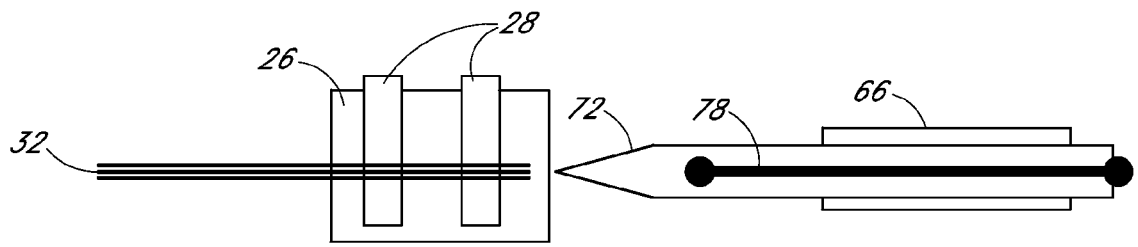

FIGS. 7A through 7D are schematic side cross-sectional views that illustrate the applicator components and their cooperating relationships at various stages of sensor insertion. FIG. 7A illustrates the needle and sensor loaded prior to sensor insertion. FIG. 7B illustrates the needle and sensor after sensor insertion. FIG. 7C illustrates the sensor and needle during needle retraction. FIG. 7D illustrates the sensor remaining within the contact subassembly after needle retraction. Although the embodiments described herein suggest manual insertion and/or retraction of the various components, automation of one or more of the stages can also be employed. For example, spring-loaded mechanisms that can be triggered to automatically insert and/or retract the sensor, needle, or other cooperative applicator components can be implemented.

Referring to FIG. 7A, the sensor 32 is shown disposed within the needle 72, which is disposed within the guide tube 66. In this embodiment, the guide tube 66 is provided to maintain an opening within the contact subassembly 26 and/or contacts 28 to provide minimal friction between the needle 72 and the contact subassembly 26 and/or contacts 28 during insertion and retraction of the needle 72. However, the guide tube is an optional component, which can be advantageous in some embodiments wherein the contact subassembly 26 and/or the contacts 28 are formed from an elastomer or other material with a relatively high friction coefficient, and which can be omitted in other embodiments wherein the contact subassembly 26 and or the contacts 28 are formed from a material with a relatively low friction coefficient (for example, hard plastic or metal). A guide tube, or the like, can be preferred in embodiments wherein the contact subassembly 26 and/or the contacts 28 are formed from a material designed to frictionally hold the sensor 32 (see FIG. 7D), for example, by the relaxing characteristics of an elastomer, or the like. In these embodiments, the guide tube is provided to ease insertion of the needle through the contacts, while allowing for a frictional hold of the contacts on the sensor 32 upon subsequent needle retraction. Stabilization of the sensor in or on the contacts 28 is described in more detail with reference to FIG. 7D and following. Although FIG. 7A illustrates the needle and sensor inserted into the contacts subassembly as the initial loaded configuration, alternative embodiments contemplate a step of loading the needle through the guide tube 66 and/or contacts 28 prior to sensor insertion.

Referring to FIG. 7B, the sensor 32 and needle 72 are shown in an extended position. In this stage, the pushrod 78 has been forced to a forward position, for example by pushing on the plunger shown in FIG. 6, or the like. The plunger 22 (FIG. 6) is designed to cooperate with other of the applicator components to ensure that sensor 32 and the needle 72 extend together to a forward position (as shown); namely, the push rod 78 is designed to cooperate with other of the applicator components to ensure that the sensor 32 maintains the forward position simultaneously within the needle 72.

Referring to FIG. 7C, the needle 72 is shown during the retraction process. In this stage, the push rod 78 is held in its extended (forward) position in order to maintain the sensor 32 in its extended (forward) position until the needle 72 has substantially fully retracted from the contacts 28. Simultaneously, the cooperating applicator components retract the needle 72 and guide tube 66 backward by a pulling motion (manual or automated) thereon. In preferred embodiments, the guide tube carrier 64 (FIG. 6) engages with cooperating applicator components such that a backward (retraction) motion applied to the guide tube carrier retracts the needle 72 and guide tube 66, without (initially) retracting the push rod 78. In an alternative embodiment, the push rod 78 can be omitted and the sensor 32 held it its forward position by a cam, elastomer, or the like, which is in contact with a portion of the sensor while the needle moves over another portion of the sensor. One or more slots can be cut in the needle to maintain contact with the sensor during needle retraction.

Referring to FIG. 7D, the needle 72, guide tube 66, and push rod 78 are all retracted from contact subassembly 26, leaving the sensor 32 disposed therein. The cooperating applicator components are designed such that when the needle 72 has substantially cleared from the contacts 28 and/or contact subassembly 26, the push rod 78 is retracted along with the needle 72 and guide tube 66. The applicator 12 can then be released (manually or automatically) from the contacts 28, such as is described in more detail elsewhere herein, for example with reference to FIGS. 8C and 9A.

The preferred embodiments are generally designed with elastomeric contacts to ensure a retention force that retains the sensor 32 within the mounting unit 14 and to ensure stable electrical connection of the sensor 32 and its associated contacts 28. Although the illustrated embodiments and associated text describe the sensor 32 extending through the contacts 28 to form a friction fit therein, a variety of alternatives are contemplated. In one alternative embodiment, the sensor is configured to be disposed adjacent to the contacts (rather than between the contacts). The contacts can be constructed in a variety of known configurations, for example, metallic contacts, cantilevered fingers, pogo pins, or the like, which are configured to press against the sensor after needle retraction.

The illustrated embodiments are designed with coaxial contacts 28; namely, the contacts 28 are configured to contact the working and reference electrodes 44, 46 axially along the proximal portion 40 of the sensor 32 (see FIG. 5A). As shown in FIG. 5A, the working electrode 44 extends farther than the reference electrode 46, which allows coaxial connection of the electrodes 44, 46 with the contacts 28 at locations spaced along the proximal of the sensor (see also FIGS. 9B and 10B). Although the illustrated embodiments employ a coaxial design, other designs are contemplated within the scope of the preferred embodiments. For example, the reference electrode can be positioned substantially adjacent to (but spaced apart from) the working electrode at the proximal portion of the sensor. In this way, the contacts 28 can be designed side-by-side rather than co-axially along the axis of the sensor.

Figure 8A:
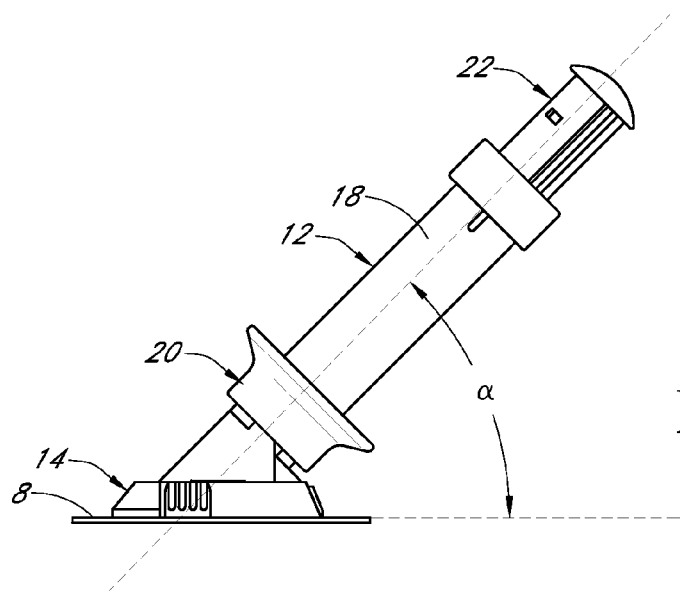
FIG. 8A is a side view of an applicator matingly engaged to a mounting unit, prior to sensor insertion.
Figure 8B:
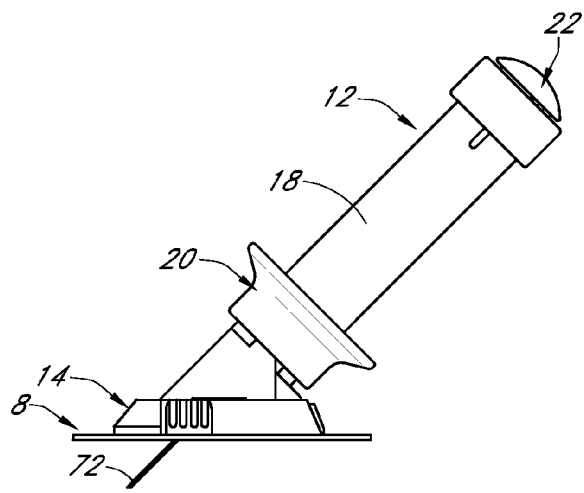
FIG. 8B is a side view of a mounting unit and applicator after the plunger subassembly has been pushed, extending the needle and sensor from the mounting unit.
Figure 8C:
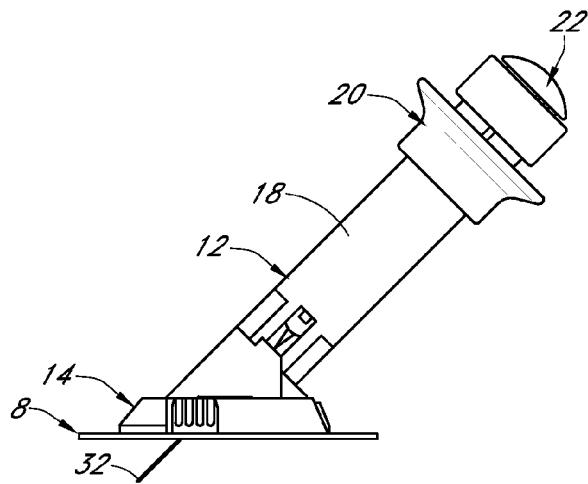
FIG. 8C is a side view of a mounting unit and applicator after the guide tube subassembly has been retracted, retracting the needle back into the applicator.

FIGS. 8A to 8C are side views of an applicator and mounting, showing various stages of sensor insertion. FIG. 8A is a side view of the applicator matingly engaged to the mounting unit prior to sensor insertion. FIG. 8B is a side view of the mounting unit and applicator after the plunger subassembly has been pushed, extending the needle and sensor from the mounting unit (namely, through the host's skin). FIG. 8C is a side view of the mounting unit and applicator after the guide tube subassembly has been retracted, retracting the needle back into the applicator. Although the drawings and associated text illustrate and describe embodiments wherein the applicator is designed for manual insertion and/or retraction, automated insertion and/or retraction of the sensor/needle, for example, using spring-loaded components, can alternatively be employed.

The preferred embodiments advantageously provide a system and method for easy insertion of the sensor and subsequent retraction of the needle in a single push-pull motion. Because of the mechanical latching system of the applicator, the user provides a continuous force on the plunger cap 82 and guide tube carrier 64 that inserts and retracts the needle in a continuous motion. When a user grips the applicator, his or her fingers grasp the guide tube carrier 64 while his or her thumb (or another finger) is positioned on the plunger cap 82. The user squeezes his or her fingers and thumb together continuously, which causes the needle to insert (as the plunger slides forward) and subsequently retract (as the guide tube carrier slides backward) due to the system of latches located within the applicator (FIGS. 6 to 8) without any necessary change of grip or force, leaving the sensor implanted in the host. In some embodiments, a continuous torque, when the applicator components are configured to rotatingly engage one another, can replace the continuous force. Some prior art sensors, in contrast to the sensors of the preferred embodiments, suffer from complex, multi-step, or multi-component insertion and retraction steps to insert and remove the needle from the sensor system.

FIG. 8A shows the mounting unit and applicator in the ready position. The sensor system can be shipped in this configuration, or the user can be instructed to mate the applicator 12 with the mounting unit 14 prior to sensor insertion. The insertion angle α is preferably fixed by the mating engagement of the applicator 12. In the illustrated embodiment, the insertion angle α is fixed in the applicator 12 by the angle of the applicator body base 60 with the shaft of the applicator body 18. However, a variety of systems and methods of ensuring proper placement can be implemented. Proper placement ensures that at least a portion of the sensor 32 extends below the dermis of the host upon insertion. In alternative embodiments, the sensor system 10 is designed with a variety of adjustable insertion angles. A variety of insertion angles can be advantageous to accommodate a variety of insertion locations and/or individual dermis configurations (for example, thickness of the dermis). In preferred embodiments, the insertion angle α is from about 0 to about 90 degrees, more preferably from about 30 to about 60 degrees, and even more preferably about 45 degrees.

In practice, the mounting unit is placed at an appropriate location on the host's skin, for example, the skin of the arm, thigh, or abdomen. Thus, removing the backing layer 9 from the adhesive pad 8 and pressing the base portion of the mounting unit on the skin adheres the mounting unit to the host's skin.

FIG. 8B shows the mounting unit and applicator after the needle 72 has been extended from the mounting unit 14 (namely, inserted into the host) by pushing the push rod subassembly 22 into the applicator 12. In this position, the sensor 32 is disposed within the needle 72 (namely, in position within the host), and held by the cooperating applicator components. In alternative embodiments, the mounting unit and/or applicator can be configured with the needle/sensor initially extended. In this way, the mechanical design can be simplified and the plunger-assisted insertion step can be eliminated or modified. The needle can be simply inserted by a manual force to puncture the host's skin, and only one (pulling) step is required on the applicator, which removes the needle from the host's skin.

FIG. 8C shows the mounting unit and applicator after the needle 72 has been retracted into the applicator 12, exposing the sensor 32 to the host's tissue. During needle retraction, the push rod subassembly maintains the sensor in its extended position (namely, within the host). In preferred embodiments, retraction of the needle irreversibly locks the needle within the applicator so that it cannot be accidentally and/or intentionally released, reinserted, or reused. The applicator is preferably configured as a disposable device to reduce or eliminate a possibility of exposure of the needle after insertion into the host. However a reusable or reloadable applicator is also contemplated in some alternative embodiments. After needle retraction, the applicator 12 can be released from the mounting unit, for example, by pressing the release latch(es) 30, and the applicator disposed of appropriately. In alternative embodiments, other mating and release configurations can be implemented between the mounting unit and the applicator, or the applicator can automatically release from the mounting unit after sensor insertion and subsequent needle retraction. In one alternative embodiment, a retention hold (e.g., ball and detent configuration) holds and releases the electronics unit (or applicator).

In one alternative embodiment, the mounting unit is configured to releasably mate with the applicator and electronics unit, such that when the applicator is releasably mated to the mounting unit (e.g., after sensor insertion), the electronics unit is configured to slide into the mounting unit, thereby triggering release of the applicator and simultaneous mating of the electronics unit to the mounting unit. Cooperating mechanical components, for example, sliding ball and detent type configurations, can be used to accomplish the simultaneous mating of electronics unit and release of the applicator.

In some embodiments, the sensor 32 exits the base of the mounting unit 14 at a location distant from an edge of the base. In some embodiments, the sensor 32 exits the base of the mounting unit 14 at a location substantially closer to the center than the edges thereof. While not wishing to be bound by theory, it is believed that by providing an exit port for the sensor 32 located away from the edges, the sensor 32 can be protected from motion between the body and the mounting unit, snagging of the sensor by an external source, and/or environmental contaminants that can migrate under the edges of the mounting unit. In some embodiments, the sensor exits the mounting unit away from an outer edge of the device. In some alternative embodiments, however, the sensor exits the mounting unit 14 at an edge or near an edge of the device. In some embodiments, the mounting unit is configured such that the exit port (location) of the sensor is adjustable; thus, in embodiments wherein the depth of the sensor insertion is adjustable, six-degrees of freedom can thereby be provided.

Extensible Adhesive pad

In certain embodiments, an adhesive pad is used with the sensor system. A variety of design parameters are desirable when choosing an adhesive pad for the mounting unit. For example: 1) the adhesive pad can be strong enough to maintain full contact at all times and during all movements (devices that release even slightly from the skin have a greater risk of contamination and infection), 2) the adhesive pad can be waterproof or water permeable such that the host can wear the device even while heavily perspiring, showering, or even swimming in some cases, 3) the adhesive pad can be flexible enough to withstand linear and rotational forces due to host movements, 4) the adhesive pad can be comfortable for the host, 5) the adhesive pad can be easily releasable to minimize host pain, 6) and/or the adhesive pad can be easily releasable so as to protect the sensor during release. Unfortunately, these design parameters are difficult to simultaneously satisfy using known adhesive pads, for example, strong medical adhesive pads are available but are usually non-precise (for example, requiring significant "ripping" force during release) and can be painful during release due to the strength of their adhesion.

Figure 9A:
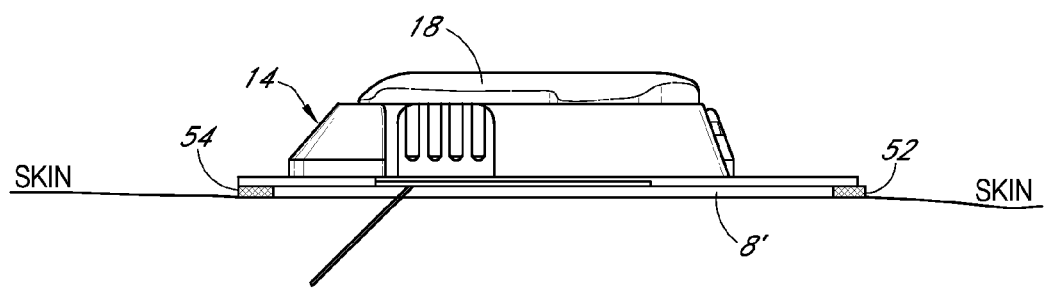
FIGS. 9A to 9C are side views of an applicator and mounting unit, showing stages of sensor insertion.

Therefore, the preferred embodiments provide an adhesive pad 8' for mounting the mounting unit onto the host, including a sufficiently strong medical adhesive pad that satisfies one or more strength and flexibility requirements described above, and further provides a for easy, precise and pain-free release from the host's skin. FIG. 9A is a side view of the sensor assembly, illustrating the sensor implanted into the host with mounting unit adhered to the host's skin via an adhesive pad in one embodiment. Namely, the adhesive pad 8' is formed from an extensible material that can be removed easily from the host's skin by stretching it lengthwise in a direction substantially parallel to (or up to about 35 degrees from) the plane of the skin. It is believed that this easy, precise, and painless removal is a function of both the high extensibility and easy stretchability of the adhesive pad.

Figure 9B:
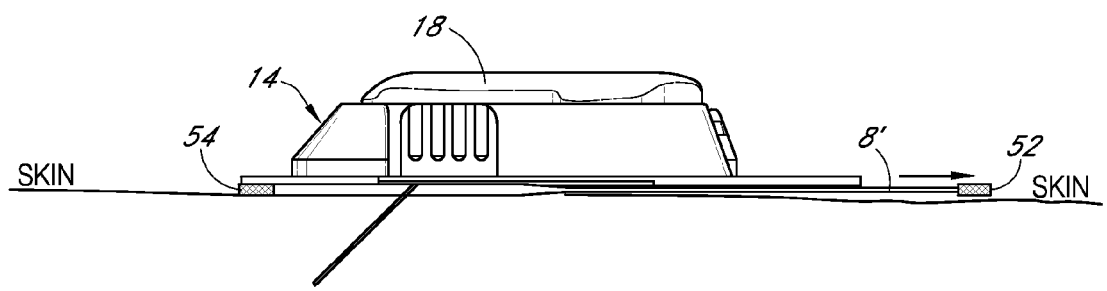
Figure 9C:
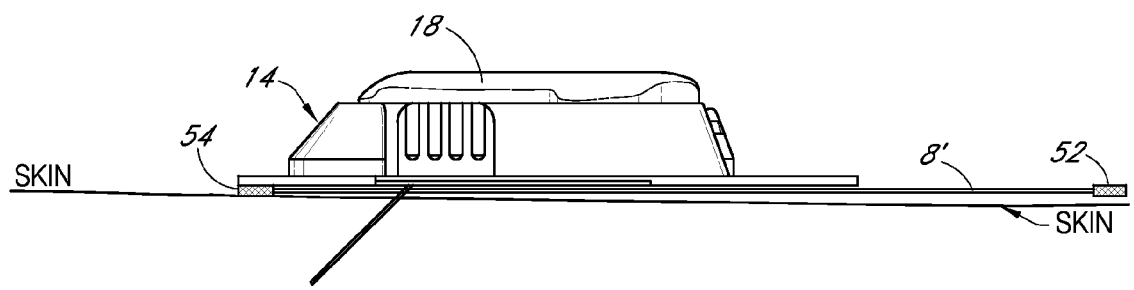

In one embodiment, the extensible adhesive pad includes a polymeric foam layer or is formed from adhesive pad foam. It is believed that the conformability and resiliency of foam aids in conformation to the skin and flexibility during movement of the skin. In another embodiment, a stretchable solid adhesive pad, such as a rubber-based or an acrylate-based solid adhesive pad can be used. In another embodiment, the adhesive pad comprises a film, which can aid in increasing load bearing strength and rupture strength of the adhesive pad FIGS. 9B to 9C illustrate initial and continued release of the mounting unit from the host's skin by stretching the extensible adhesive pad in one embodiment. To release the device, the backing adhesive pad is pulled in a direction substantially parallel to (or up to about 35 degrees from) the plane of the device. Simultaneously, the extensible adhesive pad stretches and releases from the skin in a relatively easy and painless manner.

In one implementation, the mounting unit is bonded to the host's skin via a single layer of extensible adhesive pad 8', which is illustrated in FIGS. 9A to 9C. The extensible adhesive pad includes a substantially non-extensible pull-tab 52, which can include a light adhesive pad layer that allows it to be held on the mounting unit 14 prior to release. Additionally, the adhesive pad can further include a substantially non-extensible holding tab 54, which remains attached to the mounting unit during release stretching to discourage complete and/or uncontrolled release of the mounting unit from the skin.

In one alternative implementation, the adhesive pad 8' includes two-sides, including the extensible adhesive pad and a backing adhesive pad (not shown). In this embodiment, the backing adhesive pad is bonded to the mounting unit's back surface 25 while the extensible adhesive pad 8' is bonded to the host's skin. Both adhesive pads provide sufficient strength, flexibility, and waterproof or water permeable characteristics appropriate for their respective surface adhesion. In some embodiments, the backing and extensible adhesive pads are particularly designed with an optimized bond for their respective bonding surfaces (namely, the mounting unit and the skin).

In another alternative implementation, the adhesive pad 8' includes a double-sided extensible adhesive pad surrounding a middle layer or backing layer (not shown). The backing layer can comprise a conventional backing film or can be formed from foam to enhance comfort, conformability, and flexibility. Preferably, each side of the double-sided adhesive pad is respectively designed for appropriate bonding surface (namely, the mounting unit and skin). A variety of alternative stretch-release configurations are possible. Controlled release of one or both sides of the adhesive pad can be facilitated by the relative lengths of each adhesive pad side, by incorporation of a non-adhesive pad zone, or the like.

FIGS. 10A and 10B are perspective and side cross-sectional views, respectively, of the mounting unit immediately following sensor insertion and release of the applicator from the mounting unit. In one embodiment, such as illustrated in FIGS. 10A and 10B, the contact subassembly 26 is held in its insertion position, substantially at the insertion angle α of the sensor. Maintaining the contact subassembly 26 at the insertion angle α during insertion enables the sensor 32 to be easily inserted straight through the contact subassembly 26. The contact subassembly 26 further includes a hinge 38 that allows movement of the contact subassembly 26 from an angled to a flat position. The term "hinge," as used herein, is a broad term and is used in its ordinary sense, including, without limitation, a mechanism that allows articulation of two or more parts or portions of a device. The term is broad enough to include a sliding hinge, for example, a ball and detent type hinging mechanism.

Although the illustrated embodiments describe a fixed insertion angle designed into the applicator, alternative embodiments can design the insertion angle into other components of the system. For example, the insertion angle can be designed into the attachment of the applicator with the mounting unit, or the like. In some alternative embodiments, a variety of adjustable insertion angles can be designed into the system to provide for a variety of host dermis configurations.

FIG. 10B illustrates the sensor 32 extending from the mounting unit 14 by a preselected distance, which defines the depth of insertion of the sensor into the host. The dermal and subcutaneous make-up of animals and humans is variable and a fixed depth of insertion may not be appropriate for all implantations. Accordingly, in an alternative embodiment, the distance that the sensor extends from the mounting unit is adjustable to accommodate a variety of host body-types. For example, the applicator 12 can be designed with a variety of adjustable settings, which control the distance that the needle 72 (and therefore the sensor 32) extends upon sensor insertion. One skilled in the art appreciates a variety of means and mechanisms can be employed to accommodate adjustable sensor insertion depths, which are considered within the scope of the preferred embodiments. The preferred insertion depth is from about 0.1 mm or less to about 2 cm or more, preferably from about 0.15, 0.2, 0.25, 0.3, 0.35, 0.4, or 0.45 mm to about 0.5, 0.6, 0.7, 0.8, 0.9, 1, 1.1, 1.2, 1.3, 1.4, 1.5, 1.6, 1.7, 1.8, or 1.9 cm.

FIGS. 11A and 11B are perspective and side cross-sectional views, respectively, of the mounting unit after articulating the contact subassembly to its functional position (which is also referred to as an inserted, implanted, or sensing position). The hinge 38 enables the contact subassembly 26 to tilt from its insertion position (FIG. 10) to its functional position (FIG. 11) by pressing downward on the contact subassembly, for example. Certain embodiments provide this pivotal movement via two separate pieces (the contact subassembly 26 and the mounting unit 14 connected by a hinge, for example, a mechanical or adhesive pad joint or hinge. A variety of pivoting, articulating, and/or hinging mechanisms can be employed with the sensors of preferred embodiments. For example, the hinge can be formed as a part of the contact subassembly 26. The contact subassembly can be formed from a flexible piece of material (such as silicone, urethane rubber, or other flexible or elastomeric material), wherein the material is sufficiently flexible to enable bending or hinging of the contact subassembly from an angle appropriate for insertion (FIGS. 10A and 10B) to a lower functional configuration (FIGS. 11A and 11B).

The relative pivotal movement of the contact subassembly is advantageous, for example, for enabling the design of a low profile device while providing support for an appropriate needle insertion angle. In its insertion position, the sensor system is designed for easy sensor insertion while forming a stable electrical connection with the associated contacts 28. In its functional position, the sensor system maintains a low profile for convenience, comfort, and discreetness during use. Thus, the sensor systems of preferred embodiments are advantageously designed with a hinging configuration to provide an optimum guided insertion angle while maintaining a low profile device during sensor use.

In some embodiments, a shock-absorbing member or feature is incorporated into the design of the sensor and configured to absorb movement of the in vivo and/or ex vivo portion of the sensor. Conventional analyte sensors can suffer from motion-related artifact associated with host movement when the host is using the device. For example, when a transcutaneous analyte sensor is inserted into the host, various movements on the sensor (for example, relative movement between the in vivo portion and the ex vivo portion and/or movement within the host) create stresses on the device and can produce noise in the sensor signal. Accordingly in some embodiments, a shock-absorbing member is located on the sensor/mounting unit in a location that absorbs stresses associated with the above-described movement.

In the preferred embodiments, the sensor 32 bends from a substantially straight to substantially bent configuration upon pivoting of the contact subassembly from the insertion to functional position. The substantially straight sensor configuration during insertion advantageously provides ease of sensor insertion, while the substantial bend in the sensor in its functional position advantageously provides stability on the proximal end of the sensor with flexibility/mobility on the distal end of the sensor. Additionally, motion within the mounting unit (e.g., caused by external forces to the mounting unit, movement of the skin, and the like) does not substantially translate to the in vivo portion of the sensor. Namely, the bend formed within the sensor 32 functions to break column strength, causing flexion that effectively absorbs movements on the sensor during use. Additionally, the sensor can be designed with a length such that when the contact subassembly 26 is pivoted to its functional position (FIG. 10B), the sensor pushes forward and flexes, allowing it to absorb motion between the in vivo and ex vivo portions of the sensor. It is believed that both of the above advantages minimize motion artifact on the sensor signal and/or minimize damage to the sensor caused by movement, both of which (motion artifact and damage) have been observed in conventional transcutaneous sensors.

In some alternative embodiments, the shock-absorbing member can be an expanding and contracting member, such as a spring, accordion, telescoping, or bellows-type device. In general, the shock absorbing member can be located such that relative movement between the sensor, the mounting unit, and the host is absorbed without (or minimally) affecting the connection of the sensor to the mounting unit and/or the sensor stability within the implantation site; for example, the shock-absorbing member can be formed as a part of or connected to the sensor 32.

Figure 12A:
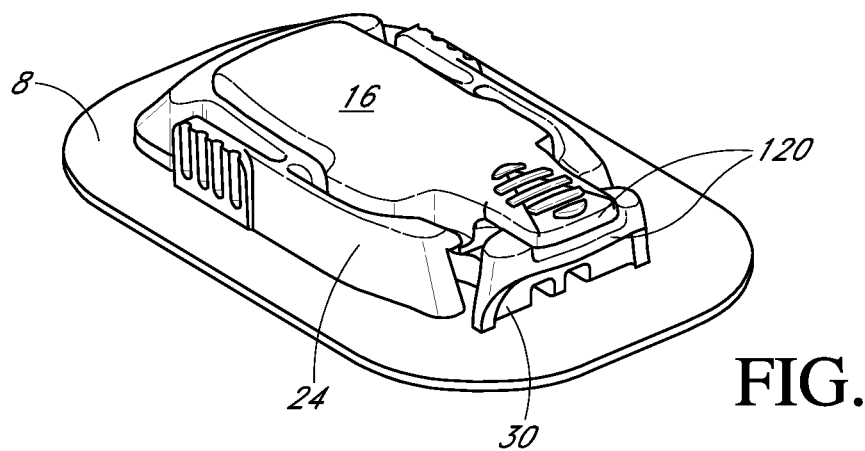
FIGS. 12A to 12C are perspective and side views, respectively, of the sensor system showing the sensor, mounting unit, and electronics unit in their functional positions.
Figure 12B:
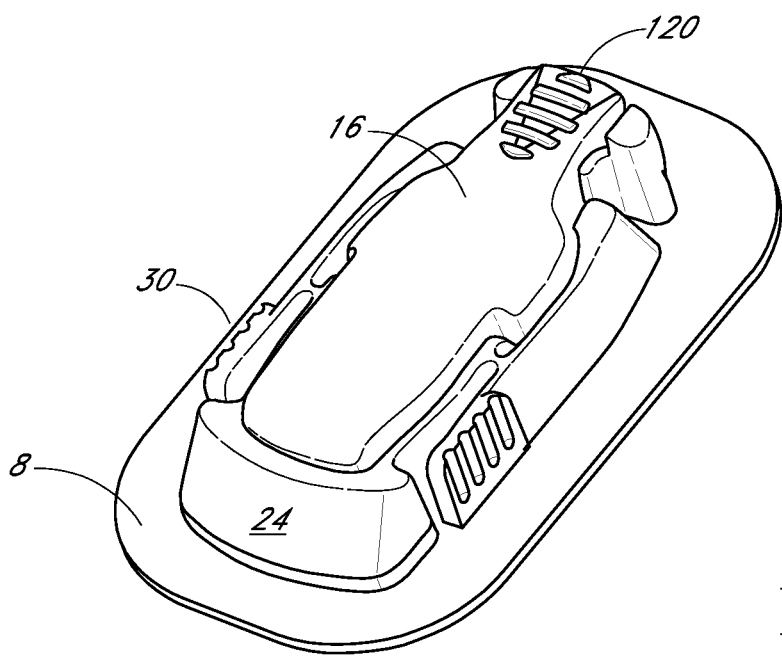
Figure 12C:
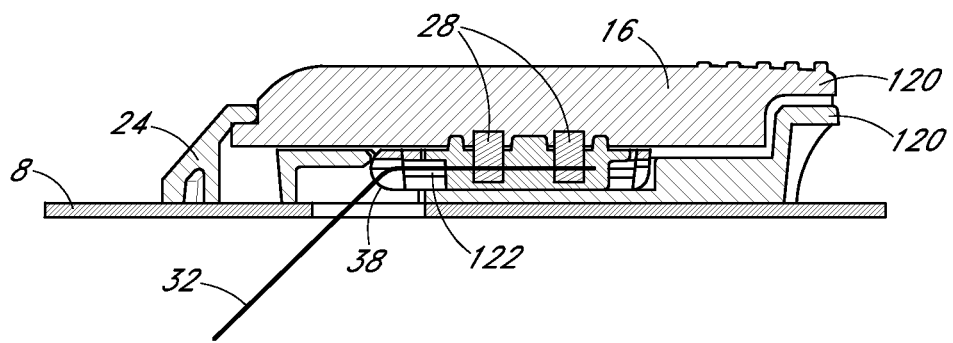

FIGS. 12A to 12C are perspective and side views of a sensor system including the mounting unit 14 and electronics unit 16 attached thereto. After sensor insertion, the transcutaneous analyte sensor system 10 measures a concentration of an analyte or a substance indicative of the concentration or presence of the analyte as described above. Although the examples are directed to a glucose sensor, the analyte sensor can be a sensor capable of determining the level of any suitable analyte in the body, for example, oxygen, lactase, insulin, hormones, cholesterol, medicaments, viruses, or the like. Once the electronics unit 16 is connected to the mounting unit 14, the sensor 32 is able to measure levels of the analyte in the host.

Detachable connection between the mounting unit 14 and electronics unit 16 provides improved manufacturability, namely, the relatively inexpensive mounting unit 14 can be disposed of when replacing the sensor system after its usable life, while the relatively more expensive electronics unit 16 can be reusable with multiple sensor systems. In certain embodiments, the electronics unit 16 is configured with programming, for example, initialization, calibration reset, failure testing, or the like, each time it is initially inserted into the cavity and/or each time it initially communicates with the sensor 32. However, an integral (non-detachable) electronics unit can be configured as is appreciated by one skilled in the art.

Referring to the mechanical fit between the mounting unit 14 and the electronics unit 16 (and/or applicator 12), a variety of mechanical joints are contemplated, for example, snap fit, interference fit, or slide fit. In the illustrated embodiment of FIGS. 12A to 12C, tabs 120 are provided on the mounting unit 14 and/or electronics unit 16 that enable a secure connection there between. The tabs 120 of the illustrated embodiment can improve ease of mechanical connection by providing alignment of the mounting unit and electronics unit and additional rigid support for force and counter force by the user (e.g., fingers) during connection. However, other configurations with or without guiding tabs are contemplated, such as illustrated in FIGS. 10 and 11, for example.

In some circumstances, a drift of the sensor signal can cause inaccuracies in sensor performance and/or require re-calibration of the sensor. Accordingly, it can be advantageous to provide a sealant, whereby moisture (e.g., water and water vapor) cannot substantially penetrate to the sensor and its connection to the electrical contacts. The sealant described herein can be used alone or in combination with the sealing member 36 described in more detail above, to seal the sensor from moisture in the external environment.

Preferably, the sealant fills in holes, crevices, or other void spaces between the mounting unit 14 and electronics unit 16 and/or around the sensor 32 within the mounting unit 32. For example, the sealant can surround the sensor in the portion of the sensor 32 that extends through the contacts 28. Additionally, the sealant can be disposed within the additional void spaces, for example a hole 122 that extends through the sealing member 36.

Preferably, the sealant comprises a water impermeable material or compound, for example, oil, grease, or gel. In one exemplary embodiment, the sealant comprises petroleum jelly and is used to provide a moisture barrier surrounding the sensor 32. In one experiment, petroleum jelly was liquefied by heating, after which a sensor 32 was immersed into the liquefied petroleum jelly to coat the outer surfaces thereof. The sensor was then assembled into a housing and inserted into a host, during which deployment the sensor was inserted through the electrical contacts 28 and the petroleum jelly conforming there between. Sensors incorporating petroleum jelly, such as described above, when compared to sensors without the petroleum jelly moisture barrier exhibited less or no signal drift over time when studied in a humid or submersed environment. While not wishing to be bound by theory, it is believed that incorporation of a moisture barrier surrounding the sensor, especially between the sensor and its associated electrical contacts, reduces or eliminates the effects of humidity on the sensor signal. The viscosity of grease or oil-based moisture barriers allows penetration into and through even small cracks or crevices within the sensor and mounting unit, displacing moisture and thereby increasing the sealing properties thereof. U.S. Pat. No. 4,259,540 and U.S. Pat. No. 5,285,513 disclose materials suitable for use as a water impermeable material (sealant).

Referring to the electrical fit between the sensor 32 and the electronics unit 16, contacts 28 (through which the sensor extends) are configured to electrically connect with mutually engaging contacts on the electronics unit 16. A variety of configurations are contemplated; however, the mutually engaging contacts operatively connect upon detachable connection of the electronics unit 16 with the mounting unit 14, and are substantially sealed from external moisture by sealing member 36. Even with the sealing member, some circumstances may exist wherein moisture can penetrate into the area surrounding the sensor 32 and or contacts, for example, exposure to a humid or wet environment (e.g., caused by sweat, showering, or other environmental causes). It has been observed that exposure of the sensor to moisture can be a cause of baseline signal drift of the sensor over time. For example in a glucose sensor, the baseline is the component of a glucose sensor signal that is not related to glucose (the amount of signal if no glucose is present), which is ideally constant over time. However, some circumstances my exist wherein the baseline can fluctuate over time, also referred to as drift, which can be caused, for example, by changes in a host's metabolism, cellular migration surrounding the sensor, interfering species, humidity in the environment, and the like.

In some embodiments, the mounting unit is designed to provide ventilation (e.g., a vent hole 124) between the exit-site and the sensor. In certain embodiments, a filter (not shown) is provided in the vent hole 124 that allows the passage of air, while preventing contaminants from entering the vent hole 124 from the external environment. While not wishing to be bound by theory, it is believed that ventilation to the exit-site (or to the sensor 32) can reduce or eliminate trapped moisture or bacteria, which can otherwise increase the growth and/or lifetime of bacteria adjacent to the sensor.

In some alternative embodiments, a sealing material is provided, which seals the needle and/or sensor from contamination of the external environment during and after sensor insertion. For example, one problem encountered in conventional transcutaneous devices is infection of the exit-site of the wound. For example, bacteria or contaminants can migrate from ex vivo, for example, any ex vivo portion of the device or the ex vivo environment, through the exit-site of the needle/sensor, and into the subcutaneous tissue, causing contamination and infection. Bacteria and/or contaminants can originate from handling of the device, exposed skin areas, and/or leakage from the mounting unit (external to) on the host. In many conventional transcutaneous devices, there exists some path of migration for bacteria and contaminants to the exit-site, which can become contaminated during sensor insertion or subsequent handling or use of the device. Furthermore, in some embodiments of a transcutaneous analyte sensor, the insertion-aiding device (for example, needle) is an integral part of the mounting unit; namely, the device stores the insertion device after insertion of the sensor, which is isolated from the exit-site (namely, point-of-entry of the sensor) after insertion.

Accordingly, these alternative embodiments provide a sealing material on the mounting unit, interposed between the housing and the skin, wherein the needle and/or sensor are adapted to extend through, and be sealed by, the sealing material. The sealing material is preferably formed from a flexible material that substantially seals around the needle/sensor. Appropriate flexible materials include malleable materials, elastomers, gels, greases, or the like (e.g., see U.S. Pat. No. 4,259,540 and U.S. Pat. No. 5,285,513). However, not all embodiments include a sealing material, and in some embodiments a clearance hole or other space surrounding the needle and/or sensor is preferred.

In one embodiment, the base 24 of the mounting unit 14 is formed from a flexible material, for example silicone, which by its elastomeric properties seals the needle and/or sensor at the exit port 126, such as is illustrated in FIGS. 11A and 11B. Thus, sealing material can be formed as a unitary or integral piece with the back surface 25 of the mounting unit 14, or with an adhesive pad 8 on the back surface of the mounting unit, however alternatively can be a separate part secured to the device. In some embodiments, the sealing material can extend through the exit port 126 above or below the plane of the adhesive pad surface, or the exit port 126 can comprise a septum seal such as those used in the medical storage and disposal industries (for example, silica gel sandwiched between upper and lower seal layers, such as layers comprising chemically inert materials such as PTFE). A variety of known septum seals can be implemented into the exit port of the preferred embodiments described herein. Whether the sealing material is integral with or a separate part attached to the mounting unit 14, the exit port 126 is advantageously sealed so as to reduce or eliminate the migration of bacteria or other contaminants to or from the exit-site of the wound and/or within the mounting unit.

During use, a host or caretaker positions the mounting unit at the appropriate location on or near the host's skin and prepares for sensor insertion. During insertion, the needle aids in sensor insertion, after which the needle is retracted into the mounting unit leaving the sensor in the subcutaneous tissue. In this embodiment, the exit-port 126 includes a layer of sealing material, such as a silicone membrane, that encloses the exit-port in a configuration that protects the exit-site from contamination that can migrate from the mounting unit or spacing external to the exit-site. Thus, when the sensor 32 and/or needle 72 extend through, for example, an aperture or a puncture in the sealing material, to provide communication between the mounting unit and subcutaneous space, a seal is formed there between. Elastomeric sealing materials can be advantageous in some embodiments because the elasticity provides a conforming seal between the needle/sensor and the mounting unit and/or because the elasticity provides shock-absorbing qualities allowing relative movement between the device and the various layers of the host's tissue, for example.

In some alternative embodiments, the sealing material includes a bioactive agent incorporated therein. Suitable bioactive agents include those which are known to discourage or prevent bacteria and infection, for example, anti-inflammatory, antimicrobials, antibiotics, or the like. It is believed that diffusion or presence of a bioactive agent can aid in prevention or elimination of bacteria adjacent to the exit-site.

In practice, after the sensor 32 has been inserted into the host's tissue, and an electrical connection formed by mating the electronics unit 16 to the mounting unit 14, the sensor measures an analyte concentration continuously or continually, for example, at an interval of from about fractions of a second to about 10 minutes or more.

Sensor Electronics

The following description of sensor electronics associated with the electronics unit is applicable to a variety of continuous analyte sensors, such as non-invasive, minimally invasive, and/or invasive (e.g., transcutaneous and wholly implantable) sensors. For example, the sensor electronics and data processing as well as the receiver electronics and data processing described below can be incorporated into the wholly implantable glucose sensor disclosed in co-pending U.S. patent application Ser. No. 10/838,912, filed May 3, 2004 and entitled "IMPLANTABLE ANALYTE SENSOR" and U.S. patent application Ser. No. 10/885,476 filed Jul. 6, 2004 and entitled, "SYSTEMS AND METHODS FOR MANUFACTURE OF AN ANALYTE-MEASURING DEVICE INCLUDING A MEMBRANE SYSTEM".

Figure 13:
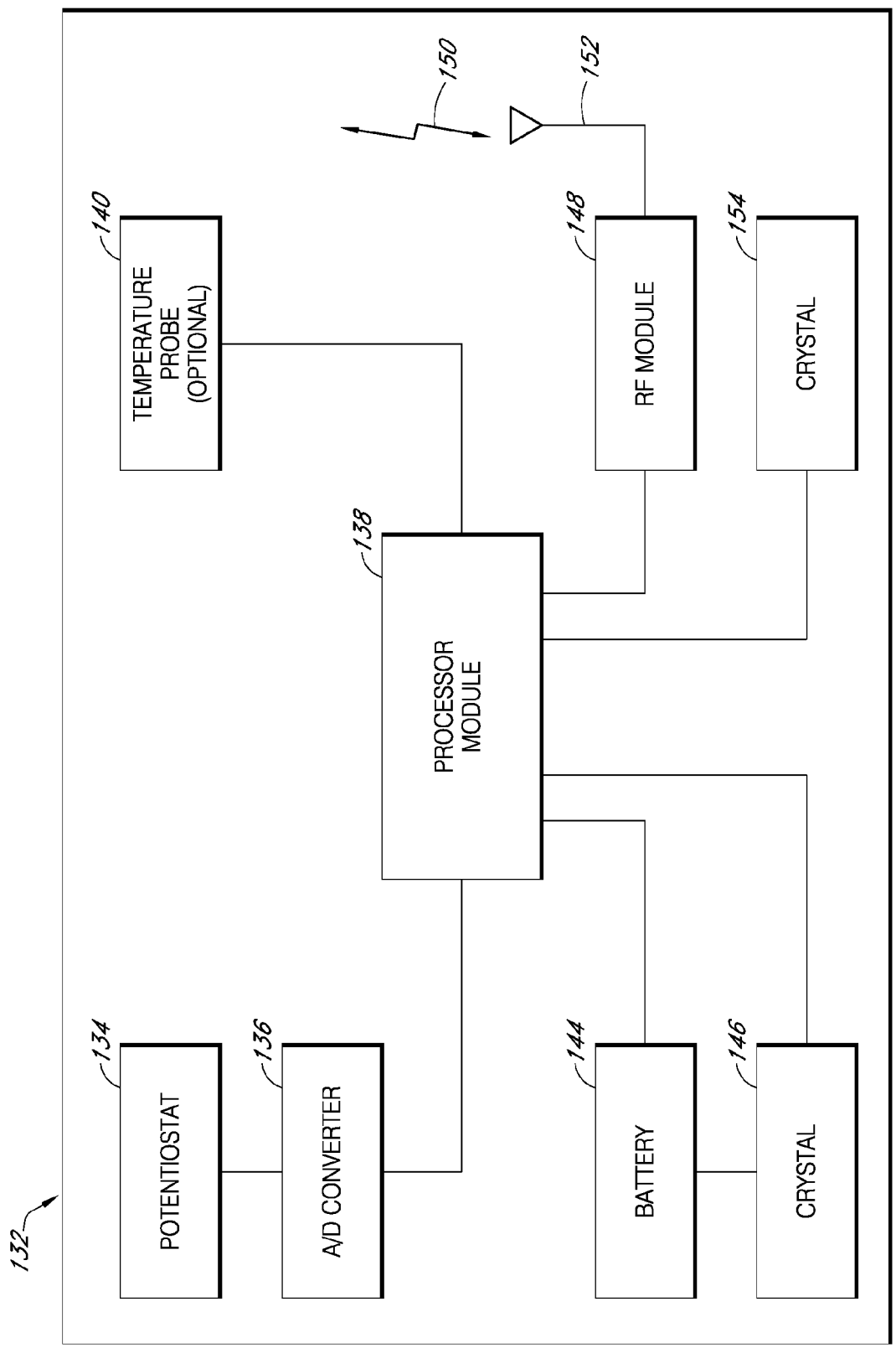
FIG. 13 is a block diagram that illustrates electronics associated with a sensor system.

FIG. 13 is a block diagram that illustrates the electronics 132 associated with the sensor system 10 in one embodiment. In this embodiment, a potentiostat 134 is shown, which is operably connected to an electrode system (such as described above) and provides a voltage to the electrodes, which biases the sensor to enable measurement of an current signal indicative of the analyte concentration in the host (also referred to as the analog portion). In some embodiments, the potentiostat includes a resistor (not shown) that translates the current into voltage. In some alternative embodiments, a current to frequency converter is provided that is configured to continuously integrate the measured current, for example, using a charge counting device.

An A/D converter 136 digitizes the analog signal into a digital signal, also referred to as "counts" for processing. Accordingly, the resulting raw data stream in counts, also referred to as raw sensor data, is directly related to the current measured by the potentiostat 84.

A processor module 138 includes the central control unit that controls the processing of the sensor electronics 132. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in co-pending U.S. patent application Ser. No. 10/648,849, filed Aug. 22, 2003, and entitled, "SYSTEMS AND METHODS FOR REPLACING SIGNAL ARTIFACTS IN A GLUCOSE SENSOR DATA STREAM"). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, or the like.

In some embodiments, the processor module comprises a digital filter, for example, an IIR or FIR filter, configured to smooth the raw data stream from the A/D converter. Generally, digital filters are programmed to filter data sampled at a predetermined time interval (also referred to as a sample rate.) In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a sensor ID code, raw data, filtered data, and/or error detection or correction. The processor module can be configured to transmit any combination of raw and/or filtered data.

In some embodiments, the processor module further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable between about 2 seconds and about 850 minutes, more preferably between about 30 second and 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.)

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter 136 is configured to continuously measure the current flowing at the working electrode and to convert the current measurement to digital values representative of the current. In one embodiment, the current flow is measured by a charge counting device (e.g., a capacitor). Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

A battery 144 is operably connected to the sensor electronics 132 and provides the power for the sensor. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal 96 is operably connected to the processor 138 and maintains system time for the computer system as a whole, for example for the programmable acquisition time within the processor module.

Optional temperature probe 140 is shown, wherein the temperature probe is located on the electronics assembly or the glucose sensor itself. The temperature probe can be used to measure ambient temperature in the vicinity of the glucose sensor. This temperature measurement can be used to add temperature compensation to the calculated glucose value.

An RF module 148 is operably connected to the processor 138 and transmits the sensor data from the sensor to a receiver within a wireless transmission 150 via antenna 152. In some embodiments, a second quartz crystal 154 provides the time base for the RF carrier frequency used for data transmissions from the RF transceiver. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. Additionally, in wholly implantable devices, the carrier frequency is adapted for physiological attenuation levels, which is accomplished by tuning the RF module in a simulated in vivo environment to ensure RF functionality after implantation; accordingly, the preferred glucose sensor can sustain sensor function for 3 months, 6 months, 12 months, or 24 months or more.

When a sensor is first implanted into host tissue, the sensor and receiver are initialized. This is referred to as start-up mode, and involves optionally resetting the sensor data and calibrating the sensor 32. In selected embodiments, mating the electronics unit 16 to the mounting unit triggers a start-up mode. In other embodiments, the start-up mode is triggered by the receiver, which is described in more detail with reference to FIG. 19, below.

Preferably, the electronics unit 16 indicates to the receiver (FIGS. 14 and 15) that calibration is to be initialized (or re-initialized). The electronics unit 16 transmits a series of bits within a transmitted data packet wherein a sensor code can be included in the periodic transmission of the device. The status code is used to communicate sensor status to the receiving device. The status code can be inserted into any location in the transmitted data packet, with or without other sensor information. In one embodiment, the status code is designed to be unique or near unique to an individual sensor, which can be accomplished using a value that increments, decrements, or changes in some way after the transmitter detects that a sensor has been removed and/or attached to the transmitter. In an alternative embodiment, the status code can be configured to follow a specific progression, such as a BCD interpretation of a Gray code.

In some embodiments, the sensor electronics 132 are configured to detect a current drop to zero in the working electrode 44 associated with removal of a sensor 32 from the host (or the electronics unit 16 from the mounting unit 14), which can be configured to trigger an increment of the status code. If the incremented value reaches a maximum, it can be designed to roll over to 0. In some embodiments, the sensor electronics are configured to detect a voltage change cycle associated with removal and/or re-insertion of the sensor, which can be sensed in the counter electrode (e.g., of a three-electrode sensor), which can be configured to trigger an increment of the status code.

In some embodiments, the sensor electronics 132 can be configured to send a special value (for example, 0) that indicates that the electronics unit is not attached when removal of the sensor (or electronics unit) is detected. This special value can be used to trigger a variety of events, for example, to halt display of analyte values. Incrementing or decrementing routines can be used to skip this special value.

In some embodiments, the electronics unit 16 is configured to include additional contacts, which are designed to sense a specific resistance, or passive value, in the sensor system while the electronics unit is attached to the mounting unit. Preferably, these additional contacts are configured to detect information about a sensor, for example, whether the sensor is operatively connected to the mounting unit, the sensor's ID, a calibration code, or the like. For example, subsequent to sensing the passive value, the sensor electronics can be configured to change the sensor ID code by either mapping the value to a specific code, or internally detecting that the code is different and adjusting the sensor ID code in a predictable manner. As another example, the passive value can include information on parameters specific to a sensor (such as in vitro sensitivity information as described elsewhere herein).

In some embodiments, the electronics unit 16 includes additional contacts configured to communicate with a chip disposed in the mounting unit 14. In this embodiment, the chip is designed with a unique or near-unique signature that can be detected by the electronics unit 16 and noted as different, and/or transmitted to the receiver 158 as the sensor ID code.

In some embodiments, the electronics unit 16 is inductively coupled to an RFID or similar chip in the mounting unit 14. In this embodiment, the RFID tag uniquely identifies the sensor 32 and allows the transmitter to adjust the sensor ID code accordingly and/or to transmit the unique identifier to the receiver 158.

In some situations, it can be desirable to wait an amount of time after insertion of the sensor to allow the sensor to equilibrate in vivo also referred to as "break-in". Accordingly, the sensor electronics can be configured to aid in decreasing the break-in time of the sensor by applying different voltage settings (for example, starting with a higher voltage setting and then reducing the voltage setting) to speed the equilibration process.

In some situations, the sensor may not properly deploy, connect to, or otherwise operate as intended. Accordingly, the sensor electronics can be configured such that if the current obtained from the working electrode, or the subsequent conversion of the current into digital counts, for example, is outside of an acceptable threshold, then the sensor is marked with an error flag, or the like. The error flag can be transmitted to the receiver to instruct the user to reinsert a new sensor, or to implement some other error correction.

The above-described detection and transmission methods can be advantageously employed to minimize or eliminate human interaction with the sensor, thereby minimizing human error and/or inconvenience. Additionally, the sensors of preferred embodiments do not require that the receiver be in proximity to the transmitter during sensor insertion. Any one or more of the above described methods of detecting and transmitting insertion of a sensor and/or electronics unit can be combined or modified, as is appreciated by one skilled in the art.

Receiver

Figure 14:
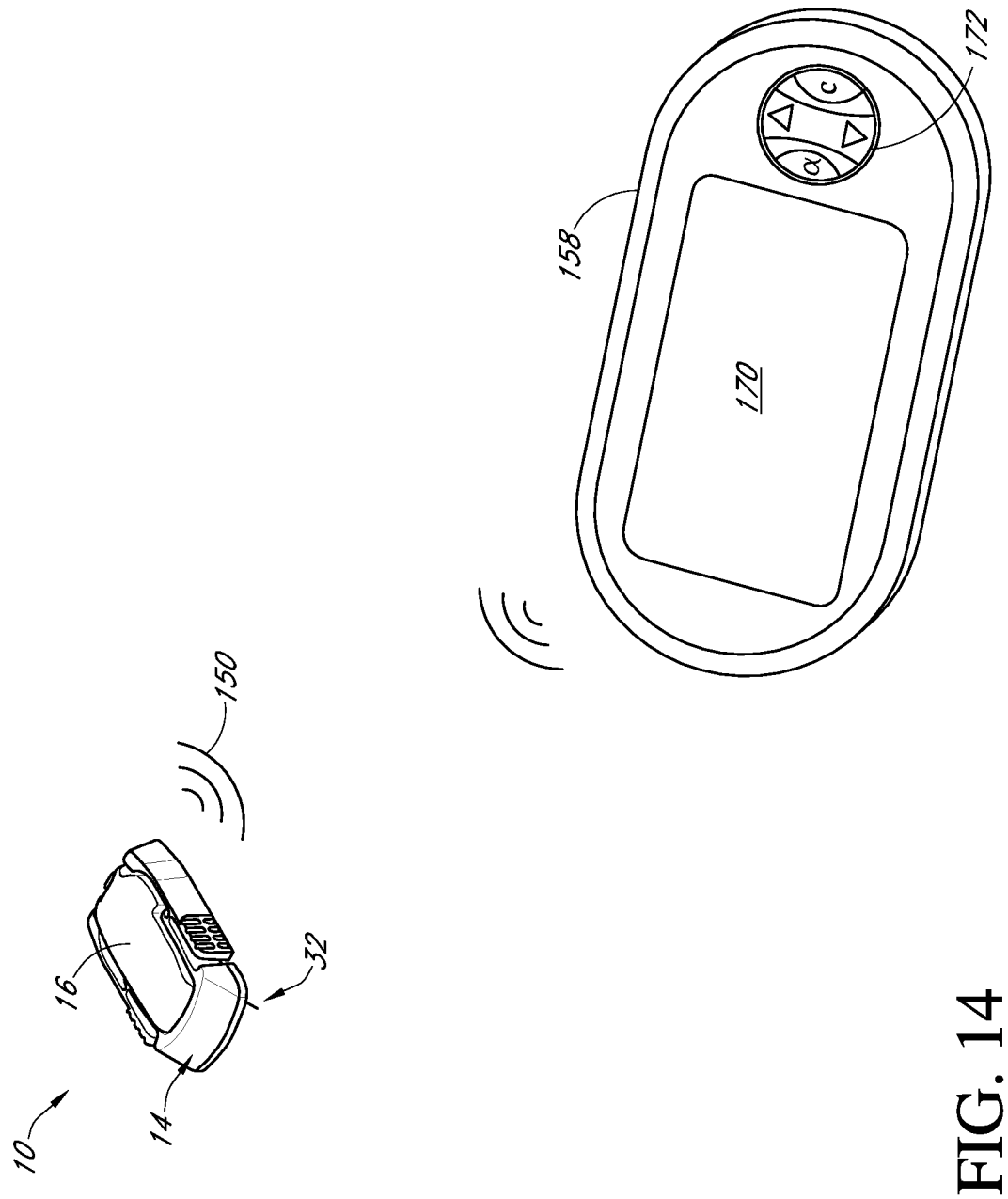
FIG. 14 is a perspective view of a sensor system wirelessly communicating with a receiver.

FIG. 14 is a perspective view of a sensor system, including wireless communication between a sensor and a receiver. Preferably the electronics unit 16 is wirelessly connected to a receiver 158 via one- or two-way RF transmissions or the like. However, a wired connection is also contemplated. The receiver 158 provides much of the processing and display of the sensor data, and can be selectively worn and/or removed at the host's convenience. Thus, the sensor system 10 can be discreetly worn, and the receiver 158, which provides much of the processing and display of the sensor data, can be selectively worn and/or removed at the host's convenience. Particularly, the receiver 158 includes programming for retrospectively and/or prospectively initiating a calibration, converting sensor data, updating the calibration, evaluating received reference and sensor data, and evaluating the calibration for the analyte sensor, such as described in more detail with reference to co-pending U.S. patent application Ser. No. 10/633,367, filed Aug. 1, 2003 and entitled, "SYSTEM AND METHODS FOR PROCESSING ANALYTE SENSOR DATA."

Receiver Electronics

Figure 15A:
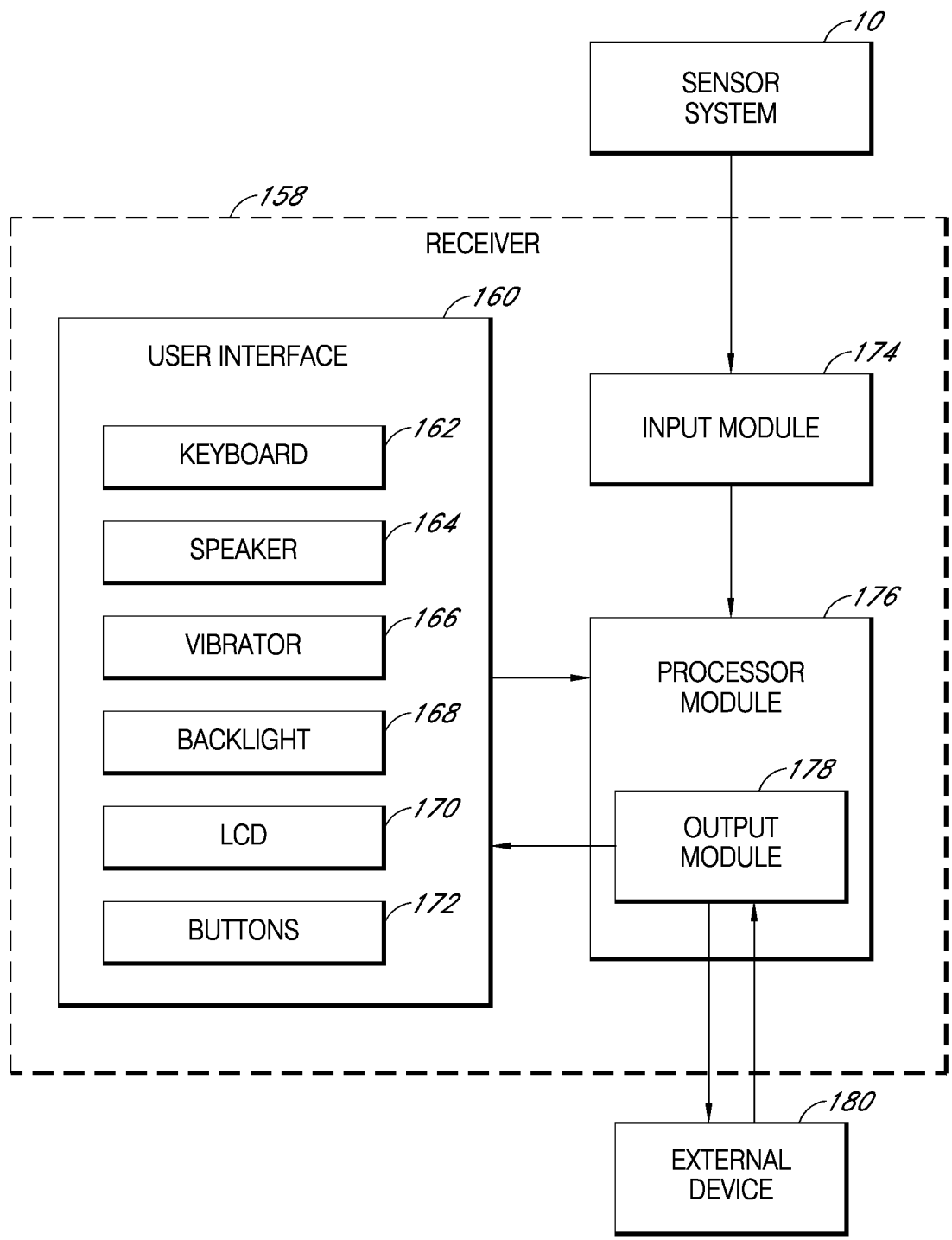
FIG. 15A is a block diagram that illustrates a configuration of a medical device including a continuous analyte sensor, a receiver, and an external device.

FIG. 15A is a block diagram that illustrates the configuration of the medical device in one embodiment, including a continuous analyte sensor, a receiver, and an external device.

In general, the analyte sensor system is any sensor configuration that provides an output signal indicative of a concentration of an analyte (e.g., invasive, minimally-invasive, and/or non-invasive sensors as described above). The output signal is sent to a receiver 158 and received by an input module 174, which is described in more detail below. The output signal is typically a raw data stream that is used to provide a useful value of the measured analyte concentration to a patient or a doctor, for example. In some embodiments, the raw data stream can be continuously or periodically algorithmically smoothed or otherwise modified to diminish outlying points that do not accurately represent the analyte concentration, for example due to signal noise or other signal artifacts, such as described in co-pending U.S. patent application Ser. No. 10/632,537 entitled, "SYSTEMS AND METHODS FOR REPLACING SIGNAL ARTIFACTS IN A GLUCOSE SENSOR DATA STREAM," filed Aug. 22, 2003, which is incorporated herein by reference in its entirety.

Referring again to FIG. 15A, the receiver 158, which is operatively linked to the sensor system 10, receives a data stream from the sensor system 10 via the input module 174. In one embodiment, the input module includes a quartz crystal operably connected to an RF transceiver (not shown) that together function to receive and synchronize data streams from the sensor system 10. However, the input module 174 can be configured in any manner that is capable of receiving data from the sensor. Once received, the input module 174 sends the data stream to a processor 176 that processes the data stream, such as is described in more detail below.

The processor 176 is the central control unit that performs the processing, such as storing data, analyzing data streams, calibrating analyte sensor data, estimating analyte values, comparing estimated analyte values with time corresponding measured analyte values, analyzing a variation of estimated analyte values, downloading data, and controlling the user interface by providing analyte values, prompts, messages, warnings, alarms, or the like. The processor includes hardware and software that performs the processing described herein, for example flash memory provides permanent or semi-permanent storage of data, storing data such as sensor ID, receiver ID, and programming to process data streams (for example, programming for performing estimation and other algorithms described elsewhere herein) and random access memory (RAM) stores the system's cache memory and is helpful in data processing.

Preferably, the input module 174 or processor module 176 performs a Cyclic Redundancy Check (CRC) to verify data integrity, with or without a method of recovering the data if there is an error. In some embodiments, error correction techniques such as those that use Hamming codes or Reed-Solomon encoding/decoding methods are employed to correct for errors in the data stream. In one alternative embodiment, an iterative decoding technique is employed, wherein the decoding is processed iteratively (e.g., in a closed loop) to determine the most likely decoded signal. This type of decoding can allow for recovery of a signal that is as low as 0.5 dB above the noise floor, which is in contrast to conventional non-iterative decoding techniques (such as Reed-Solomon), which requires approximately 3 dB or about twice the signal power to recover the same signal (e.g., a turbo code).

An output module 178, which is integral with and/or operatively connected with the processor 176, includes programming for generating output based on the data stream received from the sensor system 10 and its processing incurred in the processor 176. In some embodiments, output is generated via a user interface 160.

Figure 15B:
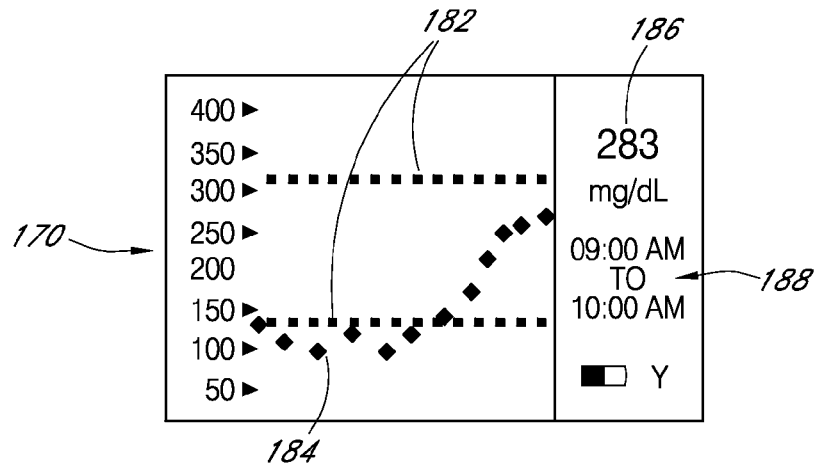
FIGS. 15B to 15D are illustrations of receiver liquid crystal displays showing embodiments of screen displays.
Figure 15C:
Figure 15D:
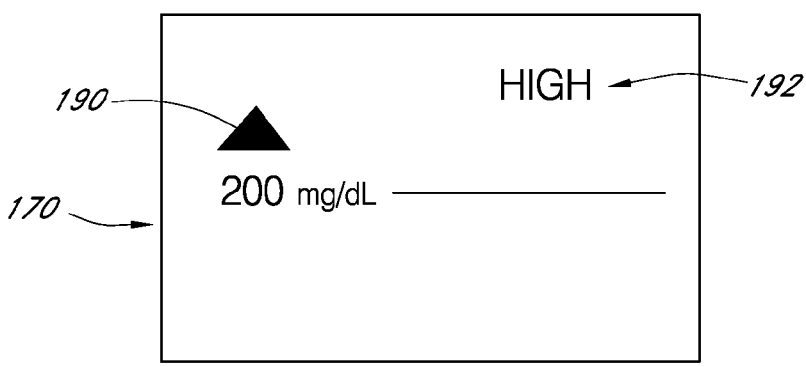

The user interface 160 comprises a keyboard 162, speaker 164, vibrator 166, backlight 168, liquid crystal display (LCD) screen 170, and one or more buttons 172. The components that comprise the user interface 160 include controls to allow interaction of the user with the receiver. The keyboard 162 can allow, for example, input of user information about himself/herself, such as mealtime, exercise, insulin administration, customized therapy recommendations, and reference analyte values. The speaker 164 can produce, for example, audible signals or alerts for conditions such as present and/or estimated hyperglycemic or hypoglycemic conditions in a person with diabetes. The vibrator 166 can provide, for example, tactile signals or alerts for reasons such as described with reference to the speaker, above. The backlight 168 can be provided, for example, to aid the user in reading the LCD 170 in low light conditions. The LCD 170 can be provided, for example, to provide the user with visual data output, such as is described in co-pending U.S. patent application Ser. No. 11/007,920 filed Dec. 8, 2004 and entitled "SIGNAL PROCESSING FOR CONTINUOUS ANALYTE SENSORS." FIGS. 15B to 15D illustrate some additional visual displays that can be provided on the screen 170. In some embodiments, the LCD is a touch-activated screen, enabling each selection by a user, for example, from a menu on the screen. The buttons 172 can provide for toggle, menu selection, option selection, mode selection, and reset, for example. In some alternative embodiments, a microphone can be provided to allow for voice-activated control.

In some embodiments, prompts or messages can be displayed on the user interface to convey information to the user, such as reference outlier values, requests for reference analyte values, therapy recommendations, deviation of the measured analyte values from the estimated analyte values, or the like. Additionally, prompts can be displayed to guide the user through calibration or trouble-shooting of the calibration.

Additionally, data output from the output module 178 can provide wired or wireless, one- or two-way communication between the receiver 158 and an external device 180. The external device 180 can be any device that wherein interfaces or communicates with the receiver 158. In some embodiments, the external device 180 is a computer, and the receiver 158 is able to download historical data for retrospective analysis by the patient or physician, for example. In some embodiments, the external device 180 is a modem or other telecommunications station, and the receiver 158 is able to send alerts, warnings, emergency messages, or the like, via telecommunication lines to another party, such as a doctor or family member. In some embodiments, the external device 180 is an insulin pen, and the receiver 158 is able to communicate therapy recommendations, such as insulin amount and time to the insulin pen. In some embodiments, the external device 180 is an insulin pump, and the receiver 158 is able to communicate therapy recommendations, such as insulin amount and time to the insulin pump. The external device 180 can include other technology or medical devices, for example pacemakers, implanted analyte sensor patches, other infusion devices, telemetry devices, or the like.

The user interface 160, including keyboard 162, buttons 172, a microphone (not shown), and the external device 180, can be configured to allow input of data. Data input can be helpful in obtaining information about the patient (for example, meal time, exercise, or the like), receiving instructions from a physician (for example, customized therapy recommendations, targets, or the like), and downloading software updates, for example. Keyboard, buttons, touch-screen, and microphone are all examples of mechanisms by which a user can input data directly into the receiver. A server, personal computer, personal digital assistant, insulin pump, and insulin pen are examples of external devices that can provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual. While a few examples of data input have been provided here, a variety of information can be input, which can be helpful in data processing.

FIG. 15B is an illustration of an LCD screen 170 showing continuous and single point glucose information in the form of a trend graph 184 and a single numerical value 186. The trend graph shows upper and lower boundaries 182 representing a target range between which the host should maintain his/her glucose values. Preferably, the receiver is configured such that these boundaries 182 can be configured or customized by a user, such as the host or a care provider. By providing visual boundaries 182, in combination with continuous analyte values over time (e.g., a trend graph 184), a user may better learn how to control his/her analyte concentration (e.g., a person with diabetes may better learn how to control his/her glucose concentration) as compared to single point (single numerical value 186) alone. Although FIG. 15B illustrates a 1-hour trend graph (e.g., depicted with a time range 188 of 1-hour), a variety of time ranges can be represented on the screen 170, for example, 3-hour, 9-hour, 1-day, and the like.

FIG. 15C is an illustration of an LCD screen 170 showing a low alert screen that can be displayed responsive to a host's analyte concentration falling below a lower boundary (see boundaries 182). In this exemplary screen, a host's glucose concentration has fallen to 55 mg/dL, which is below the lower boundary set in FIG. 15B, for example. The arrow 190 represents the direction of the analyte trend, for example, indicating that the glucose concentration is continuing to drop. The annotation 192 ("LOW") is helpful in immediately and clearly alerting the host that his/her glucose concentration has dropped below a preset limit, and what may be considered to be a clinically safe value, for example. FIG. 15D is an illustration of an LCD screen 170 showing a high alert screen that can be displayed responsive to a host's analyte concentration rising above an upper boundary (see boundaries 182). In this exemplary screen, a host's glucose concentration has risen to 200 mg/dL, which is above a boundary set by the host, thereby triggering the high alert screen. The arrow 190 represents the direction of the analyte trend, for example, indicating that the glucose concentration is continuing to rise. The annotation 192 ("HIGH") is helpful in immediately and clearly alerting the host that his/her glucose concentration has above a preset limit, and what may be considered to be a clinically safe value, for example.

Although a few exemplary screens are depicted herein, a variety of screens can be provided for illustrating any of the information described in the preferred embodiments, as well as additional information. A user can toggle between these screens (e.g., using buttons 172) and/or the screens can be automatically displayed responsive to programming within the receiver 158, and can be simultaneously accompanied by another type of alert (audible or tactile, for example).

Algorithms

Figure 16A:
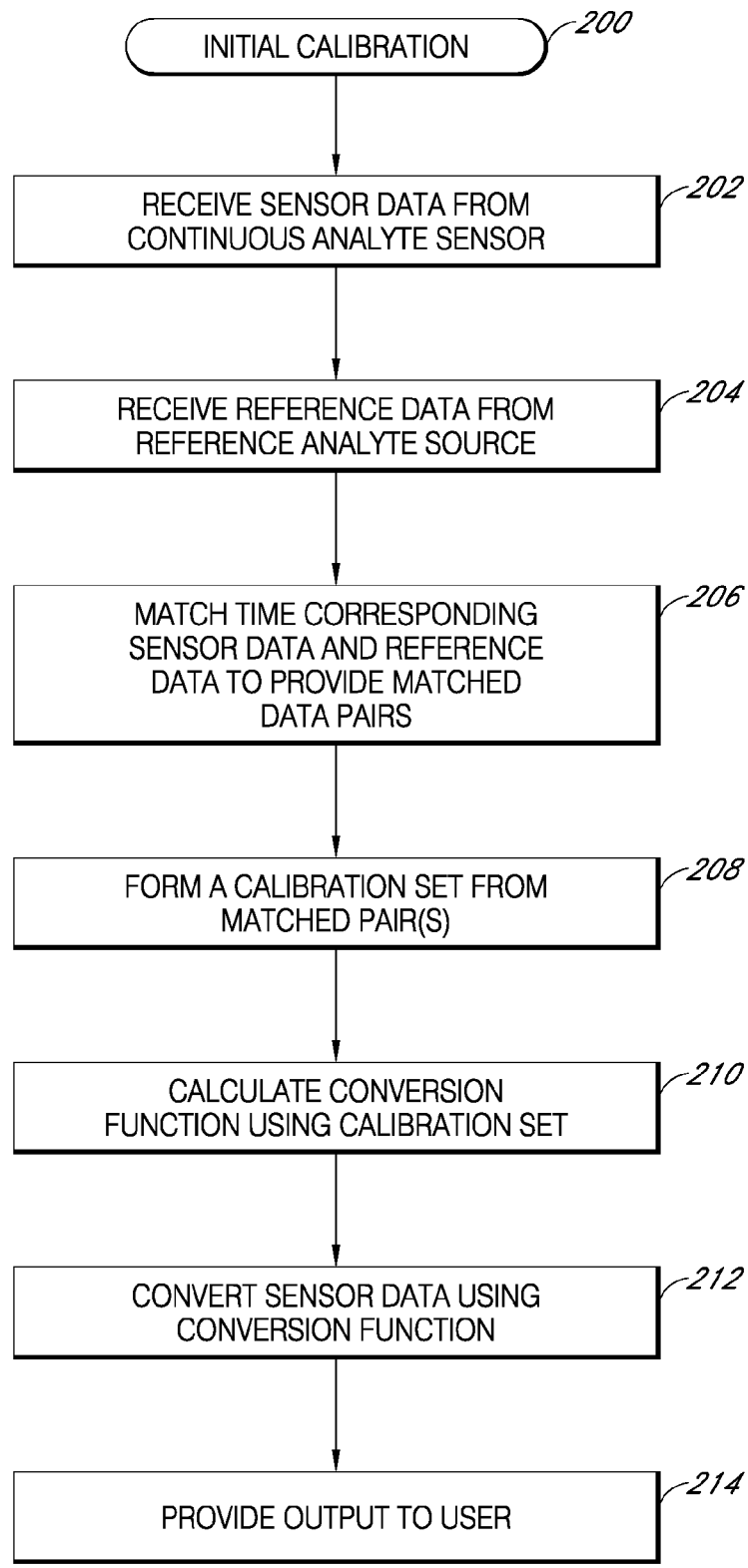
FIG. 16A is a flow chart that illustrates the initial calibration and data output of sensor data.

FIG. 16A provides a flow chart 200 that illustrates the initial calibration and data output of the sensor data in one embodiment, wherein calibration is responsive to reference analyte data. Initial calibration, also referred to as start-up mode, occurs at the initialization of a sensor, for example, the first time an electronics unit is used with a particular sensor. In certain embodiments, start-up calibration is triggered when the system determines that it can no longer remain in normal or suspended mode, which is described in more detail with reference to FIG. 19.

Calibration of an analyte sensor comprises data processing that converts sensor data signal into an estimated analyte measurement that is meaningful to a user. Accordingly, a reference analyte value is used to calibrate the data signal from the analyte sensor.

At block 202, a sensor data receiving module, also referred to as the sensor data module, receives sensor data (e.g., a data stream), including one or more time-spaced sensor data points, from the sensor 32 via the receiver 158, which can be in wired or wireless communication with the sensor 32. The sensor data point(s) can be smoothed (filtered) in certain embodiments using a filter, for example, a finite impulse response (FIR) or infinite impulse response (IIR) filter. During the initialization of the sensor, prior to initial calibration, the receiver receives and stores the sensor data, however it can be configured to not display any data to the user until initial calibration and, optionally, stabilization of the sensor has been established. In some embodiments, the data stream can be evaluated to determine sensor break-in (equilibration of the sensor in vitro or in vivo).

At block 204, a reference data receiving module, also referred to as the reference input module, receives reference data from a reference analyte monitor, including one or more reference data points. In one embodiment, the reference analyte points can comprise results from a self-monitored blood analyte test (e.g., finger stick test). For example, the user can administer a self-monitored blood analyte test to obtain an analyte value (e.g., point) using any known analyte sensor, and then enter the numeric analyte value into the computer system. Alternatively, a self-monitored blood analyte test is transferred into the computer system through a wired or wireless connection to the receiver (e.g. computer system) so that the user simply initiates a connection between the two devices, and the reference analyte data is passed or downloaded between the self-monitored blood analyte test and the receiver. In yet another embodiment, the self-monitored analyte test (e.g., SMBG) is integral with the receiver so that the user simply provides a blood sample to the receiver, and the receiver runs the analyte test to determine a reference analyte value. Co-pending U.S. patent application Ser. No. 10/991, 966, filed on Nov. 17, 2004 and entitled "INTEGRATED RECEIVER FOR CONTINUOUS ANALYTE SENSOR" describes some systems and methods for integrating a reference analyte monitor into a receiver for a continuous analyte sensor.

In some alternative embodiments, the reference data is based on sensor data from another substantially continuous analyte sensor, e.g., a transcutaneous analyte sensor described herein, or another type of suitable continuous analyte sensor. In an embodiment employing a series of two or more transcutaneous (or other continuous) sensors, the sensors can be employed so that they provide sensor data in discrete or overlapping periods. In such embodiments, the sensor data from one continuous sensor can be used to calibrate another continuous sensor, or be used to confirm the validity of a subsequently employed continuous sensor.

In some embodiments, reference data can be subjected to "outlier detection" wherein the accuracy of a received reference analyte data is evaluated as compared to time-corresponding sensor data. In one embodiment, the reference data is compared to the sensor data on a modified Clarke Error Grid (e.g., a test similar to the Clarke Error Grid except the boundaries between the different regions are modified slightly) to determine if the data falls within a predetermined threshold. If the data is not within the predetermined threshold, then the receiver can be configured to request additional reference analyte data. If the additional reference analyte data confirms (e.g., closely correlates to) the first reference analyte data, then the first and second reference values are assumed to be accurate and calibration of the sensor is adjusted or re-initialized. Alternatively, if the second reference analyte value falls within the predetermined threshold, then the first reference analyte value is assumed to be an outlier and the second reference analyte value is used by the algorithm(s) instead. In one alternative embodiments of outlier detection, projection is used to estimate an expected analyte value, which is compared with the actual value and a delta evaluated for substantial correspondence. However, other methods of outlier detection are possible.

Certain acceptability parameters can be set for reference values received from the user. For example, in one embodiment, the receiver can be configured to only accept reference analyte values of from about 40 mg/dL to about 400 mg/dL.

At block 206, a data matching module, also referred to as the processor module, matches reference data (e.g., one or more reference analyte data points) with substantially time corresponding sensor data (e.g., one or more sensor data points) to provide one or more matched data pairs. One reference data point can be matched to one time corresponding sensor data point to form a matched data pair. Alternatively, a plurality of reference data points can be averaged (e.g., equally or non-equally weighted average, mean-value, median, or the like) and matched to one time corresponding sensor data point to form a matched data pair, one reference data point can be matched to a plurality of time corresponding sensor data points averaged to form a matched data pair, or a plurality of reference data points can be averaged and matched to a plurality of time corresponding sensor data points averaged to form a matched data pair.

In one embodiment, time corresponding sensor data comprises one or more sensor data points that occur from about 0 minutes to about 20 minutes after the reference analyte data time stamp (e.g., the time that the reference analyte data is obtained). In one embodiment, a 5-minute time delay is chosen to compensate for a system time-lag (e.g., the time necessary for the analyte to diffusion through a membrane(s) of an analyte sensor). In alternative embodiments, the time corresponding sensor value can be greater than or less than that of the above-described embodiment, for example ±60 minutes. Variability in time correspondence of sensor and reference data can be attributed to, for example, a longer or shorter time delay introduced by the data smoothing filter, or if the configuration of the analyte sensor incurs a greater or lesser physiological time lag.

In some implementations of the sensor, the reference analyte data is obtained at a time that is different from the time that the data is input into the receiver. Accordingly, the "time stamp" of the reference analyte (e.g., the time at which the reference analyte value was obtained) is not the same as the time at which the receiver obtained the reference analyte data. Therefore, some embodiments include a time stamp requirement that ensures that the receiver stores the accurate time stamp for each reference analyte value, that is, the time at which the reference value was actually obtained from the user.

In certain embodiments, tests are used to evaluate the best-matched pair using a reference data point against individual sensor values over a predetermined time period (e.g., about 30 minutes). In one such embodiment, the reference data point is matched with sensor data points at 5-minute intervals and each matched pair is evaluated. The matched pair with the best correlation can be selected as the matched pair for data processing. In some alternative embodiments, matching a reference data point with an average of a plurality of sensor data points over a predetermined time period can be used to form a matched pair.

At block 208, a calibration set module, also referred to as the processor module, forms an initial calibration set from a set of one or more matched data pairs, which are used to determine the relationship between the reference analyte data and the sensor analyte data. The matched data pairs, which make up the initial calibration set, can be selected according to predetermined criteria. The criteria for the initial calibration set can be the same as, or different from, the criteria for the updated calibration sets. In certain embodiments, the number (n) of data pair(s) selected for the initial calibration set is one. In other embodiments, n data pairs are selected for the initial calibration set wherein n is a function of the frequency of the received reference data points. In various embodiments, two data pairs make up the initial calibration set or six data pairs make up the initial calibration set. In an embodiment wherein a substantially continuous analyte sensor provides reference data, numerous data points are used to provide reference data from more than 6 data pairs (e.g., dozens or even hundreds of data pairs). In one exemplary embodiment, a substantially continuous analyte sensor provides 288 reference data points per day (every five minutes for twenty-four hours), thereby providing an opportunity for a matched data pair 288 times per day, for example. While specific numbers of matched data pairs are referred to in the preferred embodiments, any suitable number of matched data pairs per a given time period can be employed.

In certain embodiments, the data pairs are selected only within a certain analyte value threshold, for example wherein the reference analyte value is from about 40 mg/dL to about 400 mg/dL. In certain embodiments, the data pairs that form the initial calibration set are selected according to their time stamp, for example, by waiting a predetermined "break-in" time period after implantation, the stability of the sensor data can be increased. In certain embodiments, the data pairs that form the initial calibration set are spread out over a predetermined time period, for example, a period of two hours or more. In certain embodiments, the data pairs that form the initial calibration set are spread out over a predetermined glucose range, for example, spread out over a range of at least 90 mg/dL or more.

At block 210, a conversion function module, also referred to as the processor module, uses the calibration set to create a conversion function. The conversion function substantially defines the relationship between the reference analyte data and the analyte sensor data.

A variety of known methods can be used with the preferred embodiments to create the conversion function from the calibration set. In one embodiment, wherein a plurality of matched data points form the calibration set, a linear least squares regression is used to calculate the conversion function; for example, this regression calculates a slope and an offset using the equation $y=mx+b$. A variety of regression or other conversion schemes can be implemented herein.

In some alternative embodiments, the sensor is calibrated with a single-point through the use of a dual-electrode system to simplify sensor calibration. In one such dual-electrode system, a first electrode functions as a hydrogen peroxide sensor including a membrane system containing glucose-oxidase disposed thereon, which operates as described herein. A second electrode is a hydrogen peroxide sensor that is configured similar to the first electrode, but with a modified membrane system (with the enzyme domain removed, for example). This second electrode provides a signal composed mostly of the baseline signal, b.

In some dual-electrode systems, the baseline signal is (electronically or digitally) subtracted from the glucose signal to obtain a glucose signal substantially without baseline. Accordingly, calibration of the resultant difference signal can be performed by solving the equation y=mx with a single paired measurement. Calibration of the implanted sensor in this alternative embodiment can be made less dependent on the values/range of the paired measurements, less sensitive to error in manual blood glucose measurements, and can facilitate the sensor's use as a primary source of glucose information for the user. Co-pending U.S. patent application Ser. No. 11/004,561 filed Dec. 3, 2004 and entitled, "CALIBRATION TECHNIQUES FOR A CONTINUOUS ANALYTE SENSOR" describes systems and methods for subtracting the baseline from a sensor signal.

In some alternative dual-electrode system embodiments, the analyte sensor is configured to transmit signals obtained from each electrode separately (e.g., without subtraction of the baseline signal). In this way, the receiver can process these signals to determine additional information about the sensor and/or analyte concentration. For example, by comparing the signals from the first and second electrodes, changes in baseline and/or sensitivity can be detected and/or measured and used to update calibration (e.g. without the use of a reference analyte value). In one such example, by monitoring the corresponding first and second signals over time, an amount of signal contributed by baseline can be measured. In another such example, by comparing fluctuations in the correlating signals over time, changes in sensitivity can be detected and/or measured.

In some alternative embodiments, a regression equation y=mx+b is used to calculate the conversion function; however, prior information can be provided for m and/or b, thereby enabling calibration to occur with fewer paired measurements. In one calibration technique, prior information (e.g., obtained from in vivo or in vitro tests) determines a sensitivity of the sensor and/or the baseline signal of the sensor by analyzing sensor data from measurements taken by the sensor (e.g., prior to inserting the sensor). For example, if there exists a predictive relationship between in vitro sensor parameters and in vivo parameters, then this information can be used by the calibration procedure. For example, if a predictive relationship exists between in vitro sensitivity and in vivo sensitivity, $m \approx f(m_{in\ vitro})$ then the predicted m can be used, along with a single matched pair, to solve for b (b=y−mx). If, in addition, b can be assumed=0, for example with a dual-electrode configuration that enables subtraction of the baseline from the signal such as described above, then both m and b are known a priori, matched pairs are not needed for calibration, and the sensor can be completely calibrated e.g. without the need for reference analyte values (e.g. values obtained after implantation in vivo.)

In another alternative embodiment, prior information can be provided to guide or validate the baseline (b) and/or sensitivity (m) determined from the regression analysis. In this embodiment, boundaries can be set for the regression line that defines the conversion function such that working sensors are calibrated accurately and easily (with two points), and non-working sensors are prevented from being calibrated. If the boundaries are drawn too tightly, a working sensor may not enter into calibration. Likewise, if the boundaries are drawn too loosely, the scheme can result in inaccurate calibration or can permit non-working sensors to enter into calibration. For example, subsequent to performing regression, the resulting slope and/or baseline are tested to determine whether they fall within a predetermined acceptable threshold (boundaries). These predetermined acceptable boundaries can be obtained from in vivo or in vitro tests (e.g., by a retrospective analysis of sensor sensitivities and/or baselines collected from a set of sensors/patients, assuming that the set is representative of future data).

If the slope and/or baseline fall within the predetermined acceptable boundaries, then the regression is considered acceptable and processing continues to the next step (e.g., block 212). Alternatively, if the slope and/or baseline fall outside the predetermined acceptable boundaries, steps can be taken to either correct the regression or fail-safe such that a system will not process or display errant data. This can be useful in situations wherein regression results in errant slope or baseline values. For example, when points (matched pairs) used for regression are too close in value, the resulting regression statistically is less accurate than when the values are spread farther apart. As another example, a sensor that is not properly deployed or is damaged during deployment can yield a skewed or errant baseline signal.

Figure 16B:
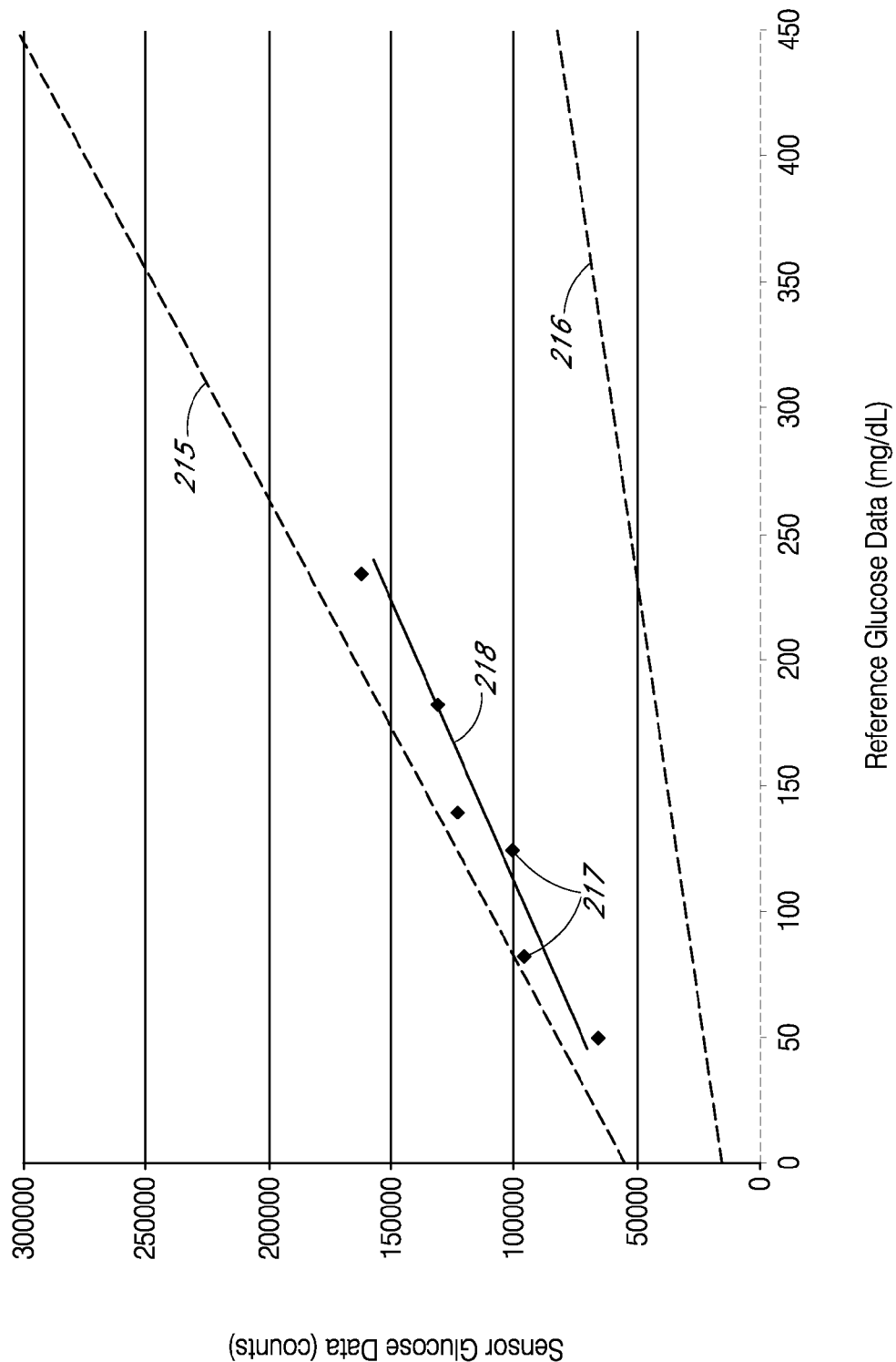
FIG. 16B is a graph that illustrates one example of using prior information for slope and baseline.

FIG. 16B is a graph that illustrates one example of using prior information for slope and baseline. The x-axis represents reference glucose data (blood glucose) from a reference glucose source in mg/dL; the y-axis represents sensor data from a transcutaneous glucose sensor of the preferred embodiments in counts. An upper boundary line 215 is a regression line that represents an upper boundary of "acceptability" in this example; the lower boundary line 216 is a regression line that represents a lower boundary of "acceptability" in this example. The boundary lines 215, 216 were obtained from retrospective analysis of in vivo sensitivities and baselines of glucose sensors as described in the preferred embodiments.

A plurality of matched data pairs 217 represents data pairs in a calibration set obtained from a glucose sensor as described in the preferred embodiments. The matched data pairs are plotted according to their sensor data and time-corresponding reference glucose data. A regression line 218 represents the result of regressing the matched data pairs 217 using least squares regression. In this example, the regression line falls within the upper and lower boundaries 215, 216 indicating that the sensor calibration is acceptable.

However, if the slope and/or baseline had fallen outside the predetermined acceptable boundaries, which would be illustrated in this graph by a line that crosses the upper and/or lower boundaries 215, 216, then the system is configured to assume a baseline value and re-run the regression (or a modified version of the regression) with the assumed baseline, wherein the assumed baseline value is derived from in vivo or in vitro testing. Subsequently, the newly derived slope and baseline are again tested to determine whether they fall within the predetermined acceptable boundaries. Similarly, the processing continues in response to the results of the boundary test. In general, for a set of matched pairs (e.g., calibration set), regression lines with higher slope (sensitivity) have a lower baseline and regression lines with lower slope (sensitivity) have a higher baseline. Accordingly, the step of assuming a baseline and testing against boundaries can be repeated using a variety of different assumed baselines based on the baseline, sensitivity, in vitro testing, and/or in vivo testing. For example, if a boundary test fails due to high sensitivity, then a higher baseline is assumed and the regression re-run and boundary-tested. It is preferred that after about two iterations of assuming a baseline and/or sensitivity and running a modified regression, the system assumes an error has occurred (if the resulting regression lines fall outside the boundaries) and fail-safe. The term "fail-safe" includes modifying the system processing and/or display of data responsive to a detected error avoid reporting of inaccurate or clinically irrelevant analyte values.

In these various embodiments utilizing an additional electrode, prior information (e.g., in vitro or in vivo testing), signal processing, or other information for assisting in the calibration process can be used alone or in combination to reduce or eliminate the dependency of the calibration on reference analyte values obtained by the host.

At block 212, a sensor data transformation module uses the conversion function to transform sensor data into substantially real-time analyte value estimates, also referred to as calibrated data, or converted sensor data, as sensor data is continuously (or intermittently) received from the sensor. For example, the sensor data, which can be provided to the receiver in "counts", is translated in to estimate analyte value(s) in mg/dL. In other words, the offset value at any given point in time can be subtracted from the raw value (e.g. in counts) and divided by the slope to obtain the estimate analyte value:

$$mg/dL = \frac{(rawvalue - \text{offset})}{\text{slope}}$$

In some alternative embodiments, the sensor and/or reference analyte values are stored in a database for retrospective analysis.

At block 214, an output module provides output to the user via the user interface. The output is representative of the estimated analyte value, which is determined by converting the sensor data into a meaningful analyte value. User output can be in the form of a numeric estimated analyte value, an indication of directional trend of analyte concentration, and/or a graphical representation of the estimated analyte data over a period of time, for example. Other representations of the estimated analyte values are also possible, for example audio and tactile.

In some embodiments, annotations are provided on the graph; for example, bitmap images are displayed thereon, which represent events experienced by the host. For example, information about meals, insulin, exercise, sensor insertion, sleep, and the like, can be obtained by the receiver (by user input or receipt of a transmission from another device) and displayed on the graphical representation of the host's glucose over time. It is believed that illustrating a host's life events matched with a host's glucose concentration over time can be helpful in educating the host to his or her metabolic response to the various events.

In yet another alternative embodiment, the sensor utilizes one or more additional electrodes to measure an additional analyte. Such measurements can provide a baseline or sensitivity measurement for use in calibrating the sensor. Furthermore, baseline and/or sensitivity measurements can be used to trigger events such as digital filtering of data or suspending display of data, all of which are described in more detail in co-pending U.S. patent application Ser. No. 11/004,561, filed Dec. 3, 2004 and entitled, "CALIBRATION TECHNIQUES FOR A CONTINUOUS ANALYTE SENSOR."

Figure 17:
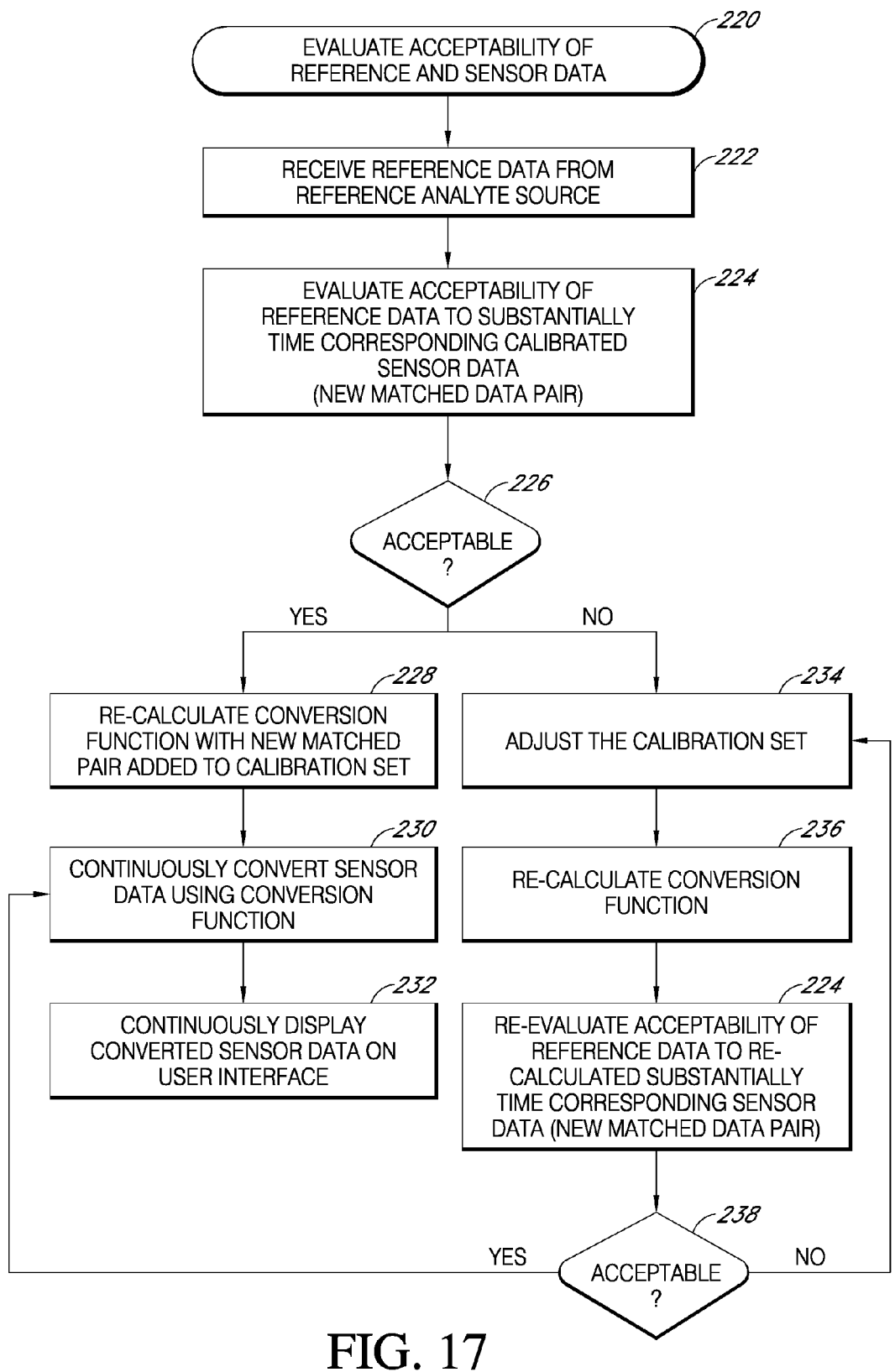
FIG. 17 is a flow chart that illustrates evaluation of reference and/or sensor data for statistical, clinical, and/or physiological acceptability.

FIG. 17 provides a flow chart 220 that illustrates the evaluation of reference and/or sensor data for statistical, clinical, and/or physiological acceptability in one embodiment. Although some acceptability tests are disclosed herein, any known statistical, clinical, physiological standards and methodologies can be applied to evaluate the acceptability of reference and sensor analyte data.

One cause for discrepancies in reference and sensor data is a sensitivity drift that can occur over time, when a sensor is inserted into a host and cellular invasion of the sensor begins to block transport of the analyte to the sensor, for example. Therefore, it can be advantageous to validate the acceptability of converted sensor data against reference analyte data, to determine if a drift of sensitivity has occurred and whether the calibration should be updated.

In one embodiment, the reference analyte data is evaluated with respect to substantially time corresponding converted sensor data to determine the acceptability of the matched pair. For example, clinical acceptability considers a deviation between time corresponding analyte measurements (for example, data from a glucose sensor and data from a reference glucose monitor) and the risk (for example, to the decision making of a person with diabetes) associated with that deviation based on the glucose value indicated by the sensor and/or reference data. Evaluating the clinical acceptability of reference and sensor analyte data, and controlling the user interface dependent thereon, can minimize clinical risk. Preferably, the receiver evaluates clinical acceptability each time reference data is obtained.

After initial calibration, such as is described in more detail with reference to FIG. 16, the sensor data receiving module 222 receives substantially continuous sensor data (e.g., a data stream) via a receiver and converts that data into estimated analyte values. As used herein, the term "substantially continuous" is a broad term and is used in its ordinary sense, without limitation, to refer to a data stream of individual measurements taken at time intervals (e.g., time-spaced) ranging from fractions of a second up to, e.g., 1, 2, or 5 minutes or more. As sensor data is continuously converted, it can be occasionally recalibrated in response to changes in sensor sensitivity (drift), for example. Initial calibration and re-calibration of the sensor require a reference analyte value. Accordingly, the receiver can receive reference analyte data at any time for appropriate processing.

At block 222, the reference data receiving module, also referred to as the reference input module, receives reference analyte data from a reference analyte monitor. In one embodiment, the reference data comprises one analyte value obtained from a reference monitor. In some alternative embodiments however, the reference data includes a set of analyte values entered by a user into the interface and averaged by known methods, such as are described elsewhere herein. In some alternative embodiments, the reference data comprises a plurality of analyte values obtained from another continuous analyte sensor.

The reference data can be pre-screened according to environmental and physiological issues, such as time of day, oxygen concentration, postural effects, and patient-entered environmental data. In one exemplary embodiment, wherein the sensor comprises an implantable glucose sensor, an oxygen sensor within the glucose sensor is used to determine if sufficient oxygen is being provided to successfully complete the necessary enzyme and electrochemical reactions for accurate glucose sensing. In another exemplary embodiment, the patient is prompted to enter data into the user interface, such as meal times and/or amount of exercise, which can be used to determine likelihood of acceptable reference data. In yet another exemplary embodiment, the reference data is matched with time-corresponding sensor data, which is then evaluated on a modified clinical error grid to determine its clinical acceptability.

Some evaluation data, such as described in the paragraph above, can be used to evaluate an optimum time for reference analyte measurement. Correspondingly, the user interface can then prompt the user to provide a reference data point for calibration within a given time period. Consequently, because the receiver proactively prompts the user during optimum calibration times, the likelihood of error due to environmental and physiological limitations can decrease and consistency and acceptability of the calibration can increase.

At block 224, the evaluation module, also referred to as acceptability module, evaluates newly received reference data. In one embodiment, the evaluation module evaluates the clinical acceptability of newly received reference data and time corresponding converted sensor data (new matched data pair). In one embodiment, a clinical acceptability evaluation module 224 matches the reference data with a substantially time corresponding converted sensor value, and determines the Clarke Error Grid coordinates. In this embodiment, matched pairs that fall within the A and B regions of the Clarke Error Grid are considered clinically acceptable, while matched pairs that fall within the C, D, and E regions of the Clarke Error Grid are not considered clinically acceptable.

A variety of other known methods of evaluating clinical acceptability can be utilized. In one alternative embodiment, the Consensus Grid is used to evaluate the clinical acceptability of reference and sensor data. In another alternative embodiment, a mean absolute difference calculation can be used to evaluate the clinical acceptability of the reference data. In another alternative embodiment, the clinical acceptability can be evaluated using any relevant clinical acceptability test, such as a known grid (e.g., Clarke Error or Consensus), and additional parameters, such as time of day and/or the increase or decreasing trend of the analyte concentration. In another alternative embodiment, a rate of change calculation can be used to evaluate clinical acceptability. In yet another alternative embodiment, wherein the received reference data is in substantially real time, the conversion function could be used to predict an estimated glucose value at a time corresponding to the time stamp of the reference analyte value (this can be required due to a time lag of the sensor data such as described elsewhere herein). Accordingly, a threshold can be set for the predicted estimated glucose value and the reference analyte value disparity, if any. In some alternative embodiments, the reference data is evaluated for physiological and/or statistical acceptability as described in more detail elsewhere herein.

At decision block 226, results of the evaluation are assessed. If acceptability is determined, then processing continues to block 228 to re-calculate the conversion function using the new matched data pair in the calibration set.

At block 228, the conversion function module re-creates the conversion function using the new matched data pair associated with the newly received reference data. In one embodiment, the conversion function module adds the newly received reference data (e.g., including the matched sensor data) into the calibration set, and recalculates the conversion function accordingly. In alternative embodiments, the conversion function module displaces the oldest, and/or least concordant matched data pair from the calibration set, and recalculates the conversion function accordingly.

At block 230, the sensor data transformation module uses the new conversion function (from block 228) to continually (or intermittently) convert sensor data into estimated analyte values, also referred to as calibrated data, or converted sensor data, such as is described in more detail above.

At block 232, an output module provides output to the user via the user interface. The output is representative of the estimated analyte value, which is determined by converting the sensor data into a meaningful analyte value. User output can be in the form of a numeric estimated analyte value, an indication of directional trend of analyte concentration, and/or a graphical representation of the estimated analyte data over a period of time, for example. Other representations of the estimated analyte values are also possible, for example audio and tactile.

If, however, acceptability is determined at decision block 226 as negative (unacceptable), then the processing progresses to block 234 to adjust the calibration set. In one embodiment of a calibration set adjustment, the conversion function module removes one or more oldest matched data pair(s) and recalculates the conversion function accordingly. In an alternative embodiment, the conversion function module removes the least concordant matched data pair from the calibration set, and recalculates the conversion function accordingly.

At block 236, the conversion function module re-creates the conversion function using the adjusted calibration set. While not wishing to be bound by theory, it is believed that removing the least concordant and/or oldest matched data pair(s) from the calibration set can reduce or eliminate the effects of sensor sensitivity drift over time, adjusting the conversion function to better represent the current sensitivity of the sensor.

At block 224, the evaluation module re-evaluates the acceptability of newly received reference data with time corresponding converted sensor data that has been converted using the new conversion function (block 236). The flow continues to decision block 238 to assess the results of the evaluation, such as described with reference to decision block 226, above. If acceptability is determined, then processing continues to block 230 to convert sensor data using the new conversion function and continuously display calibrated sensor data on the user interface.

If, however, acceptability is determined at decision block 226 as negative, then the processing loops back to block 234 to adjust the calibration set once again. This process can continue until the calibration set is no longer sufficient for calibration, for example, when the calibration set includes only one or no matched data pairs with which to create a conversion function. In this situation, the system can return to the initial calibration or start-up mode, which is described in more detail with reference to FIGS. 16 and 19, for example. Alternatively, the process can continue until inappropriate matched data pairs have been sufficiently purged and acceptability is positively determined.

In alternative embodiments, the acceptability is determined by a quality evaluation, for example, calibration quality can be evaluated by determining the statistical association of data that forms the calibration set, which determines the confidence associated with the conversion function used in calibration and conversion of raw sensor data into estimated analyte values. See, e.g., co-pending U.S. patent application Ser. No. 10/633,367 filed Aug. 1, 2003 entitled, "SYSTEM AND METHODS FOR PROCESSING ANALYTE SENSOR DATA."

Alternatively, each matched data pair can be evaluated based on clinical or statistical acceptability such as described above; however, when a matched data pair does not pass the evaluation criteria, the system can be configured to ask for another matched data pair from the user. In this way, a secondary check can be used to determine whether the error is more likely due to the reference glucose value or to the sensor value. If the second reference glucose value substantially correlates to the first reference glucose value, it can be presumed that the reference glucose value is more accurate and the sensor values are errant. Some reasons for errancy of the sensor values include a shift in the baseline of the signal or noise on the signal due to low oxygen, for example. In such cases, the system can be configured to re-initiate calibration using the secondary reference glucose value. If, however, the reference glucose values do not substantially correlate, it can be presumed that the sensor glucose values are more accurate and the reference glucose values eliminated from the algorithm.

Figure 18:
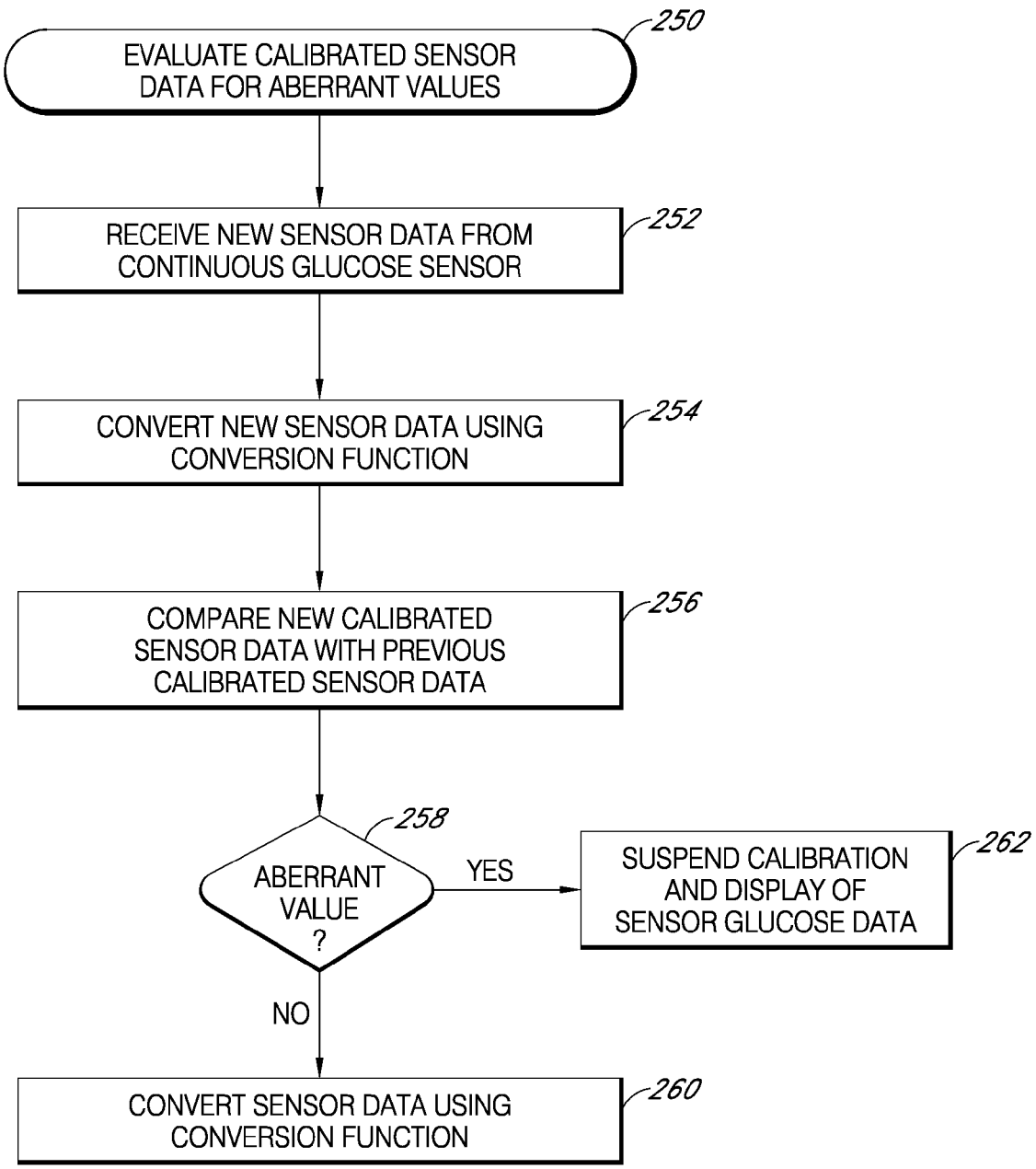
FIG. 18 is a flow chart that illustrates evaluation of calibrated sensor data for aberrant values.

FIG. 18 provides is a flow chart 250 that illustrates the evaluation of calibrated sensor data for aberrant values in one embodiment. Although sensor data are typically accurate and reliable, it can be advantageous to perform a self-diagnostic check of the calibrated sensor data prior to displaying the analyte data on the user interface.

One reason for anomalies in calibrated sensor data includes transient events, such as local ischemia at the implant site, which can temporarily cause erroneous readings caused by insufficient oxygen to react with the analyte. Accordingly, the flow chart 190 illustrates one self-diagnostic check that can be used to catch erroneous data before displaying it to the user.

At block 252, a sensor data receiving module, also referred to as the sensor data module, receives new sensor data from the sensor.

At block 24, the sensor data transformation module continuously (or intermittently) converts new sensor data into estimated analyte values, also referred to as calibrated data.

At block 256, a self-diagnostic module compares the new calibrated sensor data with previous calibrated sensor data, for example, the most recent calibrated sensor data value. In comparing the new and previous sensor data, a variety of parameters can be evaluated. In one embodiment, the rate of change and/or acceleration (or deceleration) of change of various analytes, which have known physiological limits within the body, and sensor data can be evaluated accordingly. For example, a limit can be set to determine if the new sensor data is within a physiologically feasible range, indicated by a rate of change from the previous data that is within known physiological (and/or statistical) limits. Similarly, any algorithm that predicts a future value of an analyte can be used to predict and then compare an actual value to a time corresponding predicted value to determine if the actual value falls within a statistically and/or clinically acceptable range based on the predictive algorithm, for example. In certain embodiments, identifying a disparity between predicted and measured analyte data can be used to identify a shift in signal baseline responsive to an evaluated difference between the predicted data and time-corresponding measured data. In some alternative embodiments, a shift in signal baseline and/or sensitivity can be determined by monitoring a change in the conversion function; namely, when a conversion function is re-calculated using the equation y=mx+b, a change in the values of m (sensitivity) or b (baseline) above a pre-selected "normal" threshold, can be used to trigger a fail-safe or further diagnostic evaluation.

Although the above-described self-diagnostics are generally employed with calibrated sensor data, some alternative embodiments are contemplated that check for aberrancy of consecutive sensor values prior to sensor calibration, for example, on the raw data stream and/or after filtering of the raw data stream. In certain embodiments, an intermittent or continuous signal-to-noise measurement can be evaluated to determine aberrancy of sensor data responsive to a signal-to-noise ratio above a set threshold. In certain embodiments, signal residuals (e.g., by comparing raw and filtered data) can be intermittently or continuously analyzed for noise above a set threshold. In certain embodiments, pattern recognition can be used to identify noise associated with physiological conditions, such as low oxygen (see, e.g., co-pending U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"), or other known signal aberrancies. Accordingly, in these embodiments, the system can be configured, in response to aberrancies in the data stream, to trigger signal estimation, adaptively filter the data stream according to the aberrancy, or the like, as described in more detail in the above cited co-pending U.S. application Ser. No. 10/648,849.

In another embodiment, reference analyte values are processed to determine a level of confidence, wherein reference analyte values are compared to their time-corresponding calibrated sensor values and evaluated for clinical or statistical accuracy. In yet another alternative embodiment, new and previous reference analyte data are compared in place of or in addition to sensor data. In general, there exist known patterns and limitations of analyte values that can be used to diagnose certain anomalies in raw or calibrated sensor and/or reference analyte data.

Block 193 describes additional systems and methods that can by utilized by the self-diagnostics module of the preferred embodiments.

At decision block 258, the system determines whether the comparison returned aberrant values. In one embodiment, the slope (rate of change) between the new and previous sensor data is evaluated, wherein values greater than +/−10, 15, 20, 25, or 30% or more change and/or +/−2, 3, 4, 5, 6 or more mg/dL/min, more preferably +/−4 mg/dL/min, rate of change are considered aberrant. In certain embodiments, other known physiological parameters can be used to determine aberrant values. However, a variety of comparisons and limitations can be set.

At block 260, if the values are not found to be aberrant, the sensor data transformation module continuously (or intermittently) converts received new sensor data into estimated analyte values, also referred to as calibrated data.

At block 262, if the values are found to be aberrant, the system goes into a suspended mode, also referred to as fail-safe mode in some embodiments, which is described in more detail below with reference to FIG. 19. In general, suspended mode suspends display of calibrated sensor data and/or insertion of matched data pairs into the calibration set. Preferably, the system remains in suspended mode until received sensor data is not found to be aberrant. In certain embodiments, a time limit or threshold for suspension is set, after which system and/or user interaction can be required, for example, requesting additional reference analyte data, replacement of the electronics unit, and/or reset.

In some alternative embodiments, in response to a positive determination of aberrant value(s), the system can be configured to estimate one or more glucose values for the time period during which aberrant values exist. Signal estimation generally refers to filtering, data smoothing, augmenting, projecting, and/or other methods for estimating glucose values based on historical data, for example. In one implementation of signal estimation, physiologically feasible values are calculated based on the most recent glucose data, and the aberrant values are replaced with the closest physiologically feasible glucose values. See also co-pending U.S. application Ser. No. 10/633,367 filed Aug. 1, 2003 entitled, "SYSTEM AND METHODS FOR PROCESSING ANALYTE SENSOR DATA," U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM," and U.S. Provisional Patent Application No. 60/528,382 filed Dec. 9, 2003 entitled, "SIGNAL PROCESSING FOR CONTINUOUS ANALYTE SENSORS."

Figure 19:
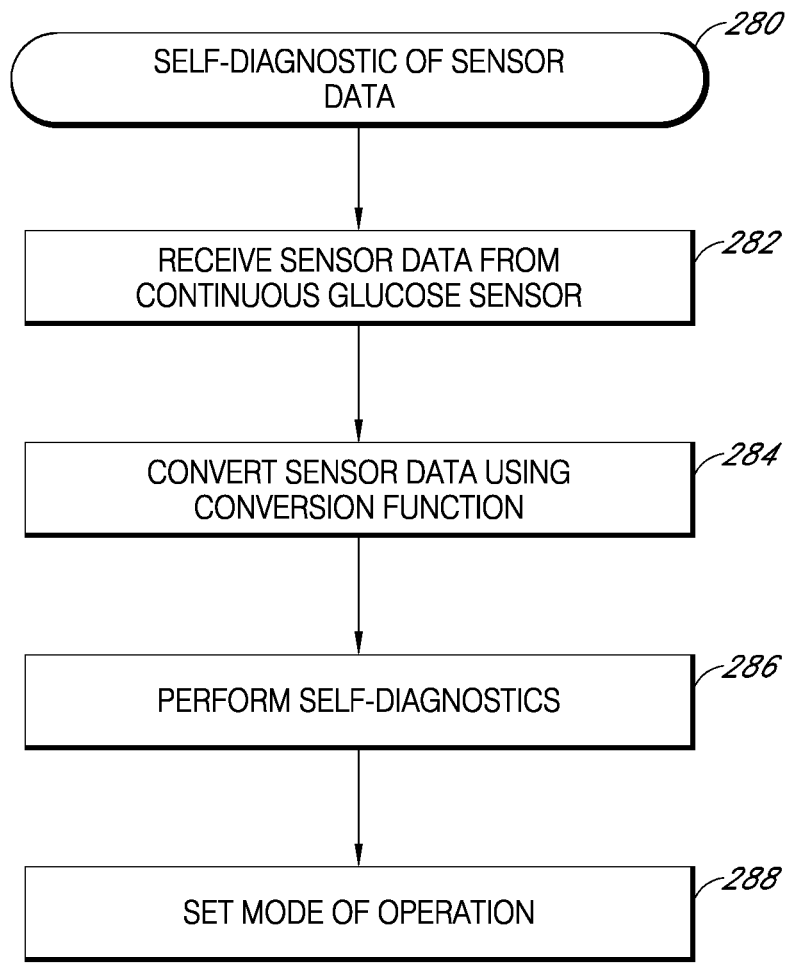
FIG. 19 is a flow chart that illustrates self-diagnostics of sensor data.

FIG. 19 provides a flow chart 280 that illustrates a self-diagnostic of sensor data in one embodiment. Although reference analyte values can useful for checking and calibrating sensor data, self-diagnostic capabilities of the sensor provide for a fail-safe for displaying sensor data with confidence and enable minimal user interaction (for example, requiring reference analyte values only as needed).

At block 282, a sensor data receiving module, also referred to as the sensor data module, receives new sensor data from the sensor.

At block 284, the sensor data transformation module continuously (or intermittently) converts received new sensor data into estimated analyte values, also referred to as calibrated data.

At block 286, a self-diagnostics module, also referred to as a fail-safe module, performs one or more calculations to determine the accuracy, reliability, and/or clinical acceptability of the sensor data. Some examples of the self-diagnostics module are described above, with reference block 256. The self-diagnostics module can be further configured to run periodically (e.g., intermittently or in response to a trigger), for example, on raw data, filtered data, calibrated data, predicted data, and the like.

In certain embodiments, the self-diagnostics module evaluates an amount of time since sensor insertion into the host, wherein a threshold is set for the sensor's usable life, after which time period the sensor is considered to be unreliable. In certain embodiments, the self-diagnostics module counts the number of times a failure or reset is required (for example, how many times the system is forced into suspended or start-up mode), wherein a count threshold is set for a predetermined time period, above which the system is considered to be unreliable. In certain embodiments, the self-diagnostics module compares newly received calibrated sensor data with previously calibrated sensor data for aberrant values, such as is described in more detail with reference to FIG. 5, above. In certain embodiments, the self-diagnostics module evaluates clinical acceptability, such as is described in more detail with reference to FIG. 18, above. In certain embodiments, diagnostics, such as are described in co-pending U.S. patent application Ser. No. 11/007,635 filed Dec. 7, 2004 and U.S. patent application Ser. No. 11/004,561 filed Dec. 3, 2004, can be incorporated into the systems of preferred embodiments for system diagnosis, for example, for identifying interfering species on the sensor signal and for identifying drifts in baseline and sensitivity of the sensor signal.

At block 288, a mode determination module, which can be a part of the sensor evaluation module 224, determines in which mode the sensor should be set (or remain). In some embodiments, the system is programmed with three modes: 1) start-up mode; 2) normal mode; and 3) suspended mode. Although three modes are described herein, the preferred embodiments are limited to the number or types of modes with which the system can be programmed. In some embodiments, the system is defined as "in-cal" (in calibration) in normal mode; otherwise, the system is defined as "out-of-cal" (out of calibration) in start-up and suspended mode. The terms as used herein are meant to describe the functionality and are not limiting in their definitions.

Preferably, a start-up mode is provided, wherein the start-up mode is set when the system determines that it can no longer remain in suspended or normal mode (for example, due to problems detected by the self-diagnostics module, such as described in more detail above) and/or wherein the system is notified that a new sensor has been inserted. Upon initialization of start-up mode, the system ensures that any old matched data pairs and/or calibration information is purged. In start-up mode, the system initializes the calibration set, such as described in more detail with reference to FIG. 13, above. Once the calibration set has been initialized, sensor data is ready for conversion and the system is set to normal mode.

Preferably, a normal mode is provided, wherein the normal mode is set when the system is accurately and reliably converting sensor data, for example, wherein clinical acceptability is positively determined, aberrant values are negatively determined, and/or the self-diagnostics modules confirms reliability of data. In normal mode, the system continuously (or intermittently) converts (calibrates) sensor data. Additionally, reference analyte values received by the system are matched with sensor data points and added to the calibration set.

In certain embodiments, the calibration set is limited to a predetermined number of matched data pairs, after which the systems purges old or less desirable matched data pairs when a new matched data pair is added to the calibration set. Less desirable matched data pairs can be determined by inclusion criteria, which include one or more criteria that define a set of matched data pairs that form a substantially optimal calibration set.

One inclusion criterion comprises ensuring the time stamp of the matched data pairs (that make up the calibration set) span at least a preselected time period (e.g., three hours). Another inclusion criterion comprises ensuring that the time stamps of the matched data pairs are not more than a preselected age (e.g., one week old). Another inclusion criterion ensures that the matched pairs of the calibration set have a substantially evenly distributed amount of high and low raw sensor data points, estimated sensor analyte values, and/or reference analyte values. Another criterion comprises ensuring all raw sensor data, estimated sensor analyte values, and/or reference analyte values are within a predetermined range (e.g., 40 mg/dL to 400 mg/dL for glucose values). Another criterion comprises evaluating the rate of change of the analyte concentration (e.g., from sensor data) during the time stamp of the matched pair(s). For example, sensor and reference data obtained during the time when the analyte concentration is undergoing a slow rate of change can be less susceptible to inaccuracies caused by time lag and other physiological and non-physiological effects. Another criterion comprises evaluating the congruence of respective sensor and reference data in each matched data pair; the matched pairs with the most congruence can be chosen. Another criterion comprises evaluating physiological changes (e.g., low oxygen due to a user's posture, position, or motion that can cause pressure on the sensor and effect the function of a subcutaneously implantable analyte sensor, or other effects such as described with reference to FIG. 6) to ascertain a likelihood of error in the sensor value. Evaluation of calibration set criteria can comprise evaluating one, some, or all of the above described inclusion criteria. It is contemplated that additional embodiments can comprise additional inclusion criteria not explicitly described herein.

Unfortunately, some circumstances can exist wherein a system in normal mode can be changed to start-up or suspended mode. In general, the system is programmed to change to suspended mode when a failure of clinical acceptability, aberrant value check and/or other self-diagnostic evaluation is determined, such as described in more detail above, and wherein the system requires further processing to determine whether a system re-start is required (e.g., start-up mode). In general, the system will change to start-up mode when the system is unable to resolve itself in suspended mode and/or when the system detects a new sensor has been inserted (e.g., via system trigger or user input).

Preferably, a suspended mode is provided wherein the suspended mode is set when a failure of clinical acceptability, aberrant value check, and/or other self-diagnostic evaluation determines unreliability of sensor data. In certain embodiments, the system enters suspended mode when a predetermined time period passes without receiving a reference analyte value. In suspended mode, the calibration set is not updated with new matched data pairs, and sensor data can optionally be converted, but not displayed on the user interface. The system can be changed to normal mode upon resolution of a problem (positive evaluation of sensor reliability from the self-diagnostics module, for example). The system can be changed to start-up mode when the system is unable to resolve itself in suspended mode and/or when the system detects a new sensor has been inserted (via system trigger or user input).

The systems of preferred embodiments, including a transcutaneous analyte sensor, mounting unit, electronics unit, applicator, and receiver for inserting the sensor, and measuring, processing, and displaying sensor data, provide improved convenience and accuracy because of their designed stability within the host's tissue with minimum invasive trauma, while providing a discreet and reliable data processing and display, thereby increasing overall host comfort, confidence, safety, and convenience. Namely, the geometric configuration, sizing, and material of the sensor of the preferred embodiments enable the manufacture and use of an atraumatic device for continuous measurement of analytes, in contrast to conventional continuous glucose sensors available to persons with diabetes, for example. Additionally, the sensor systems of preferred embodiments provide a comfortable and reliable system for inserting a sensor and measuring an analyte level for up to 7 days or more without surgery. The sensor systems of the preferred embodiments are designed for host comfort, with chemical and mechanical stability that provides measurement accuracy. Furthermore, the mounting unit is designed with a miniaturized and reusable electronics unit that maintains a low profile during use. The usable life of the sensor can be extended by incorporation of a bioactive agent into the sensor that provides local release of an anti-inflammatory, for example, in order to slow the subcutaneous foreign body response to the sensor.

After the usable life of the sensor (for example, due to a predetermined expiration, potential infection, or level of inflammation), the host can remove the sensor and mounting from the skin, and dispose of the sensor and mounting unit (preferably saving the electronics unit for reuse). Another sensor system can be inserted with the reusable electronics unit and thus provide continuous sensor output for long periods of time.

EXAMPLES

Figure 20A:
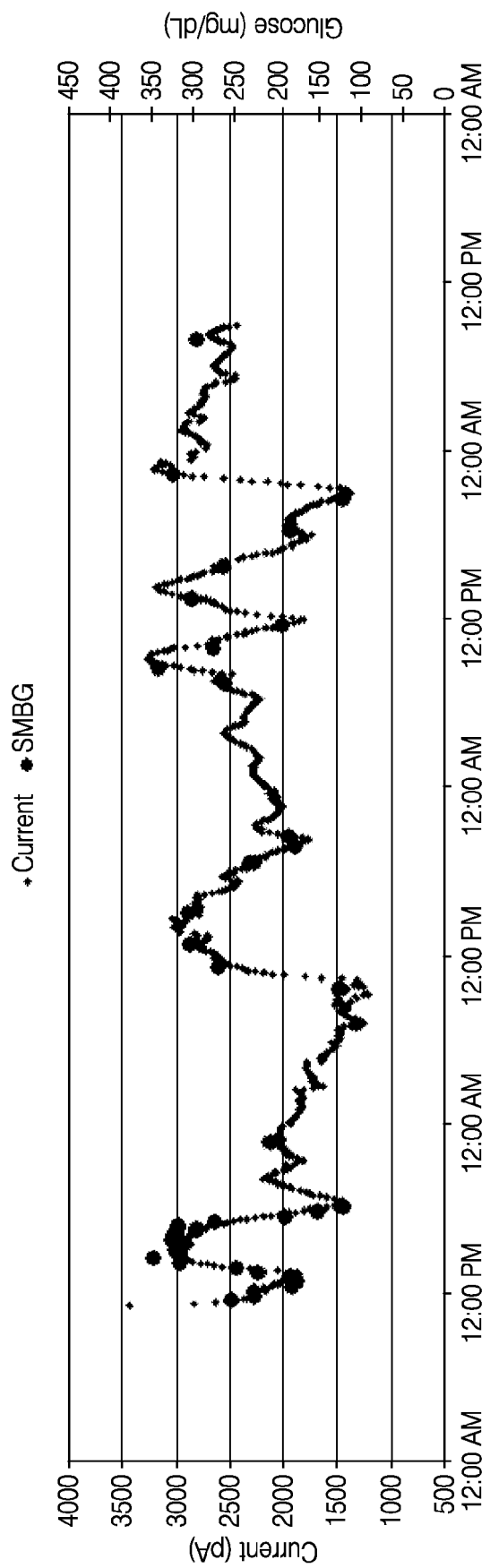
FIGS. 20A and 20B are graphical representations of glucose sensor data in a human obtained over approximately three days.

FIG. 20A is a graphical representation showing transcutaneous glucose sensor data and corresponding blood glucose values over time in a human. The x-axis represents time, the first y-axis represents current in picoAmps, and the second y-axis represents blood glucose in mg/dL. As depicted on the legend, the small diamond points represent the current measured from the working electrode of a transcutaneous glucose sensor of a preferred embodiment; while the larger points represent blood glucose values of blood withdrawn from a finger stick and analyzed using an in vitro self-monitoring blood glucose meter (SMBG).

A transcutaneous glucose sensor was built according to the preferred embodiments and implanted in a human host where it remained over a period of time. The graph illustrates approximately 3 days of data obtained by the electronics unit operably connected to the sensor implanted in the human host. Finger-prick blood samples were taken periodically and glucose concentration measured by a blood glucose meter (SMBG). The graph shows the subcutaneous sensor data obtained by the transcutaneous glucose sensor tracking glucose concentration as it rises and falls over time. The time-corresponding blood glucose values show the correlation of the sensor data to the blood glucose data, indicating appropriate tracking of glucose concentration over time.

The signal has a current measurement in the picoAmp range. Namely, for every unit (mg/dL) of glucose, approximately 3.5 to 7.5 pA of current is measured. Generally, the approximately 3.5 to 7.5 pA/mg/dL sensitivity exhibited by the device can be attributed to a variety of design factors, including resistance of the membrane system to glucose, amount of enzyme in the membrane system, surface area of the working electrode, and electronic circuitry design. Accordingly, a current in the picoAmp range enables an analyte sensor that: 1) requires (or utilizes) less enzyme (e.g., because the membrane system is highly resistive and allows less glucose through for reaction in the enzyme domain); 2) requires less oxygen (e.g. because less reaction of glucose in the enzyme domain requires less oxygen as a co-reactant) and therefore performs better during transient ischemia of the subcutaneous tissue; and 3) accurately measures glucose even in hypoglycemic ranges (e.g., because the electronic circuitry is able to measure very small amounts of glucose (hydrogen peroxide at the working electrode)). Advantageously, the analyte sensors of the preferred embodiments exhibit improved performance over convention analyte sensors at least in part because a current in the picoAmp range enables less enzyme, less oxygen, better resolution, lower power usage, and therefore better performance in the hypoglycemic range wherein lower mg/dL values conventionally have yielded lower accuracy.

Figure 20B:
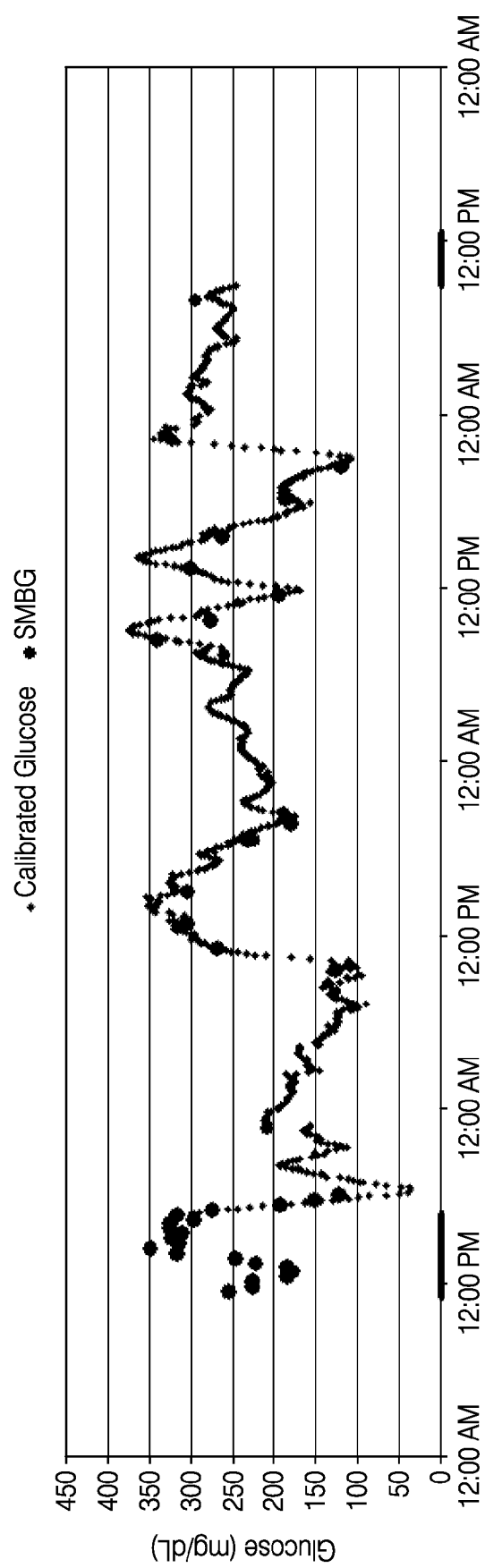

FIG. 20B is a graphical representation showing transcutaneous glucose sensor data and corresponding blood glucose values over time in a human. The x-axis represents time; the y-axis represents glucose concentration in mg/dL. As depicted on the legend, the small diamond points represent the calibrated glucose data measured from a transcutaneous glucose sensor of a preferred embodiment; while the larger points represent blood glucose values of blood withdrawn from a finger stick and analyzed using an in vitro self-monitoring blood glucose meter (SMBG). The calibrated glucose data corresponds to the data of FIG. 20A shown in current, except it has been calibrated using algorithms of the preferred embodiments. Accordingly, accurate subcutaneous measurement of glucose concentration has been measured and processed using the systems and methods of the preferred embodiments.

Methods and devices that are suitable for use in conjunction with aspects of the preferred embodiments are disclosed in U.S. Pat. No. 4,994,167 issued Feb. 19, 1991 and entitled "BIOLOGICAL FLUID MEASURING DEVICE"; U.S. Pat. No. 4,757,022 issued Feb. Jul. 12, 1988 and entitled "BIOLOGICAL FLUID MEASURING DEVICE"; U.S. Pat. No. 6,001,067 issued Feb. Dec. 14, 1999 and entitled "DEVICE AND METHOD FOR DETERMINING ANALYTE LEVELS"; U.S. Pat. No. 6,741,877 issued Feb. May 25, 2004 and entitled "DEVICE AND METHOD FOR DETERMINING ANALYTE LEVELS"; U.S. Pat. No. 6,702,857 issued Feb. Mar. 9, 2004 and entitled "MEMBRANE FOR USE WITH IMPLANTABLE DEVICES"; and U.S. Pat. No. 6,558,321 issued Feb. May 6, 2003 and entitled "SYSTEMS AND METHODS FOR REMOTE MONITORING AND MODULATION OF MEDICAL DEVICES." Methods and devices that are suitable for use in conjunction with aspects of the preferred embodiments are disclosed in co-pending U.S. application Ser. No. 10/991,353 filed Nov. 16, 2004 and entitled "AFFINITY DOMAIN FOR ANALYTE SENSOR"; U.S. application Ser. No. 11/055,779 filed Feb. 9, 2005 and entitled "BIOINTERFACE WITH MACRO-AND-MICRO-ARCHITECTURE"; U.S. application Ser. No. 11/004,561 filed Dec. 3, 2004 and entitled "CALIBRATION TECHNIQUES FOR A CONTINUOUS ANALYTE SENSOR"; U.S. application Ser. No. 11/034,343 filed Jan. 11, 2005 and entitled "COMPOSITE MATERIAL FOR IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 11/021,046 filed Dec. 22, 2004 and entitled "DEVICE AND METHOD FOR DETERMINING ANALYTE LEVELS"; U.S. application Ser. No. 09/916,858 filed Jul. 27, 2001 and entitled "DEVICE AND METHOD FOR DETERMINING ANALYTE LEVELS"; U.S. application Ser. No. 11/039,269 filed Jan. 19, 2005 and entitled "DEVICE AND METHOD FOR DETERMINING ANALYTE LEVELS"; U.S. application Ser. No. 10/897,377 filed Jul. 21, 2004 and entitled "ELECTROCHEMICAL SENSORS INCLUDING ELECTRODE SYSTEMS WITH INCREASED OXYGEN GENERATION"; U.S. application Ser. No. 10/897,312 filed Jul. 21, 2004 and entitled "ELECTRODE SYSTEMS FOR ELECTROCHEMICAL SENSORS"; U.S. application Ser. No. 10/838,912 filed May 3, 2004 and entitled "IMPLANTABLE ANALYTE SENSOR"; U.S. application Ser. No. 10/838,909 filed May 3, 2004 and entitled "IMPLANTABLE ANALYTE SENSOR"; U.S. application Ser. No. 10/838,658 filed May 3, 2004 and entitled "IMPLANTABLE ANALYTE SENSOR"; U.S. application Ser. No. 11/034,344 filed Jan. 11, 2005 and entitled "IMPLANTABLE DEVICE WITH IMPROVED RADIO FREQUENCY CAPABILITIES"; U.S. application Ser. No. 10/896,772 filed Jul. 21, 2004 and entitled "INCREASING BIAS FOR OXYGEN PRODUCTION IN AN ELECTRODE SYSTEM"; U.S. application Ser. No. 10/789,359 filed Feb. 26, 2004 and entitled "INTEGRATED DELIVERY DEVICE FOR CONTINUOUS GLUCOSE SENSOR"; U.S. application Ser. No. 10/991,966 filed Nov. 17, 2004 and entitled "INTEGRATED RECEIVER FOR CONTINUOUS ANALYTE SENSOR"; U.S. application Ser. No. 10/646,333 filed Aug. 22, 2003 and entitled "OPTIMIZED SENSOR GEOMETRY FOR AN IMPLANTABLE GLUCOSE SENSOR"; U.S. application Ser. No. 10/896,639 filed Jul. 21, 2004 and entitled "OXYGEN ENHANCING MEMBRANE SYSTEMS FOR IMPLANTABLE DEVICES"; U.S. application Ser. No. 10/647,065 filed Aug. 22, 2003 and entitled "POROUS MEMBRANES FOR USE WITH IMPLANTABLE DEVICES"; U.S. application Ser. No. 10/896,637 filed Jul. 21, 2004 and entitled "ROLLED ELECTRODE ARRAY AND ITS METHOD FOR MANUFACTURE"; U.S. application Ser. No. 09/916,711 filed Jul. 27, 2001 and entitled "SENSOR HEAD FOR USE WITH IMPLANTABLE DEVICE"; U.S. application Ser. No. 11/021,162 filed Dec. 22, 2004 and entitled "SENSOR HEAD FOR USE WITH IMPLANTABLE DEVICES"; U.S. application Ser. No. 11/007,920 filed Dec. 8, 2004 and entitled "SIGNAL PROCESSING FOR CONTINUOUS ANALYTE SENSOR"; U.S. application Ser. No. 10/695,636 filed Oct. 28, 2003 and entitled "SILICONE COMPOSITION FOR BIOCOMPATIBLE MEMBRANE"; U.S. application Ser. No. 11/038,340 filed Jan. 18, 2005 and entitled "SYSTEM AND METHODS FOR PROCESSING ANALYTE SENSOR DATA"; U.S. application Ser. No. 11/007,635 filed Dec. 7, 2004 and entitled "SYSTEMS AND METHODS FOR IMPROVING ELECTROCHEMICAL ANALYTE SENSORS"; U.S. application Ser. No. 10/885,476 filed Jul. 6, 2004 and entitled "SYSTEMS AND METHODS FOR MANUFACTURE OF AN ANALYTE-MEASURING DEVICE INCLUDING A MEMBRANE SYSTEM"; U.S. application Ser. No. 10/648,849 filed Aug. 22, 2003 and entitled "SYSTEMS AND METHODS FOR REPLACING SIGNAL ARTIFACTS IN A GLUCOSE SENSOR DATA STREAM"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 10/846,150 filed May 14, 2004 and entitled "ANALYTE MEASURING DEVICE"; U.S. application Ser. No. 10/842,716 filed May 10, 2004 and entitled "BIOINTERFACE MEMBRANES INCORPORATING BIOACTIVE AGENTS"; U.S. application Ser. No. 10/657,843 filed Sep. 9, 2003 and entitled "DEVICE AND METHOD FOR DETERMINING ANALYTE LEVELS"; U.S. application Ser. No. 10/768,889 filed Jan. 29, 2004 and entitled "MEMBRANE FOR USE WITH IMPLANTABLE DEVICES"; U.S. application Ser. No. 10/633,367 filed Aug. 1, 2003 and entitled "SYSTEM AND METHODS FOR PROCESSING ANALYTE SENSOR DATA"; U.S. application Ser. No. 10/632,537 filed Aug. 1, 2003 and entitled "SYSTEM AND METHODS FOR PROCESSING ANALYTE SENSOR DATA"; U.S. application Ser. No. 10/633,404 filed Aug. 1, 2003 and entitled "SYSTEM AND METHODS FOR PROCESSING ANALYTE SENSOR DATA"; U.S. application Ser. No. 10/633,329 filed Aug. 1, 2003 and entitled "SYSTEM AND METHODS FOR PROCESSING ANALYTE SENSOR DATA"; and U.S. Application No. 60/660,743 filed on Mar. 10, 2005 and entitled "SYSTEMS AND METHODS FOR PROCESSING ANALYTE SENSOR DATA FOR SENSOR CALIBRATION."

All references cited herein, including but not limited to published and unpublished applications, patents, and literature references, and also including but not limited to the references listed in the Appendix, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. A method for processing sensor data, comprising:
   generating sensor data from a continuous glucose sensor, wherein the sensor data is indicative of a glucose concentration in a host;
   receiving reference data from a reference glucose monitor, wherein the reference data is indicative of a glucose concentration in the host;
   determining, using a processor module, a conversion function associated with the continuous glucose sensor, wherein the conversion function comprises a first baseline value;
   testing the conversion function using one or more predetermined criteria; and
   wherein if the conversion function fails one or more of the predetermined testing criteria, then modifying the first baseline value to obtain a second baseline value using predetermined baseline information without reference data obtained from an in vitro self-monitoring blood glucose test after implantation in vivo.

2. The method of claim 1, wherein the predetermined baseline information is obtained from in vivo testing of at least one other continuous glucose sensor.

3. The method of claim 1, wherein the predetermined baseline information comprises a range of predetermined baseline values.

4. The method of claim 1, further comprising converting the sensor data using the conversion function if the conversion functions passes one or more of the predetermined criteria of the testing.

5. The method of claim 1, further comprising repeating the testing using a modified conversion function comprising the second baseline value.

6. The method of claim 1, wherein the one or more predetermined testing criteria comprise predetermined sensitivity information and/or predetermined baseline information.

7. The method of claim 6, wherein the predetermined sensitivity information and/or predetermined baseline information are derived from in vivo testing of at least one other continuous glucose sensor or in vitro testing.

8. The method of claim 1, wherein the predetermined baseline information is obtained from in vivo testing of at least one other continuous glucose sensor or in vitro testing.

9. A system for processing sensor data, comprising:
   a continuous glucose sensor configured to provide sensor data indicative of a glucose concentration in a host; and
   a processor module configured to
      determine a conversion function associated with the continuous glucose sensor, wherein the conversion function comprises using predetermined baseline information to guide or validate the conversion function, wherein the conversion function comprises a sensitivity value and a first baseline value,
      test the conversion function using one or more predetermined criteria, and
      modify the first baseline value if the conversion function fails one or more of the predetermined test criteria, and wherein the first baseline value is modified to obtain a second baseline value using predetermined baseline information without reference data obtained from an in vitro self-monitoring blood glucose test after implantation in vivo, and wherein the processor module is configured to process the sensor data using the modified conversion function comprising the second baseline value.

10. The system of claim 9, wherein the predetermined baseline information is obtained from in vivo testing of at least one other continuous glucose sensor.

11. The system of claim 9, wherein the predetermined baseline information comprises a range of acceptable baseline values.

12. The system of claim 11, wherein the processor module is configured to convert the sensor data using the conversion function if the conversion function passes one or more of the predetermined test criteria.

13. The system of claim 9, wherein the processor module is configured to test the modified conversion function.

14. The system of claim 9, wherein the one or more predetermined test criteria comprises predetermined sensitivity information and/or predetermined baseline information.

15. The system of claim 14, wherein the predetermined sensitivity information and/or the predetermined baseline information are derived from at least one of in vivo testing of at least one other continuous glucose sensor or in vitro testing.

16. The system of claim 9, wherein the predetermined baseline information is obtained from in vivo testing of at least one other continuous glucose sensor or in vitro testing.

17. The system of claim 9, further comprising:
   a transmitter unit operably coupled to the glucose sensor, the transmitter unit having a radio frequency transmitter configured to wirelessly transmit sensor data; and
   a receiver unit comprising a radio frequency receiver and a display, the radio frequency receiver configured to receive the transmitted sensor data and the display configured to display information based on the transmitted sensor data.

18. The system of claim 17, wherein the processor module is incorporated in the transmitter unit, wherein the processor module is configured to process the sensor data prior to the sensor data being transmitted by the radio frequency transmitter.

* * * * *

UNITED STATES PATENT AND TRADEMARK OFFICE
CERTIFICATE OF CORRECTION

| | | |
|---|---|---|
| PATENT NO. | : 8,565,849 B2 | |
| APPLICATION NO. | : 12/780739 | |
| DATED | : October 22, 2013 | |
| INVENTOR(S) | : Kamath et al. | |

It is certified that error appears in the above-identified patent and that said Letters Patent is hereby corrected as shown below:

On the Title Page, References Cited

In column 1 (page 7, item 56) line 52, Under Other Publications, change "xenogenic." to --xenogeneic.--.

In column 1 (page 7, item 56) line 54, Under Other Publications, change "xenogenic." to --xenogeneic.--.

In column 1 (page 8, item 56) line 16, Under Other Publications, change "basedon" to --based on--.

In column 1 (page 8, item 56) line 33, Under Other Publications, change "curent." to --current.--.

In column 1 (page 8, item 56) line 42, Under Other Publications, change "Potentially-impintable," to --Potentially-implantable,--.

In column 1 (page 8, item 56) line 47, Under Other Publications, change "reliablity" to --reliability--.

In column 1 (page 8, item 56) line 58, Under Other Publications, change "Enzymlology," to --Enzymology,--.

In column 2 (page 8, item 56) line 5, Under Other Publications, change "artifical" to --artificial--.

In column 2 (page 8, item 56) line 23, Under Other Publications, change "your" to --you--.

In column 2 (page 8, item 56) line 36, Under Other Publications, change "dynamcs" to --dynamics--.

In column 2 (page 8, item 56) line 39, Under Other Publications, change "glocuse" to --glucose--.

Signed and Sealed this
Twentieth Day of May, 2014

Michelle K. Lee
*Deputy Director of the United States Patent and Trademark Office*

CERTIFICATE OF CORRECTION (continued)  
U.S. Pat. No. 8,565,849 B2

In column 2 (page 8, item 56) line 40, Under Other Publications, change "Diabetese" to --Diabetes--.

In column 2 (page 8, item 56) line 71, Under Other Publications, change "Diabetese" to --Diabetes--.

In column 1 (page 9, item 56) line 29, Under Other Publications, change "inactiviation" to --inactivation--.

In column 1 (page 9, item 56) line 46, Under Other Publications, change "patents" to --patients--.

In column 1 (page 10, item 56) line 43, Under Other Publications, change "Beioelectronics," to --Bioelectronics,--.

In column 1 (page 10, item 56) line 44, Under Other Publications, change "glocuse" to --glucose--.

In column 1 (page 10, item 56) line 62, Under Other Publications, change "valication" to --validation--.

In column 1 (page 10, item 56) line 63, Under Other Publications, change "glucose-iunsulin" to --glucose-insulin--.

In column 1 (page 10, item 56) line 63, Under Other Publications, change "interaaction in tyhpe 1" to --interaction in type 1--.

In column 2 (page 10, item 56) line 37, Under Other Publications, change "artifical" to --artificial--.

In column 2 (page 10, item 56) line 51, Under Other Publications, change "amperometeric" to --amperometric--.

In column 1 (page 11, item 56) line 41, Under Other Publications, change "termistor" to --thermistor--.

In column 1 (page 11, item 56) line 42, Under Other Publications, change "metobolites," to --metabolites,--.

In column 1 (page 11, item 56) line 44, Under Other Publications, change "cholesteral and cholesteral" to --cholesterol and cholesterol--.

In column 1 (page 11, item 56) line 54, Under Other Publications, change "Apllied" to --Applied--.

In column 1 (page 12, item 56) line 13, Under Other Publications, change "Subcutaenous" to --Subcutaneous--.

In column 1 (page 13, item 56) line 7, Under Other Publications, change "blod" to --blood--.

In column 1 (page 13, item 56) line 34, Under Other Publications, change "Deabetes" to --Diabetes--.

CERTIFICATE OF CORRECTION (continued)
U.S. Pat. No. 8,565,849 B2

In the Specification

In column 4 line 43, change "andrenostenedione;" to --androstenedione--.

In column 4 line 53, change "hemoglobin S" to --hemoglobin S,--.

In column 4 line 58, change "diptheria/" to --diphtheria/--.

In column 4 line 65, change "perioxidase;" to --peroxidase;--.

In column 5 line 4, change "phenyloin;" to --phenytoin;--.

In column 5 line 19, change "Trepenoma pallidium," to --Treponema pallidum,--.

In column 5 line 20, change "stomatis" to --stomatitis--.

In column 5 line 41, change "(barbituates," to --(barbiturates,--.

In column 6 line 1, change "and or" to --and/or--.

In column 12 line 57, change "employed" to --employed.--.

In column 13 line 27, change "FIG." to --FIGS.--.

In column 14 line 27, change "of" to --off--.

In column 14 line 66, change "by" to --be--.

In column 15 line 39, change "Bellafonte," to --Bellefonte,--.

In column 26 line 63, change "))" to --.--.

In column 27 lines 42-43, change "hydroxyethylmetharcrylate," to --hydroxyethylmethacrylate,--.

In column 27 line 43, change "hydroxyapeptite," to --hydroxyapatite,--.

In column 27 line 45, change "nintinol," to --nitinol,--.

In column 31 line 13, change "and or" to --and/or--.

In column 35 line 2, change "pad" to --pad.--.

In column 37 line 54, change "of" to --off--.

In column 38 line 62, change "and or" to --and/or--.

In column 44 line 18, change "vivo" to --vivo,--.

In column 58 line 31, change "by" to --be--.

In column 63 line 2, change "Feb. Jul." to --Jul.--.

In column 63 line 4, change "Feb. Dec." to --Dec.--.

In column 63 line 6, change "Feb. May." to --May.--.

In column 63 lines 8-9, change "Feb. Mar" to --Mar.--.

In column 63 line 11, change "Feb. May." to --May.--.

In the Claims

In column 66 line 4, In Claim 9, change "to" to --to:--.

In column 66 line 17, In Claim 9, change "using" to --using the--.